US010485972B2

(12) United States Patent
Pal et al.

(10) Patent No.: US 10,485,972 B2
(45) Date of Patent: *Nov. 26, 2019

(54) APPARATUSES AND METHODS FOR NEUROMODULATION

(71) Applicant: Thync Global, Inc., Los Gatos, CA (US)

(72) Inventors: Sumon K. Pal, Boston, MA (US); William J. Tyler, Newton, MA (US); Jonathan D. Charlesworth, Boston, MA (US); Isy Goldwasser, Los Gatos, CA (US); Daniel Z. Wetmore, Brooklyn, NY (US); Jason Egnal, Menlo Park, CA (US); Anil Thakur, Fremont, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/170,878

(22) Filed: Jun. 1, 2016

(65) Prior Publication Data

US 2016/0346545 A1    Dec. 1, 2016

Related U.S. Application Data

(60) Provisional application No. 62/169,522, filed on Jun. 1, 2015, provisional application No. 62/169,523, filed (Continued)

(51) Int. Cl.
*A61N 1/36*       (2006.01)
*A61N 1/04*       (2006.01)

(52) U.S. Cl.
CPC ........ *A61N 1/36025* (2013.01); *A61N 1/0456* (2013.01); *A61N 1/0492* (2013.01)

(58) Field of Classification Search
CPC .............. A61N 1/36025; A61N 1/0456; A61N 1/0476; A61N 1/0492
See application file for complete search history.

(56) References Cited

U.S. PATENT DOCUMENTS 3,255,753 A    6/1966  Wing
3,388,699 A    1/1968  Webb et al.
(Continued)

FOREIGN PATENT DOCUMENTS

CN    1204268 A    1/1999
CN    1607970 A    4/2005
(Continued)

OTHER PUBLICATIONS

Pal et al.; U.S. Appl. No. 14/956,193 entitled "Transdermal electrical stimulation devices for modifying or inducing cognitive state," filed Dec. 1, 2015.
(Continued)

*Primary Examiner* — Joseph M Dietrich
(74) *Attorney, Agent, or Firm* — Shay Glenn LLP

(57) ABSTRACT

Apparatuses and methods of applying transdermal electrical stimulation (TES) to a subject to enhance a concurrent sensory experience, by applying the TES to the subject's head or head and neck from two or more electrodes that are coupled to a neurostimulator. The apparatuses and methods described herein be configured to apply an ensemble current waveform between the two or more electrodes, wherein the ensemble current waveform comprises a series of component waveforms that are sequentially applied, and wherein each component waveform is different from a component waveform immediately before it and wherein transitions between the component waveforms temporally correlates with transitions in the sensory experience. Also described herein are apparatuses and methods for applying TES to a subject's face or face and neck, wherein one end of the TES (Continued)

applicator (e.g., strip electrode) contacts the subject's cheek and/or mastoid. Finally, user interfaces for controlling TES are also described.

19 Claims, 48 Drawing Sheets

Related U.S. Application Data on Jun. 1, 2015, provisional application No. 62/170,111, filed on Jun. 2, 2015, provisional application No. 62/268,084, filed on Dec. 16, 2015.

(56) References Cited

U.S. PATENT DOCUMENTS

| | | | |
|---|---|---|---|
| 3,620,219 A * | 11/1971 | Barker | A61N 1/0456 351/158 |
| 3,648,708 A | 3/1972 | Haeri | |
| 3,762,396 A | 10/1973 | Ballentine et al. | |
| 4,418,687 A | 12/1983 | Matsumoto et al. | |
| 4,431,000 A | 2/1984 | Butler et al. | |
| 4,646,744 A | 3/1987 | Capel | |
| 4,664,117 A | 5/1987 | Beck | |
| 4,865,048 A | 9/1989 | Eckerson | |
| 5,144,952 A | 9/1992 | Frachet et al. | |
| 5,183,041 A | 2/1993 | Toriu et al. | |
| 5,335,657 A | 8/1994 | Terry et al. | |
| 5,342,410 A | 8/1994 | Braverman | |
| 5,397,338 A | 3/1995 | Grey et al. | |
| 5,476,481 A | 12/1995 | Schondorf | |
| 5,487,759 A | 1/1996 | Bastyr et al. | |
| 5,514,175 A | 5/1996 | Kim et al. | |
| 5,540,736 A | 7/1996 | Haimovich et al. | |
| 5,573,552 A | 11/1996 | Hansjurgens | |
| 5,578,065 A | 11/1996 | Hattori et al. | |
| 5,593,427 A | 1/1997 | Gliner et al. | |
| 5,738,647 A | 4/1998 | Bernhard et al. | |
| 5,792,067 A | 8/1998 | Karell | |
| 6,066,163 A | 5/2000 | John | |
| 6,280,454 B1 | 8/2001 | Wang | |
| 6,324,432 B1 | 11/2001 | Rigaux et al. | |
| 6,445,955 B1 | 9/2002 | Michelson et al. | |
| 6,463,328 B1 | 10/2002 | John | |
| 6,516,227 B1 | 2/2003 | Meadows et al. | |
| 6,526,318 B1 | 2/2003 | Ansarinia | |
| 6,567,702 B1 | 5/2003 | Nekhendzy et al. | |
| 6,731,987 B1 | 5/2004 | McAdams et al. | |
| 6,983,184 B2 | 1/2006 | Price | |
| 7,120,499 B2 | 10/2006 | Thrope et al. | |
| 7,146,217 B2 | 12/2006 | Firlik et al. | |
| 7,263,501 B2 | 8/2007 | Tirinato et al. | |
| 7,376,467 B2 | 5/2008 | Thrope et al. | |
| 7,422,555 B2 | 9/2008 | Zabara | |
| 7,577,481 B2 | 8/2009 | Firlik et al. | |
| 7,660,636 B2 | 2/2010 | Castel et al. | |
| 7,801,600 B1 | 9/2010 | Carbunaru et al. | |
| 7,891,615 B2 | 2/2011 | Bevirt | |
| 7,949,403 B2 | 5/2011 | Palermo et al. | |
| 8,029,431 B2 | 10/2011 | Tononi | |
| 8,034,294 B1 | 10/2011 | Goldberg | |
| 8,086,318 B2 | 12/2011 | Strother et al. | |
| 8,097,926 B2 | 1/2012 | De Graff et al. | |
| 8,116,875 B2 | 2/2012 | Osypka et al. | |
| 8,121,695 B2 | 2/2012 | Gliner et al. | |
| 8,150,537 B2 | 4/2012 | Tanaka et al. | |
| 8,190,248 B2 | 5/2012 | Besio et al. | |
| 8,197,276 B2 | 6/2012 | Egloff et al. | |
| 8,204,601 B2 | 6/2012 | Moyer et al. | |
| 8,239,030 B1 | 8/2012 | Hagedorn et al. | |
| 8,265,761 B2 | 9/2012 | Siever | |
| 8,280,502 B2 | 10/2012 | Hargrove et al. | |
| 8,346,337 B2 | 1/2013 | Heller | |
| 8,380,315 B2 | 2/2013 | DeGiorgio et al. | |
| 8,428,738 B2 | 4/2013 | Valencia | |
| 8,463,383 B2 | 6/2013 | Sakai et al. | |
| 8,494,625 B2 | 7/2013 | Hargrove | |
| 8,494,627 B2 | 7/2013 | Bikson et al. | |
| 8,506,469 B2 | 8/2013 | Dietrich et al. | |
| 8,532,758 B2 | 9/2013 | Silverstone | |
| 8,560,075 B2 | 10/2013 | Covalin | |
| 8,571,651 B2 | 10/2013 | Ben-Ezra et al. | |
| 8,583,238 B1 | 11/2013 | Heldman et al. | |
| 8,583,256 B2 | 11/2013 | Tracey et al. | |
| 8,612,005 B2 | 12/2013 | Rezai et al. | |
| 8,639,343 B2 | 1/2014 | De Vos | |
| 8,660,644 B2 | 2/2014 | Jaax et al. | |
| 8,688,239 B2 | 4/2014 | Hartlep et al. | |
| 8,843,210 B2 | 9/2014 | Simon et al. | |
| 8,874,219 B2 | 10/2014 | Trier et al. | |
| 8,903,494 B2 | 12/2014 | Goldwasser et al. | |
| 8,983,621 B2 | 3/2015 | Hou et al. | |
| 9,002,458 B2 | 4/2015 | Pal et al. | |
| 9,014,811 B2 | 4/2015 | Pal et al. | |
| 9,067,054 B2 | 6/2015 | Simon et al. | |
| 9,168,374 B2 | 10/2015 | Su | |
| 9,205,258 B2 | 12/2015 | Simon et al. | |
| 9,233,244 B2 | 1/2016 | Pal et al. | |
| 9,248,292 B2 | 2/2016 | Trier et al. | |
| 9,333,334 B2 | 5/2016 | Jeffery et al. | |
| 9,364,674 B2 | 6/2016 | Cook et al. | |
| 9,393,401 B2 | 7/2016 | Goldwasser et al. | |
| 9,393,430 B2 | 7/2016 | Demers et al. | |
| 9,415,219 B2 | 8/2016 | Simon et al. | |
| 9,446,242 B2 | 9/2016 | Griffith | |
| 9,474,905 B2 | 10/2016 | Doan et al. | |
| 9,655,772 B2 | 5/2017 | Smith et al. | |
| 9,656,076 B2 | 5/2017 | Trier et al. | |
| 9,700,725 B2 | 7/2017 | Zhu | |
| 9,731,116 B2 | 8/2017 | Chen | |
| 9,744,347 B2 | 8/2017 | Chen et al. | |
| 9,764,133 B2 | 9/2017 | Thomas et al. | |
| 9,782,587 B2 | 10/2017 | Trier et al. | |
| 2001/0000187 A1 | 4/2001 | Peckham et al. | |
| 2002/0116036 A1 | 8/2002 | Daignault et al. | |
| 2003/0088279 A1 | 5/2003 | Rissmann et al. | |
| 2003/0134545 A1 | 7/2003 | McAdams et al. | |
| 2003/0171685 A1 | 9/2003 | Lesser et al. | |
| 2003/0225323 A1 | 12/2003 | Kiani et al. | |
| 2004/0019370 A1 | 1/2004 | Gliner et al. | |
| 2004/0098065 A1 | 5/2004 | Hagglof et al. | |
| 2004/0158305 A1 | 8/2004 | Axelgaard | |
| 2004/0267333 A1 | 12/2004 | Kronberg | |
| 2005/0165460 A1 | 7/2005 | Erfan | |
| 2005/0267388 A1 | 12/2005 | Hanna | |
| 2005/0283259 A1 | 12/2005 | Wolpow | |
| 2006/0047215 A1 | 3/2006 | Newman et al. | |
| 2006/0064139 A1 | 3/2006 | Chung et al. | |
| 2006/0149119 A1 | 7/2006 | Wang | |
| 2006/0190057 A1 | 8/2006 | Reese | |
| 2006/0195159 A1 | 8/2006 | Bradley et al. | |
| 2006/0206163 A1 | 9/2006 | Wahlstrand et al. | |
| 2006/0247985 A1 | 11/2006 | Liamos et al. | |
| 2007/0053466 A1 | 3/2007 | Klostermann | |
| 2007/0088419 A1 | 4/2007 | Fiorina et al. | |
| 2007/0097593 A1 | 5/2007 | Armstrong | |
| 2007/0100275 A1 | 5/2007 | Fischer et al. | |
| 2007/0173890 A1 | 7/2007 | Armstrong | |
| 2007/0213790 A1 | 9/2007 | Nolan et al. | |
| 2007/0276451 A1 | 11/2007 | Rigaux | |
| 2008/0015641 A1 | 1/2008 | Armstrong et al. | |
| 2008/0045882 A1 | 2/2008 | Finsterwald | |
| 2008/0071626 A1 | 3/2008 | Hill | |
| 2008/0097564 A1 | 4/2008 | Lathrop | |
| 2008/0132974 A1 | 6/2008 | Strother et al. | |
| 2008/0207985 A1 | 8/2008 | Farone | |
| 2008/0208266 A1 | 8/2008 | Lesser et al. | |
| 2008/0215113 A1 | 9/2008 | Pawlowicz | |
| 2008/0275293 A1 | 11/2008 | Lattner et al. | |
| 2008/0281368 A1 | 11/2008 | Bulkes et al. | |
| 2008/0319505 A1 | 12/2008 | Boyden et al. | |
| 2009/0048642 A1 | 2/2009 | Goroszeniuk | |
| 2009/0054952 A1 | 2/2009 | Glukhovsky et al. | |
| 2009/0099623 A1 | 4/2009 | Bentwich | |

(56) References Cited

U.S. PATENT DOCUMENTS

| | | |
|---|---|---|
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1* | 9/2014 | DiUbaldi ............ A61N 1/0472 607/139 |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0088224 A1 | 3/2015 | Goldwasser et al. |
| 2015/0224310 A1 | 8/2015 | Sharma et al. |
| 2015/0230863 A1 | 8/2015 | Youngquist et al. |
| 2015/0238762 A1 | 8/2015 | Pal et al. |
| 2015/0257970 A1 | 9/2015 | Mucke et al. |
| 2015/0328461 A1 | 11/2015 | Charlesworth et al. |
| 2015/0335877 A1 | 11/2015 | Jeffery et al. |
| 2015/0335888 A1 | 11/2015 | Demers et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2016/0317809 A1 | 11/2016 | Pal et al. |
| 2017/0076414 A1 | 3/2017 | Egnal et al. |
| 2017/0252562 A1 | 9/2017 | Goldwasser et al. |
| 2018/0036533 A1 | 2/2018 | Yoo et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 10-108913 A | 4/1998 |
| JP | 2001129100 A | 5/2001 |
| JP | 2001293097 A | 10/2001 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2009-85901 A | 4/2009 |
| JP | 2011-118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO 01/08071 A1 | 2/2001 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |

(56) References Cited

FOREIGN PATENT DOCUMENTS

| WO | WO 2012/116407 A1 | 9/2012 |
|---|---|---|
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |

OTHER PUBLICATIONS

Tyler et al.; U.S. Appl. No. 15/536,148 entitled "Methods and apparatuses for transdermal stimulation of the outer ear," filed Jun. 15, 2017.

Tyler et al.; U.S. Appl. No. 15/536,151 entitled "Systems and methods for transdermal electrical stimulation to improve sleep," filed Jun. 15, 2017.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Chaieb et al.; Transcranial alternating current stimulation in the low kHz range increases motor cortex excitability; Restor Neurol Neurosci; 29(3); pp. 167-175; Mar. 2011.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

GoFLOW; tDCS Kit; product information; 9 pgs..; printed Feb. 10, 2014 (http://flowstateengaged.com/).

Gracenote; Timeline-metadata-api; 3 pages; retrieved from the internet Jul. 7, 2015; (https://github.com/gracenote/timeline-metadata-api/blob/master/README.md).

Grindhouse Wetware; Thinking Cap; product information; 1 pg.; printed Feb. 10, 2014 (http://www.grindhousewetware.com/thinkingcap.html).

Kanai et al.; Frequency-dependent electrical stimulatioin of the visual cortex; Curr. Biol.; 18(23); pp. 1839-1843; Dec. 9, 2008.

Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

STD Pharmaceutical Products; Idrostar intophoresis machine (product and use information); 9 pgs.; Dec. 2011 (printed Feb. 11, 2014 from http://www.iontophoresis.info/instructions/).

Terney et al.; Increasing human brain excitability by transcranial high-frequency random noise stimulation; The Journal of Neuroscience; 28(52); pp. 14127-14155; Dec. 2008.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).

Tyler et al.; U.S. Appl. No. 61/550,334 entitled "Improvement of Direct Communication," filed Oct. 21, 2011.

Tyler et al.; U.S. Appl. No. 61/663,409 entitled "Device and Methods for Noninvasive Neuromodulation Using Targeted Transcranial Electrical Stimulation," filed Jun. 22, 2012.

Jeffery et al.; U.S. Appl. No. 15/169,445 entitled "Methods and apparatuses for transdermal electrical stimulation," filed May 31, 2016.

Aston-Jones et al.; An integrative theory of locus coeruleus-norepinephrine function: adaptive gain and optimal performance; Annu. Rev. Neurosci.; 28: pp. 403-450; Jul. 21, 2005.

Aston-Jones et al.; Role of locus coeruleus in attention and behavioral flexibility; Biological Psychiatry; 46(9); pp. 1309-1320; Nov. 1, 1999.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279¬291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Cook et al.; Trigeminal nerve stimulation in major depressive disorder: acute outcomes in an open pilot study; Epilepsy and Behavior; 28(2): pp. 221-226; Aug. 31, 2013.

Degiorgio et al., Trigeminal nerve stimulation for epilepsy: long-term feasibility and efficacy; Neurology; 72(10): pp. 936-938; Mar. 10, 2009.

Degiorgio et al.; Randomized controlled trial of trigeminal nerve stimulation for drug-resistant epilepsy; Neurology; 80(9); pp. 786-791; Feb. 26, 2013.

Elder et al.; The cortisol awakening response—applications and implications for sleep medicine; Sleep Medicine Reviews; 18(3): pp. 215-224; Jun. 30, 2014.

Eschenko et al.; Noradrenergic neurons of the locus coeruleus are phase locked to cortical up-down states during sleep; Cerebral Cortex; 22(2); pp. 426-435; Feb. 1, 2012.

(56) References Cited

OTHER PUBLICATIONS

Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
Golestanirad et al; Analysis of fractal electrodes for efficient neural stimulation; Frontiers in Neurengineering; 6(3); 10 pages; Jul. 2013.
Granger et al.; Salivary alpha-amylase in biobehavioral research: recent developments and applications; Annals of the New York Academy of Sciences; 1098(1); pp. 122-144; Mar. 1, 2007.
Gummadavelli et al.; Neurostimulation to improve level of consciousness in patients with epilepsy. Neurosurgical Focus; 38(6); pp. E10; (manuscript version,14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.
McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7 (6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (INS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Tyler et al.; U.S. Appl. No. 62/166,674 entitled "Systems and Methods for Suppression of Stress Responses by Transdermal Electrical Neuromodulation," filed May 26, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.

(56) References Cited

OTHER PUBLICATIONS

Voss et al.; Induction of self awareness in dreams through frontal low current stimulation of gamma activity; Nature Neuroscience; 17(6); pp. 810-812; Jun. 1, 2014.

Watson et al.; Development and validation of brief measures of positive and negative affect: the PANAS scales; Jouranl of Personality and Social Psychology; 54(6); pp. 1063-1070; Jun. 1988.

Weiss et al; Validity of Activity-Based Devices to Estimate Sleep; Journal of Clinical Sleep Medicine : 6(4); pp. 336-342; Aug. 2010.

Goldwasser et al.; U.S. Appl. No. 15/264,224 entitled "Apparatuses and methods for neuromodulation," filed Sep. 13, 2016.

Charlesworth et al.; U.S. Appl. No. 15/384,249 entitled "Apparatuses and methods for transdermal electrical stimulation of nerves to modify or induce a cognitive state," filed Dec. 19, 2017.

Jeffery; U.S. Appl. No. 15/380,028 entitled "Electrodes having surface exclusions," filed Dec. 15, 2017.

Tyler et al.; U.S. Appl. No. 15/460,138 entitled "Systems and methods for transdermal electrical stimulation to improve sleep," filed Mar. 15, 2017.

Goldwasser et al.; U.S. Appl. No. 15/967,576 entitled "Transdermal electrical stimulation at the neck," filed Apr. 30, 2018.

\* cited by examiner

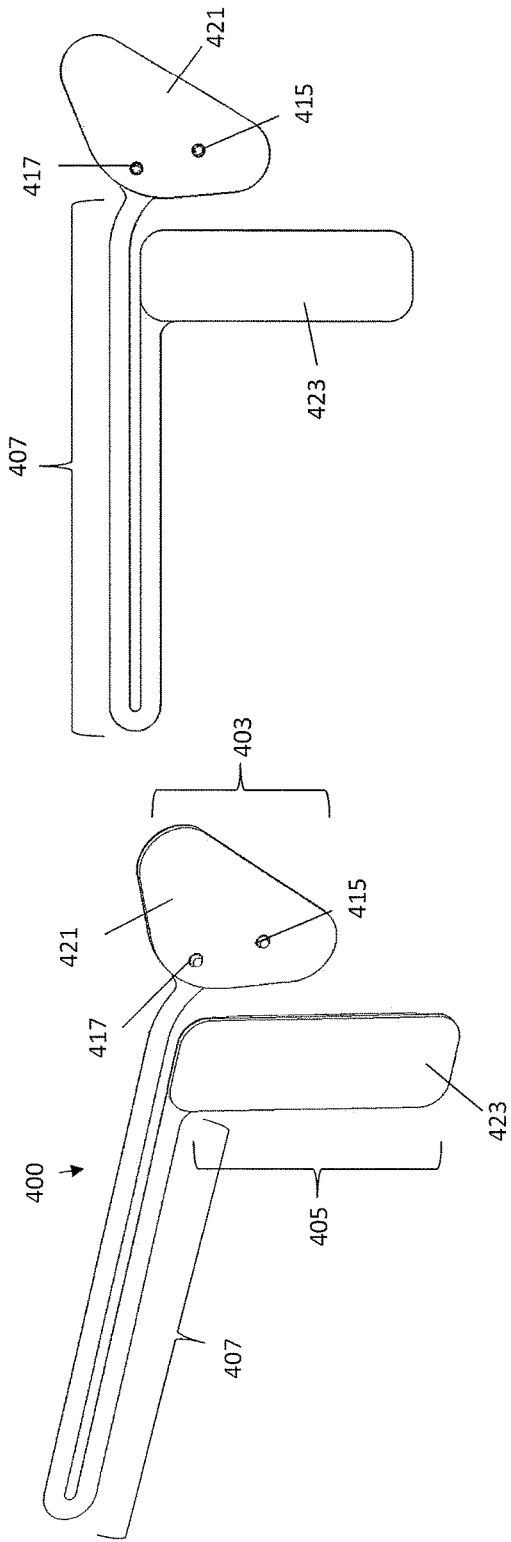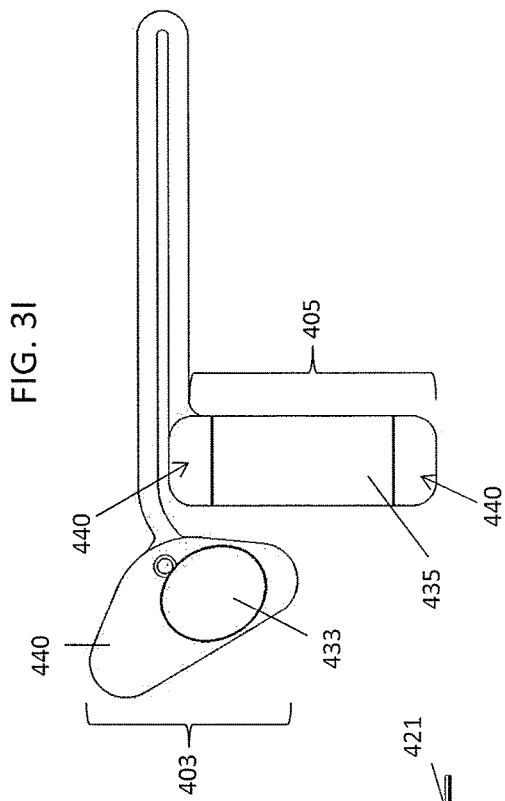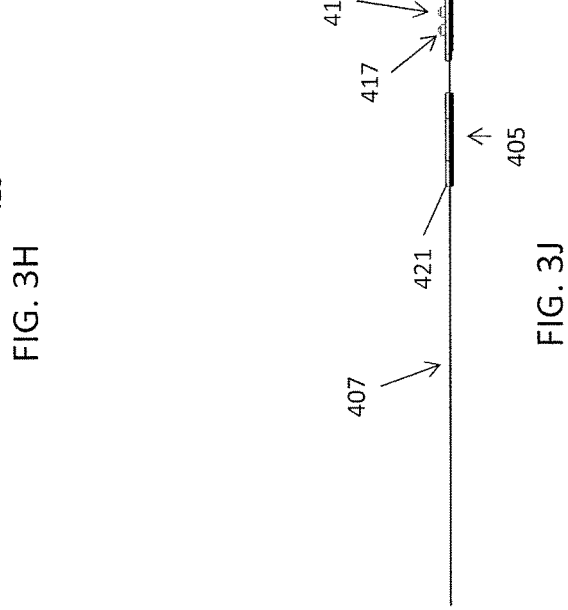

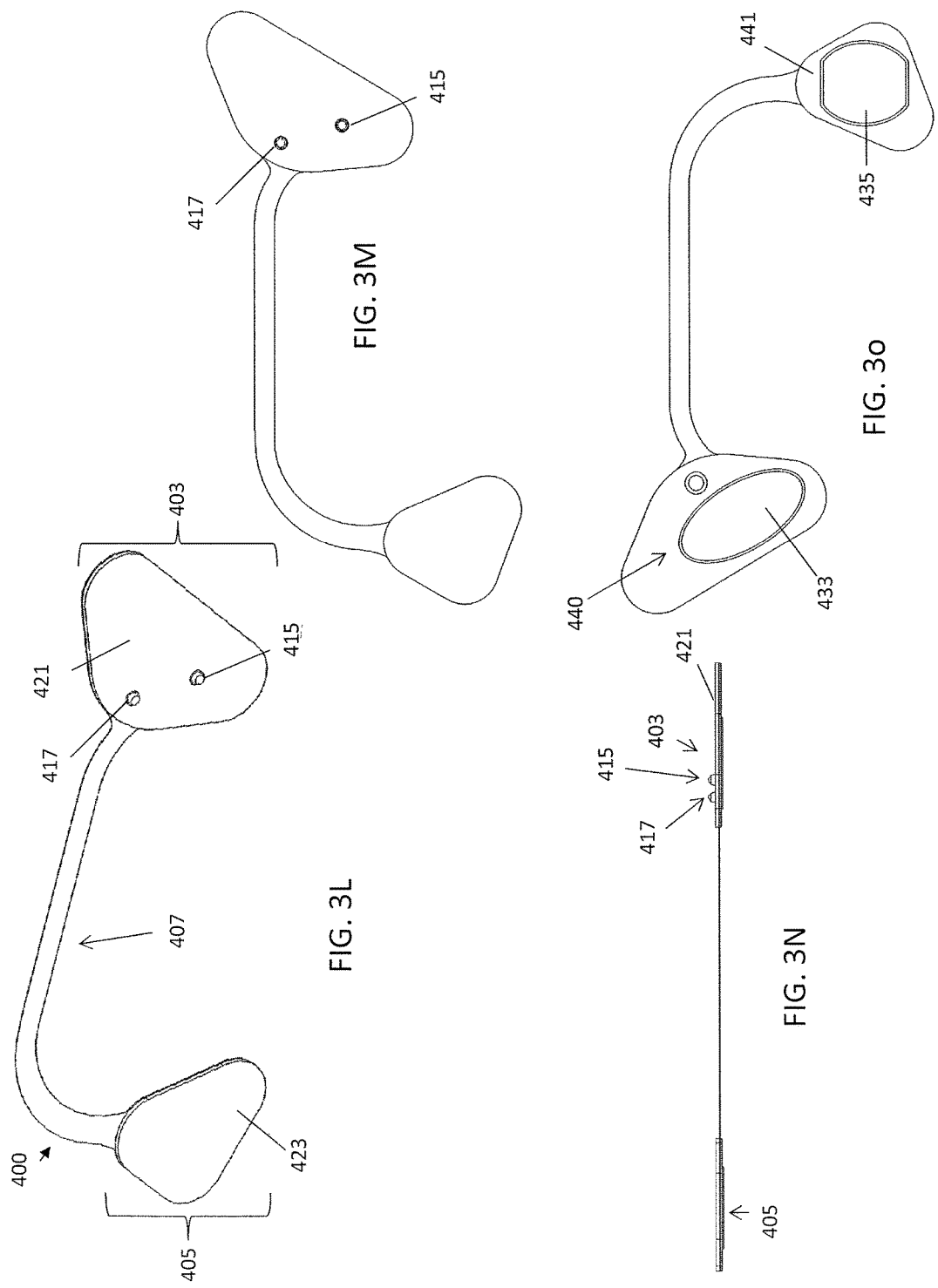

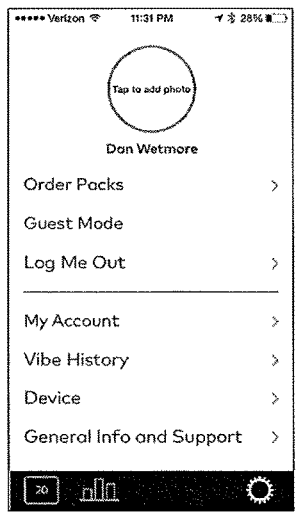
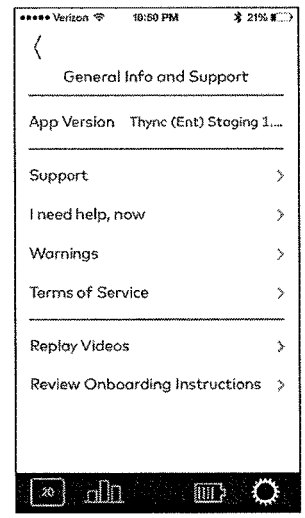
FIG. 13A    FIG. 13B    FIG. 13C
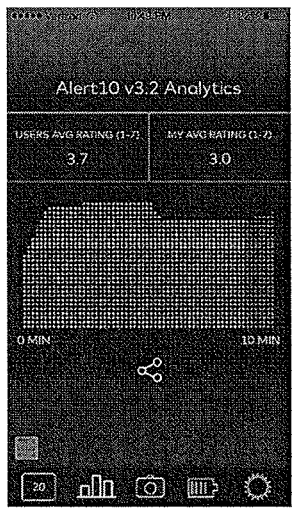
FIG. 13D    FIG. 13E

Before You Get Started, Please Read the Following Warnings

Do not use this device if you have a cardiac pacemaker, implanted defibrillator, or other implanted metallic or electronic device. Doing so could cause electric shock, burns, electrical interference or death.

Do not use during pregnancy or if you are breastfeeding. If you are in the care of a physician, consult your physician before using this device.

Do not use this device if you have epilepsy or a history of seizures.

Do not use this device if you have a Temporomandibular Joint Disorder, Bell's Palsy, impaired cranial nerve function, or facial pain.

Do not place Thync Strips on body in locations other than those directed.

Do not use this device while driving, operating machinery, or during any activity in which electrical stimulation can put you at risk for injury.

Do not use the device while in a shower, bath, pool, or other body of water.

Do not place Thync Strips over open wounds, sores or rashes, or over swollen, red, infected, or inflamed areas or skin eruptions. If you experience an adverse reaction, discontinue use.

Do not use device if the housing has been damaged.

Do not use device in the presence of strong electromagnetic fields.

Do not use this device on children under the age of 18.

Do not place this device across your chest. The introduction of an electrical current to the chest may cause rhythm disturbances to your heart, which could be lethal.

Do not place device over the carotid sinus nerves, the front of the neck, or around the mouth.

For more information and assistance with the contents of this document or the use of your Thync module, please contact: Support@Thync.com. Additional precautions and warnings are listed on page 38.

2 / Stick
Placement and Fit
Calm

 

Module Placement
Position the Thync Module on your right temple/forehead area above your right eyebrow as shown.

Press firmly for several seconds to STICK the Module on your forehead. Please ENSURE that the Thync Strip and module fit FLUSH where applied. Poor points of contact can lead to discomfort during Vibes.

Calm Strip Placement
Position the backend of the Calm Strip horizontally and centered on the back of your neck just below your hairline.

Press firmly for several seconds to STICK the B end of the Thync Calm Strip in the specified position to ensure a good connection.

Note: Thync Module and Strips may not adhere properly if excessive oils, lotions, makeup or sunscreens are used, resulting in less effective results and possible discomfort.

FIG. 14N

Important Information

Usage

The intended use of the Thync System is to deliver pulsed neurostimulation waveforms to modulate psychophysiological arousal for lifestyle or wellness applications.

The Thync System is not intended to treat or diagnose any disease or medical condition. For detailed usage instructions and warnings, please consult: Thync.com

Disclaimer

Thync does not approve or endorse any changes or modifications to this system, which may alter its performance characteristics. Any such changes void warranty and authority for use.

Adverse Reactions

If you experience adverse reactions, stop using the system and consult with your physician. Users with sensitive skin may experience skin irritation in the area where the Thync Strip is applied. You may experience a headache and other painful sensations during or following the application of electrical stimulation.

32

Precautions

Use caution if Thync Strip is placed over areas of skin that lack normal sensation.

Clean and dry the area of skin to which the Thync Strip will be applied before applying it.

Use of accessories not approved by the manufacturer may cause harm or injury.

Do not disassemble the Module.

Thync Strips should only be applied to normal, intact, healthy skin over locations as directed.

Keep dry. Clean by wiping with dry cloth. Do not immerse.

Operation in close proximity to short wave or microwave therapy equipment may produce instability in the Module output.

Keep this system out of reach of children.

FIG. 14Q

How do
Vibes feel?

It's similar to the relaxing sensation of a massage or the invigoration of splashing cold water on your face - only more focused.

How does it feel to relax and get a good night's sleep? What is it like to feel motivated and make it to the gym every day? That's how good feels. That's what Vibes do for you.

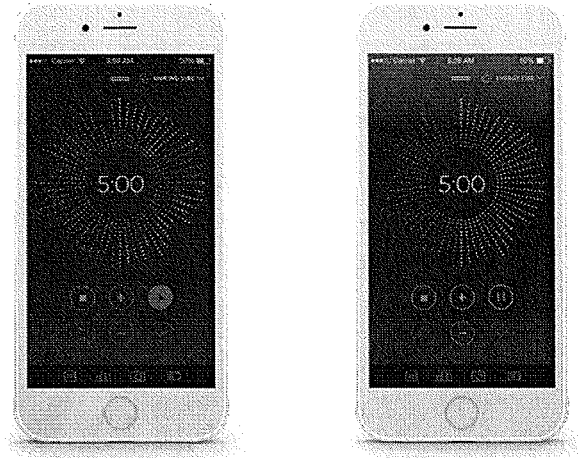

FIG. 17C

How to Vibe

Vibing is easy.
Just 3 steps - Snap, Stick, Shift.

For some users, Vibe effects are immediate and obvious. Others may require multiple Vibes or need to try various placement and tuner settings to experience the desired effects.

FIG. 17D

Thync is a new category of wearable technology that acts in synergy with your mind and body.

The Thync Approach

A soothing neck massage. A splash of cold water. A kiss from someone you love. Each action influences peripheral nerves in your head and face, signaling brain regions to change the way you feel. Thync works using the same pathways by delivering low-level electrical pulses to these nerves.

Every day, your body balances the activity between your sympathetic and parasympathetic nervous systems. The sympathetic system is associated with a "fight or flight" response to help regulate your reaction to stress. The parasympathetic system counteracts stress to help you enter a relaxed "rest and digest" mode.

Thync uses neurosignaling to activate specific cranial and peripheral nerves to influence this balance and shift you to a state of calm or give you a boost of energy in minutes.

FIG. 18A

Neurosignaling: The Science

Neurosignaling is the coupling of an energy waveform to a neural structure (receptor, nerve or brain tissue) to modulate its activity.

Neurosignaling waveforms or Vibes consist of precise algorithms that bias activity of the sympathetic and parasympathetic nervous systems, so that you can enjoy a shift into a more energetic or relaxed state.

Neurosignaling builds upon the best features of long-standing tDCS and TENS techniques by using pulsed currents with lower-intensity and higher-frequency outputs delivered through bio-compatible materials for greater safety and comfort.

At Thync, we have developed proprietary neurosignaling technology that delivers signals to the brain through three neural pathways:

FIG. 18B

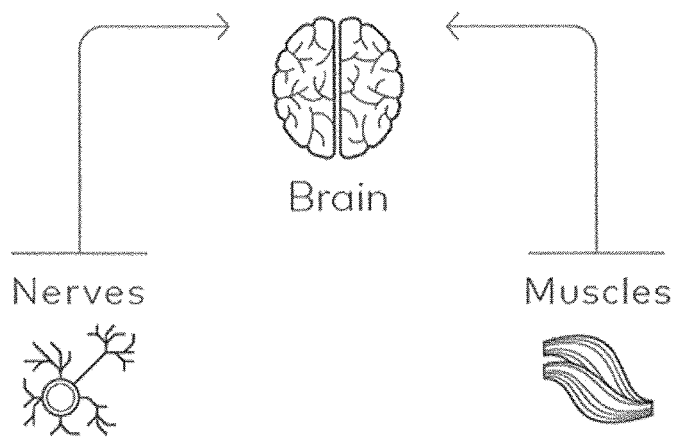

FIG. 18C

Thync System: The Technology

The Thync System is an integrated set of components innovatively designed to deliver neurosignaling Vibes. Following years of development, engineering and testing, the Thync System is uniquely designed to fit into active lifestyles.

The Thync Module and Strips represent groundbreaking advances in technology. From the elegant curved design and fit of the lightweight Module, to the bio-materials used in Thync Strips, to the simplicity of the App, the System is designed to be easy, comfortable and effective in a variety of lifestyle applications.

The Thync System

FIG. 18D

Safety

Thync is the result of years of research and development by Thync neuroscientists and engineers. Thync Vibes were safely tested on several thousand individuals under a variety of conditions to optimize their performance and comfort.

The Thync System builds upon more than 40 years of extensive research, documentation and consumer use that supports the safety and tolerability of our limited output neurosignaling approach.

The Thync System is a low-risk transdermal neurostimulation device intended for lifestyle use at home, work, or in wellness applications to temporarily induce mental relaxation or calmness or to temporarily increase energy, awareness, and alertness. The Thync system is a safe and low-risk device. It is not intended to treat or diagnose any disease or medical condition.

Based on intended use and output characteristics, the FDA notified Thync that its device is not subject to medical device regulations requiring pre-market clearance or approval.

Safety Study — PDF

FIG. 18E

Testing

Thync Vibes are the culmination of testing on thousands of subjects conducted internally by our scientists, externally through our university collaborators, and by our early adopters in the real world. We capture, record, and analyze data such as heart rate, heart rate variability, galvanic skin response, pupil diameter, and EEG to quantify how Vibes influence the parasympathetic and sympathetic nervous systems. We monitor biometric signals, assay psychophysiological variables, and conduct psychometric evaluations.

We have developed a technology that can consistently, and in a statistically reliable manner, beat the placebo effect. Our studies incorporate the use of placebo controls in blind tests under a variety of experimental conditions. All studies are performed using IRB-approved protocols and procedures.

Neurosignaling Study — PDF

FIG. 18F

APPARATUSES AND METHODS FOR NEUROMODULATION

CROSS REFERENCE TO RELATED APPLICATIONS

This patent application claims priority to each of the following: U.S. Provisional Patent Application No. 62/169,522, filed on Jun. 1, 2015, and titled "SYSTEMS AND METHODS FOR NEUROMODULATION TO TRANSFORM CONCURRENT SENSORY EXPERIENCES"; U.S. Provisional Patent Application No. 62/169,523, filed on Jun. 1, 2015, and titled "APPARATUSES AND METHODS FOR NEUROMODULATION"; U.S. Provisional Patent Application No. 62/170,111, filed on Jun. 2, 2015, and titled "SYSTEMS AND METHODS NEUROMODULATION WITH FACIAL AND MASTOID ELECTRODES"; and U.S. Provisional Patent Application No. 62/268,084, filed on Dec. 16, 2015 and titled "SYSTEMS AND METHODS FOR NEUROMODULATION WITH FACIAL AND MASTOID ELECTRODES". Each of these applications is herein incorporated by reference in its entirety.

This application may also be related to one or more of: U.S. patent application Ser. No. 14/639,015, filed on Mar. 4, 2015 and titled "TRANSDERMAL ELECTRICAL STIMULATION DEVICES FOR MODIFYING OR INDUCING COGNITIVE STATE" (now U.S. Pat. No. 9,233,244); U.S. patent application Ser. No. 14/634,551, filed on Feb. 27, 2015 and titled "METHODS FOR USER CONTROL OF NEUROSTIMULATION TO MODIFY A COGNITIVE STATE"; U.S. patent application Ser. No. 14/715,461, filed on May 18, 2015 and titled "WEARABLE TRANSDERMAL NEUROSTIMULATOR"; and U.S. patent application Ser. No. 14/715,476, filed on May 18, 2015 and titled "METHODS AND APPARATUSES FOR AMPLITUDE-MODULATED ENSEMBLE WAVEFORMS FOR NEUROSTIMULATION". Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein relate to transdermal electrical neuromodulation. In particular described herein are wearable neurostimulator apparatuses configured to deliver electrical stimulation waveforms for inducing a change in cognitive state, delivered concurrently with other sensory experiences so that the cognitive effects of the sensory experience (primary sensory effects, as well as secondary and higher order sensory-driven cognitive effects, including emotion, arousal, mood, etc.) are enhanced, mitigated, or otherwise modulated by the sensory and cognitive effects of electrical stimulation.

The methods and apparatuses described herein relate to transdermal electrical neuromodulation. In particular described herein are wearable neurostimulator apparatuses configured to deliver electrical stimulation waveforms for inducing a change in cognitive state using two or more electrodes placed on the face and/or mastoid(s).

BACKGROUND

Noninvasive neuromodulation technologies that affect neuronal activity can modulate neural activity and potentially alter behavior, cognitive states, perception, and motor output without requiring an invasive procedure. The induced neuromodulation occurs in the context of a subject's ongoing sensory experiences and endogenous cognitive state, yet, to date, noninvasive neuromodulation technologies have not been configured to integrate or coordinate with the subject's sensory experiences and cognitive state to create new and more effective forms of neuromodulation.

For example, transcranial/transdermal electric stimulation (hereinafter "TES") using scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel, U.S. Pat. No. 4,646,744; Haimovich et al., U.S. Pat. No. 5,540,736; Besio et al., U.S. Pat. No. 8,190,248; Hagedorn and Thompson, U.S. Pat. No. 8,239,030; Bikson et al., U.S. Patent Application Publication No. 2011/0144716; and Lebedev et al., U.S. Patent Application Publication No. 2009/0177243). tDCS systems with numerous electrodes and a high level of configurability have been disclosed (see for example Bikson et al., U.S. Patent Application Publication Nos. 2012/0209346, 2012/0265261, and 2012/0245653).

TES devices have historically been used therapeutically in clinical applications, including treatment of pain, depression, epilepsy, and tinnitus. "Lifestyle" applications of neuromodulation have been proposed, including those for affecting states of calmness and energy, but these neuromodulation systems and methods are lacking in at least some instances because they are not well integrated and coordinated with the cognitive effects induced by other sensory experiences such as music, film or video, and other olfactory, gustatory, vestibular, and somatosensory sensory experiences and related cognitive effects. Thus, the cognitive effects induced by TES are limited and lacking in at least some instances.

Despite the research to date on noninvasive neuromodulation, existing systems and methods for noninvasive neuromodulation, including TES, are lacking in at least some cases for enhancing the experience of a musical event or other individual or group experience by inducing a cognitive state that modifies the experience of the event or other experience in a positive or beneficial manner. Systems and methods for integrating noninvasive neuromodulation such as (but not limited to) TES with a musical event (e.g. concert or DJ set at a club), musical track (e.g. listened to by oneself), or other sensory experiences (e.g. video or film) would be advantageous.

Despite advances in the creation and management of multi-sensory experiences associated with performances and other forms of produced art (i.e. a recorded audio track or video), methods to modulate the subjective experience of an audience are lacking in at least some instances for enhancing the experience of a musical event or other individual or group experience by inducing a cognitive state that modifies the experience of the event or other individual or group experience in a positive or beneficial manner. Moreover, systems and methods for integrating TES with a musical event (e.g. concert or DJ set at a club) or other group experience would be advantageous.

To date, the majority of transdermal non-invasive neuromodulatory devices apply electrical energy to a subject's skin using one or more electrodes that typically attach to the neurostimulator via a cord or cable, which can be long and awkward to wear, particularly in a non-clinical or non-research setting.

TES has been used therapeutically in various clinical applications, including treatment of pain, depression, epilepsy, and tinnitus. Despite the research to date on TES neuromodulation, existing systems and methods for delivering TES are lacking. In particular, neurostimulators that are effective, comfortable and easy-to-use, e.g., easy to apply and remove, particularly in a non-clinical (e.g., home) setting, have been lacking.

Although a handful of small, lightweight and presumably wearable neuromodulation devices have been described, none of these systems are adapted for use with electrodes (e.g., disposable electrode assemblies) for applying energy to a user's head. In particular, none of these systems may be secured to a separate electrode assembly so that the neurostimulator may be well-secured to the user's head (or other body region) for a variety of sizes of users. For example, previously described neurostimulators either attach directly to the user (e.g., adhesively, and must therefore rest directly against the user's body) or they are secured to an electrode which is secured to the body but requires additional support (e.g., from a strap or additional adhesive on the neurostimulator) to be worn by the subject.

Thus, there is a need for lightweight, wearable neuromodulation devices (e.g., neurostimulators) that may be securely worn by the user by attachment through a separate electrode assembly. Furthermore, there is a need for lightweight neurostimulators that mechanically and electrically secure to an electrode assembly in a manner that fits a variety of body shapes and sizes. In particular, there is a need for wearable neurostimulators that are configured to be comfortably wearable and will not fall off when a user is moving around, or even when a user is wearing additional clothing or glasses. Described herein are methods and apparatuses (e.g., devices and systems, and methods of operating such apparatuses) that may address at least the needs identified above.

In addition, the cognitive effects induced by existing TES are also limited and lacking in at least some instances in terms of the effects induced and the simplicity and possibilities for miniaturization of a wearable TES neurostimulator system with electrodes targeting the face and/or mastoid(s).

SUMMARY OF THE DISCLOSURE

Described herein are methods and apparatuses for pairing and coordinating one or more non-invasive transdermal stimulation with an audiovisual (e.g., musical, video, etc.) composition. Any appropriate modality of non-invasive transdermal (and/or transcranial) stimulation may be used, particularly those that apply energy to one or more brain regions to induce a cognitive state by actively or passively stimulating and/or inhibiting activity (e.g., neuronal activity). Examples of such transdermal stimulation modalities include transdermal electrical stimulation (TES, TDCS, etc.), ultrasound (e.g., transcranial ultrasound stimulation), transcranial magnetic stimulation (TMS), and transcranial phototherapy (transcranial phototransduction, etc.), or combinations and variations thereof. Although the examples provided herein are focused on and exemplify transdermal electrical stimulation (TES) methods and apparatuses, the principles describe herein may be applied to any of these other energy modalities as well.

For example, embodiments of the present invention provide improved systems and methods for transdermal electrical stimulation (hereinafter "TES", and including transdermal electrical stimulation) and other modalities of noninvasive energy delivery to the brain in order to induce neuromodulation and overcome at least some of the deficiencies of prior systems and methods. The systems and methods described herein include systems for associating music, video, and/or other sensory experiences with neuromodulation. By appropriately pairing a neuromodulation stimulation regime with appropriate music, video, and/or other temporally structured sensory experiences, a more significant cognitive effect can be induced in a subject than by either neuromodulation or sensory experience (e.g. music) alone.

Embodiments of the present invention provide improved systems and methods for transdermal electrical stimulation to induce neuromodulation and overcome at least some of the deficiencies of prior systems and methods. The systems and methods described herein include systems for inducing cognitive effects using electrodes that are closely spaced on the face or low profile (small and hidden) on the mastoid behind the ear, unilaterally or bilaterally. The new form factors of TES neurostimulator systems (and electrode assemblies associated with a TES neurostimulator system) represent advances on the state of the art for wearable, portable, and, optionally, disposable systems for TES.

Described herein are methods of applying transdermal electrical stimulation (TES) to a subject to enhance a concurrent sensory experience. The sensory experience may be auditory (e.g., heard, including music, spoken word, etc.), visual (e.g., seen, including cinematic, animated, discrete images, etc.), audiovisual (movies, live performances, 3D or virtual reality, etc.), tactile (e.g., felt, including amusement rides, etc.). Changes in the sensory experience may be correlated with changes in the applied TES waveforms, as described herein. For example, a transitions in the music (e.g., changes in tempo, key, pitch, timbre, instrumentation, musical key, loudness, sharpness, changes to different musical pieces, etc.), may be correlated with a change in the applied TES waveform parameter (e.g., current amplitude, frequency, DC offset, percent duty cycle, percent charge imbalance, amplitude modulation (on/off, change in amplitude modulation frequency, envelope, etc.). The sensory experience (e.g., performance) may be prerecorded and may include markers to trigger changes in the TES waveform parameters, or the apparatus (e.g., TES applicator or a controller associated with one or more TES applicators) may analyze the performance to detect changes in the sensor experience and select the change in the TES waveform applied. The type of change in the TES waveform may correlate with the type of change in the sensory experience. For example, an increase in tempo, pitch, etc. may increase the intensity of the TES signal (current and/or frequency), particularly when applying waveforms using an "energy" configuration that enhances alertness, etc. Although musical performance are described, other sensory performance, such as audiovisual performances that include visual transitions (e.g., changes in lighting, rate of motion of object's being visualized, etc.) may also or alternatively be correlated with TES waveform parameters. Similarly, a tactile experience such an amusement park ride or VR experience may also include features (lighting, rate of motion, vibration, etc.) that may be correlated with TES waveform parameters.

For example, methods of applying transdermal electrical stimulation (TES) to a subject to enhance a concurrent sensory experience, by applying the TES to the subject (including but not limited to the subject's head or head and neck from two or more electrodes that are coupled to a neurostimulator) may include: applying an ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more waveform descriptor; further wherein transitions between the component waveforms temporally correlates with transitions in the sensory experience.

The one or more waveform descriptor may be selected from the group consisting of: current amplitude, frequency, percent charge imbalance or percent duty cycle, capacitive discharge pulsing, amplitude modulation, etc.

The method may generally be remotely triggered (e.g., by a server or processor that is remote to the user but communicating with the TES applicator) or by the TES applicator being worn by the subject. The sensory experience may be prerecorded (e.g., music, video, etc.) and may include markers that are detected by the TES applicator and/or a remote server (processor) communicating with the TES applicator to trigger the change in one or more of the waveform descriptors mentioned. The markers may be generic (e.g., 'change to next sub-waveform in an ensemble waveform having one or more different waveform descriptors/characteristics) or specific (indicating which waveform characteristic/descriptor to change, such as current amplitude, frequency, etc.).

In general, these methods may include synchronizing the delivery of the sensory experience and the TES stimulation. In some variations the TES applicator and/or a remote server/processor may synchronize the two; in some variations the sensory experience (e.g., music, video, VR, etc.) is displayed to the user by the TES applicator or by a system integrating the TES applicator. For example, the method may include playing the sensory experience from the neurostimulator.

In general, the transitions between the component waveforms may temporally correlate with transitions in a musical element of the sensory experience. Thus a change in the TES waveform may be simultaneous with the transition in the sensory experience (including musical transitions), or within a few seconds or partial seconds (+/−0.1 sec, 0.2 sec, 0.3 sec, 0.4 sec, 0.5 sec, 1 sec, etc.). For example, the transition between the component waveforms may temporally correlates with transitions in one or more of: tempo, theme, genre, timbre, instrumentation, musical key, loudness, pitch level, and sharpness.

Applying the ensemble current waveform may comprise applying component waveforms that are biphasic, and may include applying a series of greater than 5 component waveforms (e.g., 5 immediacy consecutive waveforms having one or more different waveform properties). Applying the ensemble current waveform may comprise applying the series of component waveforms wherein a component waveform in the series differs from another component waveform immediately before and/or immediately after the component waveform in the series by two or more of: the current amplitude, the frequency, the percent charge imbalance, and the percent duty cycle. The TES waveform applied may transition to other waveform parameters (descriptors) at other times that are not correlated with transitions in the sensory experience and/or may only occur when correlated.

Applying the ensemble current waveform may comprise sequentially applying component waveforms in the series for their duration and, during the duration of each component waveform, ramping one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

These methods may also include placing a first electrode of a portable TES applicator on the subject's skin on a temple or forehead region, and/or on a subject's temple/forehead region and on the back of the subject's neck and/or on a subject's temple/forehead region and behind the subject's ear(s). In general, the electrodes may be placed in any appropriate location on the subject ("user"). For example, placing a first electrode of a portable TES applicator on the subject's skin on a temple or forehead and placing a second electrode on the subject's skin on either the subject's mastoid region or on the subject's neck.

Applying an ensemble current waveform may comprise sequentially applying the series of component waveforms wherein the absolute value of the peak current amplitude of the component waveforms is between about 3 mA and 25 mA, wherein the frequency of the component waveforms is between about 250 Hz and 30 kHz, and/or wherein the duty cycle of the component waveforms is between about 20 and 80%. Applying an ensemble current waveform may comprises sequentially applying the series of component waveforms wherein the percent charge imbalance of component waveforms is between about 10% and 100%.

In general, a user may modify the intensity (e.g., to avoid pain and discomfort) at any time during the application of the TES. For example, a method may include modifying the ensemble waveform during application by a user intensity adjustment factor.

For example, a method of applying transdermal electrical stimulation (TES) to a subject to enhance a concurrent audio or audiovisual experience, by applying the TES to the subject's head or head and neck from two or more electrodes that are coupled to a neurostimulator, may include: synchronizing the audio or audiovisual experience with an ensemble waveform; applying the ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more of the current amplitude, the frequency, the percent charge imbalance or the percent duty cycle; further wherein transitions between the component waveforms temporally correlates with transitions in the audio or audiovisual experience.

A method of applying transdermal electrical stimulation (TES) to a subject to enhance a concurrent musical performance, by applying the TES to the subject's head or head and neck from two or more electrodes that are coupled to a neurostimulator, may include: synchronizing the musical performance with an ensemble waveform; applying the ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more of the current amplitude, the frequency, the percent charge imbalance or the percent duty cycle; further wherein transitions between the component waveforms temporally correlates with transitions in a musical element of the performance, wherein the musical element is one or more of: loudness, tempo, pitch level, sharpness, and key.

Also described herein are method of applying stimulation to evoke a cognitive effect (e.g., relaxation, energy) by applying TES to the subject's temple and a region in front of the subject's ear, and electrode apparatuses configured to apply TES in these locations.

For example, a method of applying transdermal electrical stimulation to a user to modulate the user's cognitive state using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, may include: adhesively securing the first active region of the electrode apparatus to the user's temple; bending the connecting region out of the plane; adhesively securing the second active region of the electrode apparatus to the user's cheek in front of the user's ear; and coupling a wearable electrical stimulator to a first and second connector extending proud from the first electrode portion so that the wearable electrical stimulator is worn on the user in the first location.

Although this electrode configuration and these TES applicator devices (including electrode pads/patches) may be used with the methods and apparatuses for enhancing a concurrent sensory experience, they may be used in other TES methods and with other TES applicator devices as well, and are not limited to this application.

Coupling the wearable electrical stimulator to the first and second connector extending proud from the first electrode portion may comprises snapping the wearable electrical stimulator onto the first and second connectors wherein the first and second connectors are separated from each other by a predetermined amount (e.g., between 0.5 and 1.5 inches, between 0.5 and 1.2 inches, between 0.5 and 1 inches, between 0.5 and 0.8 inches, between about 0.7 and 0.8 inches, etc.).

Coupling the wearable electrical stimulator to the first and second connector may comprise snapping the wearable electrical stimulator onto the first and second connectors. Adhesively securing the first active region may comprise attaching a hydrogel on the first active region against the user's head in the first location.

Coupling the wearable electrical stimulator may comprise connecting an underside of the wearable electrical stimulator to the first and second connectors to make an electrical contact with the wearable electrical stimulator and the first and second active regions.

Any of these methods may include applying TES waveforms to evoke a state of energy in the user.

Also described herein are methods of using this configuration. For example, a method of applying transdermal electrical stimulation to a user to modulate the user's cognitive state using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, may include: adhesively securing the first active region of the electrode apparatus to the user's cheek in front of the user's first ear; bending the connecting region out of the plane; adhesively securing the second active region of the electrode apparatus to the user's cheek in front of the user's second ear; and coupling a wearable electrical stimulator to a first and second connector extending proud from the first electrode portion so that the wearable electrical stimulator is worn on the user in the first location.

Coupling the wearable electrical stimulator to the first and second connector extending proud from the first electrode portion may comprise snapping the wearable electrical stimulator onto the first and second connectors wherein the first and second connectors are separated from each other by between a predetermined amount (e.g., between about 0.7 and 0.8 inches, etc.). Coupling the wearable electrical stimulator to the first and second connectors may comprise snapping the wearable electrical stimulator onto the first and second connectors.

Adhesively securing the first active region may comprise attaching a hydrogel on the first active region against the user's head in the first location. Coupling the wearable electrical stimulator may comprise connecting an underside of the wearable electrical stimulator to the first and second connectors to make an electrical contact with the wearable electrical stimulator and the first and second active regions. Any of these methods may be used to evoke a desired cognitive state, for example any of these methods may include applying TES waveforms to evoke a state of energy in the user.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3H-3K illustrates a first example of one variation of an electrode assembly, configured as a "calm" electrode assembly.

FIGS. 3L-3o illustrate a second example of one variation of an electrode assembly, configured as an "energy" electrode assembly.

FIGS. 13A-13E show screens of an app for controlling a neurostimulator for TES that display a settings menu; provide information and controls about a TES neurostimulator; display general information and access to support; and show analytics data about current, recent, and historical TES sessions.

FIG. 14C shows a warnings page of a user guide for a TES system.

FIGS. 14L-14N show pages of a user guide for a TES system with instructions for properly positioning a wearable TES neurostimulator (i.e. 'Module') and variations of electrode assemblies (i.e. 'Energy Strip' and 'Calm Strip').

FIGS. 14o-14Q show pages of a user guide for a TES system with instructions for controlling a wearable TES neurostimulator with the smartphone app.

FIGS. 17A-17E show resources (e.g. websites) describing TES waveforms to be delivered through a neurostimulator (also referred to as 'Vibes'), including categories of Vibes (i.e. Calm Vibes and Energy Vibes), suggested contexts for use, expected skin sensations, common cognitive effects, and basic instructions for use.

FIGS. 18A-18F show resources (e.g. websites) describing the science and technology of a TES system (i.e. a 'Thync system').

DETAILED DESCRIPTION

Figure 1:
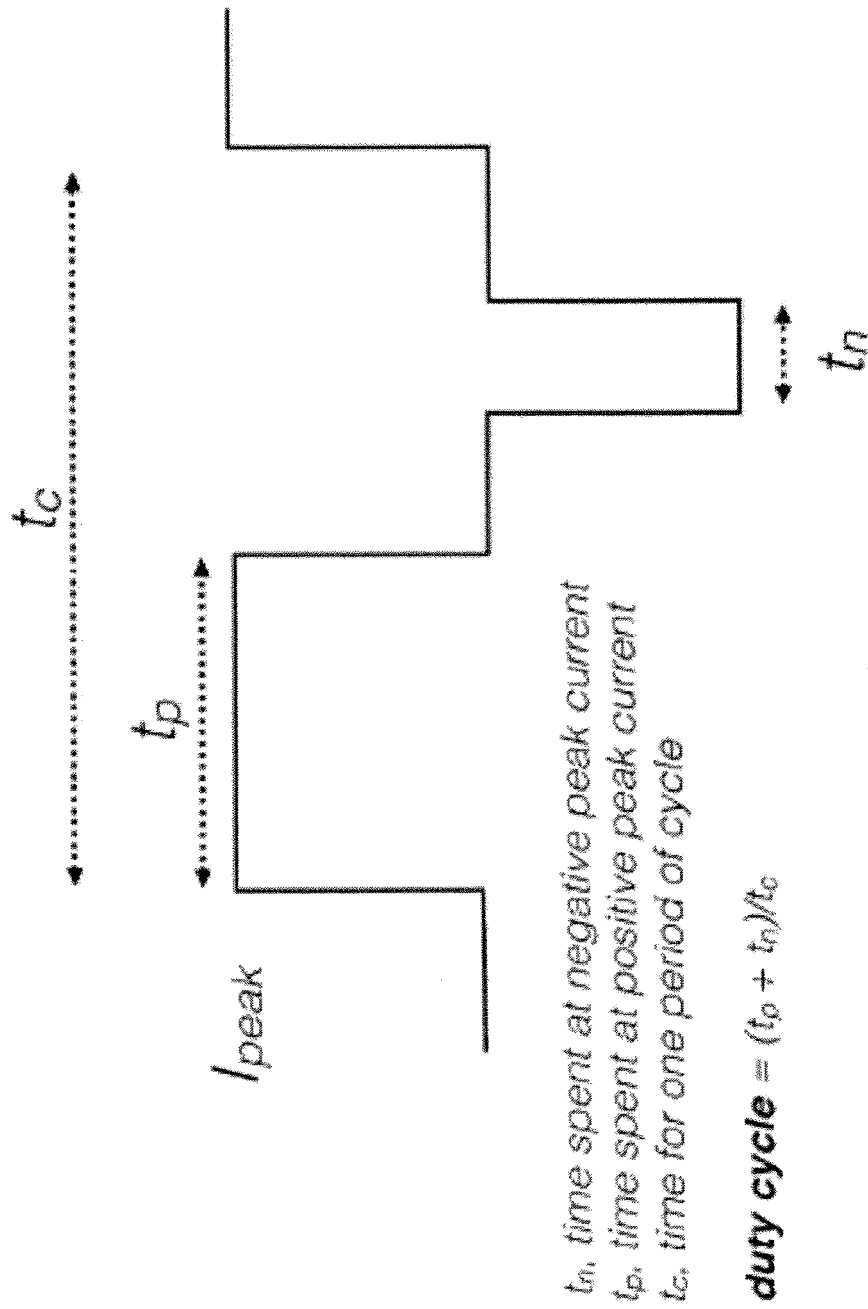
FIG. 1 schematically illustrates a base waveform which may be repeated and modified according to waveform parameters to form component waveforms which may be combined to form ensemble waveforms, as described herein, for use with TES.

Described herein are methods and apparatuses (including device and/or systems) for invoking a mental state (such as a calm, relaxed mental state or an energized mental state), or for modifying a user experience (such as enhancing a sensory experience, including audio, visual, or audiovisual experiences) by delivering transcranial/transdermal neurostimulation, e.g., transdermal electrical stimulation, hereinafter 'TES'. An enhanced sensory experience may generally be understood as sensory experiences (primary sensory effects, as well as secondary and higher order sensory-driven cognitive effects, including emotion, arousal, mood, etc.) that, when concurrently paired with an appropriate TES waveform and electrode montage (i.e. electrode size, shape, composition, and position) induce a change in cognitive state in the subject that is different than the sum of the parts (i.e. sensory experience and TES session) in quality and/or intensity. The systems (apparatuses, devices) and methods described herein may cause the cognitive effects of a subject's sensory experience to be enhanced, mitigated, or otherwise modulated.

TES may also induce sensory experiences in a subject that, though strictly speaking also cognitive effects, are generally considered to be distinct from the cognitive effects of TES such as an induction of calmness or enhanced energy. These include: skin sensations (slight pain, itchiness, prickliness, etc.), proprioception of muscles contracting, and artificial visual impulses (such as bursts of light and/or colors, e.g., phosphenes). In general, these sensory experiences of TES may also be timed with a temporally structured sensory experience, e.g. music, video, etc. to enhance the experience of the temporally structured sensory experience.

In general the apparatuses (devices, systems) and methods described herein may be used to deliver a TES waveform concurrently (and in some variations, choreographed) with music, including both recorded tracks and live performances (including in-person and streaming, e.g. Coachella via YouTube™). TES electrodes for TES sessions delivered concurrently with music are placed on the head and/or neck to elicit a cognitive effect and the neurostimulator for delivering TES may further comprise speakers (e.g. headphones or earbuds) so that a musical track may be delivered directly from the neurostimulator. In other variations, an image of a video may be delivered by a component of the neurostimulator. Alternatively, a user computing device (e.g. smartphone) may trigger or control (e.g. by Bluetooth or via a wired connection) the neurostimulator and also deliver a temporally aligned audio signal via a plug of the user computing device (e.g. headphone jack) and, optionally, video via a smartphone. In variations, the neurostimulator may fit on or in one or both ears and apply transdermal electrical stimulation targeting the cranial and/or cervical spinal nerves present in the pinna(e). Any of the neurostimulator devices described herein, including pinna neurostimulators, may include a speaker for easily delivering auditory stimuli concurrently with TES. For example, an earbud style form factor may fit in the auditory canal for delivering sound and have an assembly that press fits into the concha with stimulation electrode(s), or any other wearable neurostimulator as described herein.

Temporally structured sensory experiences are defined as generally predictable and repeatable in their timing, making them amenable to pairing with an ensemble TES waveform that itself has an ordered temporal structure of waveform components. Temporally structured sensory experiences are beneficial for coordination with a TES session. The time course of such sensory experiences may be more easily and more reliably associated with the cognitive effects of a TES session and thus more strongly and reliably enhance the combined effect of TES and the sensory experience or create a novel cognitive effect through their combination. As described in greater detail below and in specific examples herein, examples of temporally structured and/or predictable sensory experiences include music (e.g. concerts, auditory tracks on a portable music player, a DJ at a club), naturalistic sounds (e.g. waves on the beach; birds chirping; a car accelerating and shifting gears), performances involving spoken word (e.g. a play, public reading of a poem or other text, political stump speech), an event (e.g. fireworks show, light show), a video (e.g. film, TV show, movie, YouTube™ clip), a primarily visual art presentation (e.g. dance performance, visual art display, fashion show), a predictable vestibular experience (e.g. a somersault or other acrobatics by the subject, a rollercoaster, a train or subway taking a regular path), or a pattern of somatosensory activation (e.g. from a massage chair, haptic transducer array, or refreshable braille display).

According to an embodiment of the invention, a 'track' of neuromodulation is aligned (or choreographed) temporally with a sensory (or multisensory) experience experienced subjectively by a user via one or more sensory transduction pathways. As mentioned above, transdermal electrical stimulation targeting the nervous system and transcranial ultrasound neuromodulation are two forms of neuromodulation effective for a neuromodulation track, but other forms of neuromodulation can also be used, including but not limited to: transcranial magnetic stimulation (TMS), transcranial direct current stimulation (tDCS), transcranial alternating current stimulation (tACS), targeted electrical stimulation (TES), deep brain stimulation (DBS), stimulation through one electrode or an array of electrodes implanted on the surface of the brain or dura, and light activation of specially engineered proteins for neuromodulation known as optogenetics. In an exemplar embodiment, a temporal pattern of neuromodulation is combined with a musical performance or presentation. In variations, visual, tactile, olfactory, vestibular and/or gustatory stimuli are aligned temporally with neuromodulation to induce changes in cognitive function or cognitive state not possible with neuromodulation or sensory input alone.

A skilled technician can create a neuromodulation track aligned to other sensory stimuli, much as a sound engineer in a studio or lighting control person at performance do for auditory and visual stimuli. At its core, this embodiment combines raw sensory stimuli (sound, light, etc.) with neuromodulation to create contextually relevant subjective experiences that represent nonlinear responses to sound, music, film, video, performance, dance, other produced/organized sensory experiences. Artists, producers, and audience members seek further ways to control the subjective experiences associated with artistic performance in the fields of music, film, and other forms of performance art. The systems and methods described herein are designed to create new and subjectively enjoyable experiences by concurrently stimulating the brain via direct neuromodulation as well as one or more sensory transduction pathway.

One embodiment of a 'neuromodulation track' combines time varying neuromodulation with time varying sensory input in order to create enhanced experience of music for instance by making the emotional connection of music more intense or making the experience of a musical event more memorable. A musical, light show, or other sensory experience is intended to induce a particular change in cognitive state (e.g. emotional response; mood, relaxed/euphoric state; energized state).

The timescale of changes in cognitive state by a particular form of neuromodulation is an important parameter because it determines how quickly neuromodulation parameters can change relative to changing elements of other sensory inputs (e.g. musical features; lighting show effects). In some embodiments, neuromodulation occurs over a slower timescale and changing sensory inputs via traditional sensory transduction pathways occurs over a faster timescale in parallel.

In some embodiments, a particular neuromodulation protocol (and resulting change in cognitive state) is the starting point, and musical, lighting, or other sensory inputs are designed to complement the experience of (and time course of) the induced neuromodulation. Alternatively, a particular sensory experience (e.g. album, song, or symphony) may be a starting point for an artist and a neuromodulation track is designed to fit the flow of the (for instance) music.

In some embodiments, musical elements are algorithmically assessed for likely emotional states induced and neuromodulation protocols (and thus effects) are selected to be matched to a musical element or song. For instance, a transdermal electrical stimulation waveform can be offered as a complement to a song downloaded electronically, much as a music video for that song is complementary to the auditory experience and offers a different type of experience for a user or customer.

In another variation of the invention, kits are provided to designers of neuromodulation tracks so that they can experience subjectively the core neuromodulatory elements (with regards to subjective or other cognitive effects induced) and thus estimate the form of neuromodulation expected for a given temporal sequence of neuromodulation track elements.

A software or other system can complement the kit by indicating when a particular sequence of effects is impossible, unsafe, or likely to be uncomfortable.

The systems and methods described herein include systems for associating music, video, and other sensory experiences with neuromodulation. By appropriately pairing a neuromodulation stimulation regime with appropriate music, video, and other sensory experiences, a more significant cognitive effect can be induced in a subject than by either neuromodulation or sensory experience (i.e. music) alone.

In general, a system for concurrently inducing cognitive effects from a temporally structured sensory experience and a TES session may trigger a TES waveform and the temporally structured sensory experience concurrently or about at the same time. In variations, a single controller controls the TES waveform delivered via dermal electrodes and generates the sensory experience (e.g. a video on a screen of the controller or an audio signal provided via a speaker (e.g. headphones)). A portable or wearable user computing device (e.g. smartphone, smartwatch, tablet, virtual reality headset) may control a neurostimulator device for delivering TES and also generate, control, or cause to be generated (i.e. by triggering a third device) the temporally structured sensory experience (e.g. sound from the audio jack; video on the screen of the smartphone; tactile sensations from a haptic array). See, e.g., U.S. Provisional Patent Application No. 62/168,615, filed on May 29, 2015 titled "METHODS AND APPARATUSES FOR TRANSDERMAL ELECTRICAL STIMULATION".

Alternatively, alignment of music or another temporally structured form of sensory experience may enforce a delay in either a neuromodulation protocol or the music experienced by a subject. Systems and methods for enforcing a delay in neuromodulation can also apply to other forms of sensory experience such as a movie or video. Enforcing a delay on the temporally structured sensory experience (e.g. music or movie) may permit a user to start a combined TES—sensory experience (e.g. song) session with a single user input (e.g. on a user computing device controlling a neurostimulator and playing a song) and automatically delaying the onset of the temporally structured sensory experience (e.g. song) so that the cognitive effects of TES (which may have slower onset on the tens of seconds to minutes to timescale) have an onset closer in time to the onset of the song, video, etc.

Transdermal electrical stimulation, including transcranial electrical stimulation, is one form of neuromodulation for which combination with music or another form of sensory stimulation is beneficial, though other forms of neuromodulation are also beneficial including, but not limited to: transcranial pulsed low frequency ultrasound neuromodulation, transcranial magnetic stimulation, and other forms of (generally noninvasive) neuromodulation.

Improved cognitive effects can be achieved in a subject when there is a correspondence between a particular musical element and a particular neuromodulation element or event. For instance, music generally associated with a state of high energy (i.e. high tempo music or electronic dance music (EDM)) would complement and improve effects of a form of neuromodulation that causes an increase in a user's subjective feeling of energy. Associations may be personalized for a particular user to associate songs, musical elements, or genres that most effectively complement the subjective effect of a neuromodulation event or experience. Alternatively, associations between music and a form of neuromodulation may be selected according to a user's demographic profile, psychographic profile, age, gender, physiological recording, brain recording, etc.

To achieve effective match of a form of neuromodulation (e.g. one or more targets, modalities, stimulation protocols, and induced cognitive effect(s)), systems and methods for tagging, marking, or otherwise curating matched sets (e.g. pairs) of music with a form of neuromodulation and a cognitive effect induced. Elements of this system include systems and methods for building databases and distributing these matched sets (i.e. via an API).

Statistical analysis of music or other forms of sensory experience can automatically derive moods, cognitive effects, or states of mind associated with features of a piece or element of music and automatically select or suggest a matched neuromodulation protocol (one or more of target, modality, protocol, etc.). For example, as described at https://github.com/gracenote/timeline-metadata-api/blob/master/README.md (accessed on Nov. 5, 2014) "Gracenote's Timeline Metadata API gives developers access to detailed information about a track. The API currently returns four types of features for an uploaded track: beats, BPM, segments and moods." These data can be used to select an appropriate neuromodulation protocol from a database that includes metadata for induced cognitive effects and/or musical elements that have been positively associated with the neuromodulation protocol or element by a user.

A structured database containing elements of neuromodulation (including but not limited to: modality, target, intensity, and protocol) with associated performance elements, including musical elements (e.g., tempo, genre, musical key, etc.) that has been built manually, by user input (i.e. by users of a neuromodulation system) is beneficial for selecting an appropriate neuromodulation protocol, target, and/or modality based on a user's current and desired state of mind, as well as the context (i.e. music being played) for that user. A change in one or more waveform parameter that defines a shift from one block of a TES ensemble waveform to a subsequent block of a TES ensemble may be timed to occur synchronously or at a defined latency relative to a change in an auditory sensory experience (e.g. musical track), including but not limited to: a change in the frequency distribution, musical phrasing, timing of instruments and vocals, instrumentation, tempo, tonality, musical key, loudness, or directionality (i.e. from stereo or 3D speakers). In some embodiments, a band, musician, DJ, or other artist defines an element of neuromodulation (i.e. target, protocol, modality, intended cognitive effect) to associate with a musical track or other generated sensory experience.

Also described herein are methods of generating TES waveforms for concurrent delivery with a temporally structured sensory experience. For example, methods for generating TES waveforms designed to align with temporally structured experienced (i.e. a song, video, rollercoaster ride, etc.) include manual and/or computer-aided methods. For example, a practitioner of TES waveform design may use an interface on a computing device similar to common video or music editing software, wherein the waveform parameters are aligned in time with the music or video as one or more 'tracks'. The TES waveform parameters may be displayed visually for the waveform designer, as rows in the editing software, similar to how a different musical instrument is represented as a distinct class, separated visually (i.e. in its own row) in common music editing software. For example, one 'track' (or row in a TES waveform editing user interface) may represent a specific waveform parameter (i.e. a frequency, a duty cycle, a charge imbalance, the presence or absence of a capacitive discharge pulse, a bursting frequency, a bursting duty cycle, etc.). Alternatively, a TES waveform row may indicate with blocks (i.e. rectangles distinguished by color, shading, etc.) epochs of an ensemble waveform comprising different sets of waveform parameters, while another track (i.e. row) shows the ramping between (and/or within) blocks, and a third track (i.e. row) shows add-in effects such as eliciting visually perceived bursts of light and/or color (e.g., phosphenes).

Methods for generating TES waveforms designed to align with temporally structured experiences (i.e. a song, video, rollercoaster ride, etc.) include computerized, automated methods. In a first step, one or more rules is defined to associate a feature of a TES waveform with a feature of the temporally structured experience (e.g. song, video, rollercoaster ride, etc.). Examples of TES waveform features that may be used for this type of automated alignment and coordination of a TES waveform with a temporally structured experience include a TES waveform parameter including one selected from the list of: intensity, frequency, duty cycle, percent charge imbalance, bursting frequency, bursting duty cycle, etc.; a ramping or other shift between one TES waveform value and another (i.e. time period over which the ramping occurs, start and stop values for the ramping, and shape (e.g. linear vs. exponential) of the ramp); or a brief 'add-in' TES waveform component intended, for example, to elicit a visual or particular skin sensation. For a video (film, TV show, and the like), the associated feature from the video may be a scene change (detectable through machine vision algorithm or manual entry of times of scene changes), the presence of a particular character (detectable e.g. through facial recognition), a change in a musical or psychoacoustic property of the video's score (detectable through musical analysis), or spoken language (detectable through semantic or lexical analysis for mood, valence, meaning, etc.).

Coutinho et al. (Musical emotions: Predicting second-by-second subjective feelings of emotion from low-level psychoacoustic features and physiological measurements. Coutinho; Cangelosi, Angelo Emotion, Vol 11(4), August 2011, 921-937.) defined psychoacoustic categories including loudness, pitch level, pitch contour, timbre, tempo, and texture and assessed the second-by-second levels of emotional arousal and valence by measuring physiology (i.e. heart rate and skin conductance) and collecting subjective reports from subjects. The authors observed statistically significant correlations between a subset of psychoacoustic categorical variables and subject's emotional arousal and valence:

TABLE 1

Correlated musical psychoacoustic variable and subject emotional arousal or valence (Coutinho et al. 2011)

| Type of emotional effect | Psychoacoustic property of music |
| --- | --- |
| arousal | loudness |
| arousal | tempo |
| arousal | pitch level |
| arousal | sharpness |
| valence | tempo |
| valence | pitch level |

The Coutinho et al. findings show example correlations between music and emotional responses that can be used to define an algorithm for to match, complement, or otherwise modulate the musically-induced changes in cognitive state (i.e. emotion) by TES delivered concurrently to the subject. Though it should be recognized that the relationships observed are exemplary only and should not be considered as the only potential relationships between features of music and emotional, physiological, or cognitive states.

The aforementioned examples are not meant to be limiting and one skilled in the art will recognize that other aspects of a temporally structured sensory experience (i.e. music, video, rollercoaster ride, etc.) and other algorithmic rules may be used for defining TES waveform parameters to associate with features of the sensory experience.

In other embodiments, a hybrid semi-automated method (i.e. manual with automated suggestions for timing and parameters of TES waveform elements of an ensemble TES waveform) is a third method for designing TES waveforms for alignment of TES sessions with a temporally structured sensory experience. For example, a TES waveform designer (of an ensemble TES waveform) may select from a list of suggested waveform parameter sets. Further, suggestions for the timing of when and over what period of time (i.e. by ramping) to select a new set of waveform parameters may be generated automatically. For example, sharp transitions in musical tempo or timbre may be identified automatically and suggested as time periods for integrating a phosphene to be delivered to a TES recipient. As mentioned above, the timing (and/or parameters) of the TES delivery may be choreographed with the concurrent audiovisual performance, and may include a delay in the delivery of the audio and/or visual experience so as to synchronize with the evoked cognitive effect (which will typically occur with a slower onset than the audiovisual impact being choreographed with). Thus, any of the apparatuses described herein may communicate with and/or control the application of the audiovisual input(s) including coordinating a delay between the applied TES and the audiovisual performance.

For example, a first method for generating TES waveforms to align to a temporally structured sensory experience is to adjust the length of TES session to match a song or album (e.g. from a user's music library on the smartphone). To expand or contract a TES waveform to match the length of a song, album, video, podcast, or playlist certain blocks (of an ensemble waveform) may be designated as appropriate to be shortened, lengthened, or repeated. In at least some instances, the start and end of a TES waveform, which generally ramp in a particular way for comfort, are fixed, while intermediate periods of the TES waveforms may be appropriate for changing in length and/or repeating an appropriate number of times.

TES waveforms may be configured to match songs in a streaming music service and to auto-select matched TES waveforms by using an API for the streaming service (e.g. Spotify, Rdio, etc.) and/or for the TES waveform service in order to download, select, or stream a TES waveform appropriate for delivery concurrently with the song.

In variations, TES waveforms may be integrated with virtual reality environments. For example, TES waveforms in a virtual reality environment may be dynamically adjusted based on a user's interaction with and experience in the environment in order to maintain a well-matched experience despite the absence of a fully predictable temporal structure to the virtual reality experience (due to the user's agency).

In variations, TES systems may be integrated with an augmented reality environment (e.g. via a smartphone, smartwatch, or tablet screen, wearable glasses-style display which may, in some variations, serve as a controller for both the augmented reality experience and a neurostimulator). The reality viewed and parsed via an augmented reality system may be used to start, stop, select, adjust, amend, or otherwise modulate a TES session. For example, in a stressful situation (e.g. traffic, facial recognition of an angry client entering your office), the controller may automatically trigger the neurostimulator to deliver a TES session for enhancing calmness.

In general, a TES controller may be configured to start, stop, select, adjust, amend, or otherwise modulate a TES session based on a reading of a physiological sensor. For example, the controller may cause the neurostimulator to start a TES session to enhance a state of calmness when sympathetic activity is too high (e.g. as assessed by: EEG, infrared facial thermography (e.g. with a forward looking infrared (FUR) camera), heart rate, heart rate variability, breathing rate, etc.). In another example, the controller may cause the neurostimulator to start a TES session to increase alertness and energy when sympathetic activity is too low (as assessed by a physiological recording or measurement, as in the list above).

In variations, the neurostimulator or controller of the neurostimulator comprises a microphone to record sound in a user's environment (e.g. music as at a concert, a nature sound, or spoken word (to which linguistic analysis may be applied to determine valence, etc.)), then applies signal processing and control logic algorithms to start, stop, select, adjust, amend, or otherwise modulate a TES session (i.e. change one or more parameter of the waveform such as intensity, frequency, duty cycle, charge imbalance, bursting frequency, and bursting duty cycle, etc.). In a social variation, the recording of sound may be in one environment (i.e. location) via either a fixed microphone or microphone array (e.g. at a concert venue, at the beach, on a whale, in a lecture hall or courtroom, etc.) or recorded by another individual In a next step, the audio recording may be processed locally (e.g. with a user computing device or a processor on the neurostimulator) to parse triggers for selecting, starting, stopping, or modulating a TES waveform. Alternatively, the audio may be transmitted via the Internet (or other communications protocol) to a remote server or other computing device to parse triggers for selecting, starting, stopping, or modulating a TES waveform. Then in a third step instructions are transmitted to the neurostimulator to start, stop, select, adjust, amend, or otherwise modulate a TES session (i.e. change one or more parameter of the waveform such as intensity, frequency, duty cycle, charge imbalance, bursting frequency, and bursting duty cycle, etc.) to complement the user's experience in a unique and interesting way. A similar approach may be used with a camera and machine vision algorithms. Similar to the application of TES sessions during virtual reality, the TES waveforms in this case are not pre-defined.

Delivering Tes Waveforms at a Group Event

As described in pending PCT/US2014/018061 (filed Feb. 24, 2014), published as WO 2014/130960, more than one TES apparatuses may be coordinated to modulate the experience of a group of individuals to an audiovisual experience, including a performance. This application is herein incorporated by reference in its entirety.

In variations, the experience of film, musical, political, sporting, and other events experienced in groups are enhanced or modulated by concurrently delivering TES to modify the cognitive state of two or more individuals. For example, members of an audience at a concert, club with a DJ, other musical experience, sporting event, political rally, religious service, or other group experience use a TES system during the event that induces neuromodulation and enhances the audience members' experience of the event. The venue may be an intimate and small with a small audience (e.g. less than 50 people) or large at an outdoor music festival or stadium (e.g. with an audience exceeding 10,000 people). In at least some instances wherein multiple members of an audience all receive TES, their shared experience of the event is enhanced.

In embodiments, TES users may bring a TES system to the venue and stimulation is triggered to audience members based on proximity, geographic location, or request by the user (e.g. by entering a code into a TES app or scanning a QR code specific to the event on their smartphone, so that an app can trigger an appropriate waveforms at times selected by one or more of the performers or staff of the performance). Wireless communication directly to a TES system is one way to communicate with a TES system so that stimulation can be triggered with timing and waveform selected by one or more of the performers or staff of the performance. In some embodiments, the system is configured so that a performer (e.g. musician, DJ, dancer, etc.) triggers TES stimulation directly (e.g. with a foot pedal; a button on an electronic instrument such as a synthesizer; or a remote control). In other embodiments, the system is configured so that a supporting staff member controls TES stimulation of members of the audience, similar to the way that a mixer at a sound board or a person controlling a light show can control delivery of sensory stimuli to the audience.

In some systems and methods for TES integration with a musical performance, a performer also wears a TES system and receives neuromodulation during a performance. The performer's neuromodulation may be concurrent with the audience's neuromodulation or may alternatively occur at a different time. The performer may have their TES system configured so that the form of neuromodulation they receive is the same as the audience or, alternatively, the form of neuromodulation received by the audience is different than that received by the performer.

TES can be similarly configured so that leaders of other forms of group experiences such as sporting events, political rallies, motivational speeches, or religious events control TES stimulation received by members of the audience.

In an alternative embodiment, an individual who wishes to share in the experience of a musical performance or other group experience listens to a recording in their home by themselves or in a small group while wearing a TES system that is activated at appropriate times relative to the audio so that the user can experience a version of the event without being there, much as listening to a recording of a live concert permits an enjoyable proxy to being at the event.

In an exemplar embodiment, attendees at a club with a DJ performing a set of electronic dance music or other music receive a wearable TES system upon entry to the club, adhere TES electrodes at appropriate locations based on instructions provided by the performer and/or kit, and receive electrical stimulation triggered remotely.

An advantageous feature of this system is the capacity to integrate TES with the musical performance and light show in order to enhance the concert experience.

In embodiments, the performer or other member of the performance staff defines the timing of TES and each user controls one or more aspects of the TES protocol selected from the list including but not limited to: waveform, intensity, cognitive state induced, and length. In an alternative embodiment, the performer or other member of the performance staff defines the timing of TES as well as an aspect of the waveform (e.g. ramping of the waveform to control the relative intensity of an induced cognitive effect in a member of the audience.

In variations, the timing and other features of TES controlled by a performer or other member of the performance staff are: (1) controlled in real-time to respond to the energy of the audience; (2) pre-recorded or otherwise pre-determined; or (3) triggered based on a pattern of sound, light, or other stimulus.

In variations, all participants or attendees experience the same form, duration, and timing of TES. In other embodiments one or more of TES form (e.g. change in cognitive state induced), TES duration, and TES timing differs among members of the audience, for instance in groups, sections, sets, or by demographics of audience members (e.g. males experience one form of TES and females receive a different timing or form of TES).

Systems

Figure 3A:
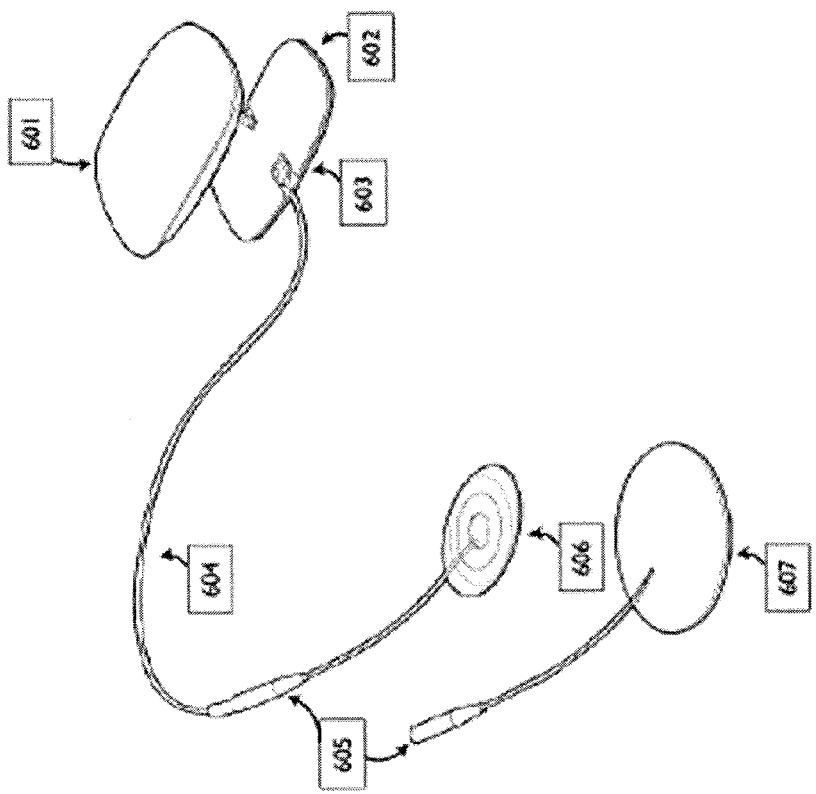
FIG. 3A illustrates one example of a neurostimulator that may be configured for use with (and may deliver) the ensemble waveforms described herein.
Figure 3F:
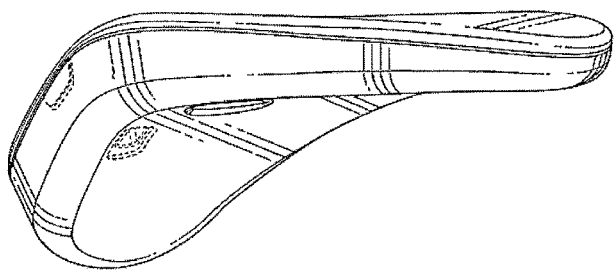
FIGS. 3B-3G illustrate another example of a neurostimulator as described herein.
Figure 3E:
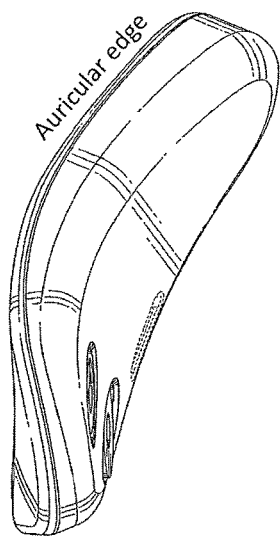
Figure 3D:
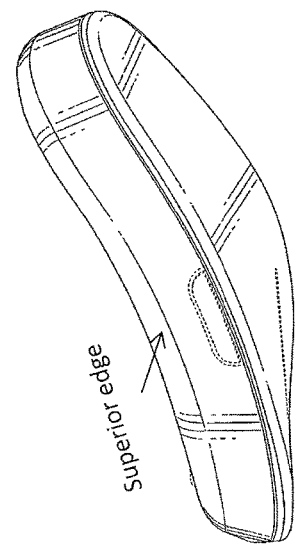
Figure 3G:
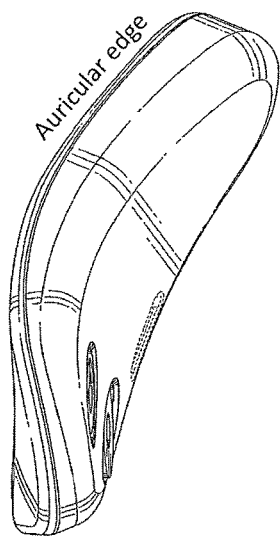
Figure 3B:
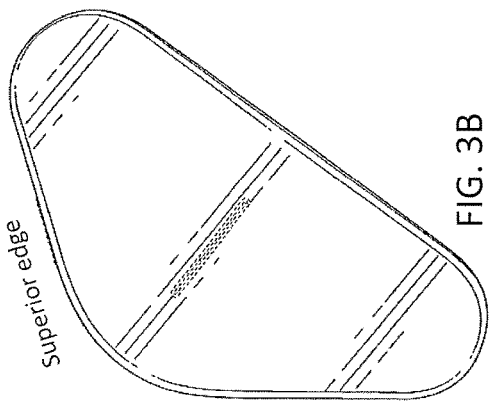
Figure 3C:
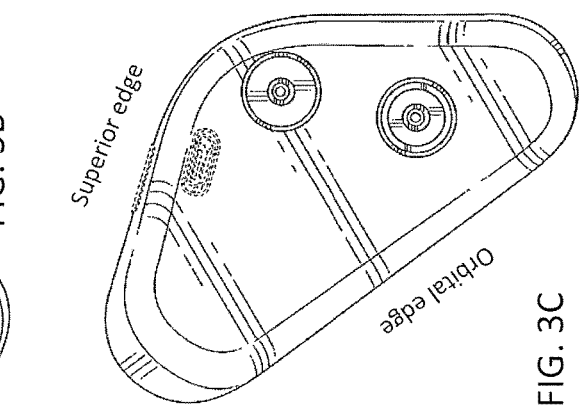
Figure 3Q:
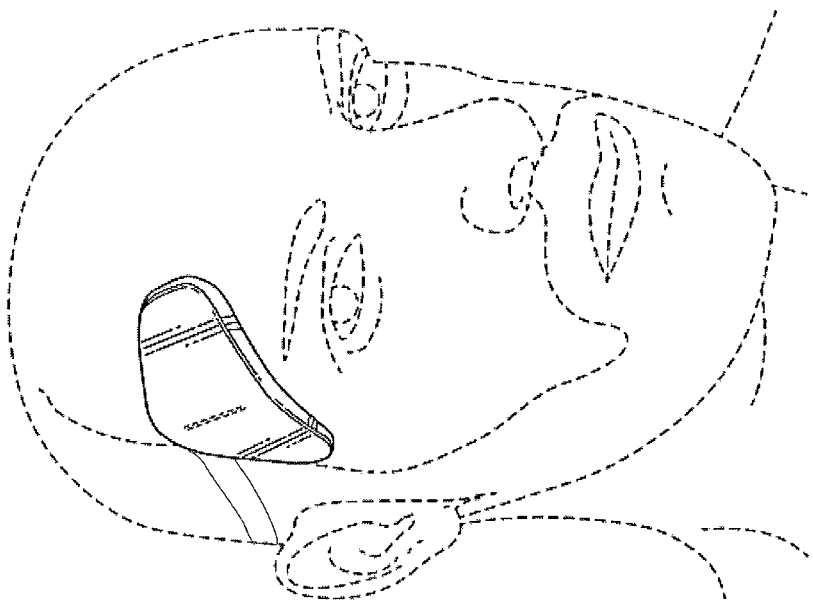
FIG. 3Q illustrates the neurostimulator device worn on the subject's head.

In general, any appropriate neurostimulation system may be used for delivering TES to a subject concurrently with a temporally structured sensory experience as described herein. FIGS. 3A-3Q describe and illustrate an example of a neurostimulation system (neurostimulator, electrodes, controller, etc.) that may be used. For example, a neurostimulation system may include a lightweight, wearable, neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver TES waveforms during a temporally structured sensory experience (e.g. music, video) as described herein. For example, the neurostimulator device may comprise a memory, a music player, and a speaker for playing songs matched to the TES waveform. In another example, the neurostimulator control may also contain a screen, a memory, and a video player (and, optionally, speaker) for displaying a video concurrently with an ensemble TES waveform. For example, the user device may present a list of ensemble waveforms and allow the user to select among them in order to select a desired cognitive effect. The ensemble waveforms may be ordered by the desired effect (e.g., calm, energy, etc.) and/or by time and/or by ranking, and the associated music or video or other temporally structured sensory experience may be indicated, etc. Further, the user device may be adapted to communicate with the wearable neurostimulator and may transmit an identifier of the selected ensemble waveform, and/or waveform parameters that define all or a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device maybe configured to send, and the neurostimulator to receive, the ensemble waveform parameters (duration, ramping parameter/ramping time, capacitive discharge parameters, current amplitude, frequency, percent duty cycle, percent charge imbalance, bursting frequency, bursting duty cycle, etc.).

The user device may also be referred to herein as a controller, and the controller (user device or user computing device) may typically be separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smartwatch, virtual reality headset, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e., by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein. The controller may be a component of the neurostimulator apparatus itself. In some variations, the controller, including general purpose devices, may play music or display video configured to be associated with the TES waveform.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; an increase psychophysiological arousal associated with changes in the activity of the hypothalamic-pituitary-adrenal axis and/or the reticular activating system; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; maintaining a state of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heartbeat.

Figure 5A:
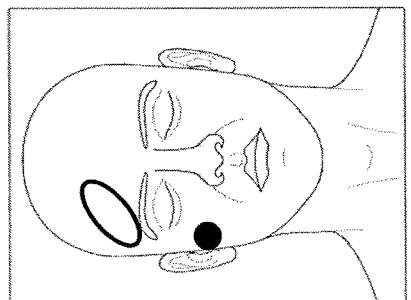
FIGS. 5A-5F illustrate locations for electrodes on the forehead/temple and upper cheek of a TES neurostimulator system for inducing a state of enhanced energy.
Figure 5B:
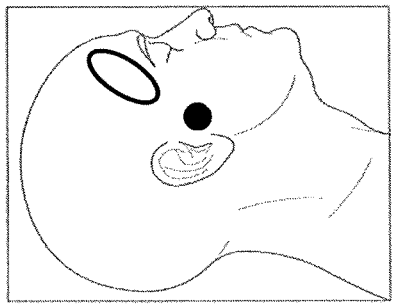
Figure 5C:
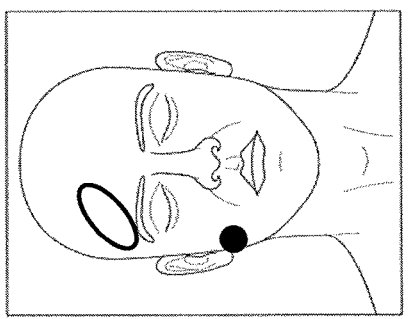
Figure 5D:
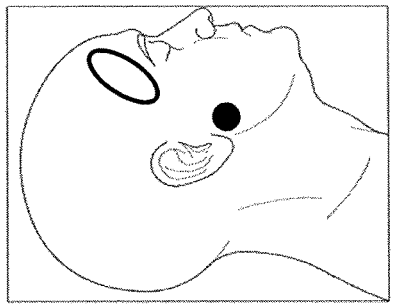
Figure 5E:
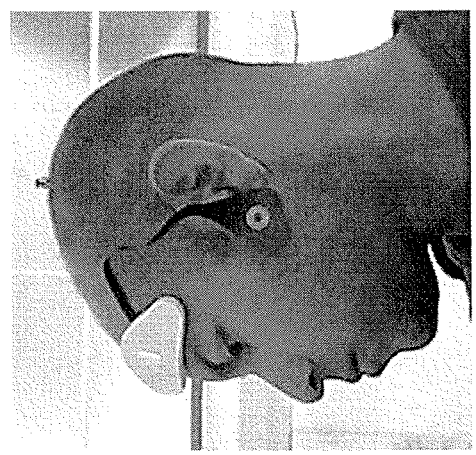
Figure 5F:

For example, to induce energy, the electrode apparatus may be attached to the user's temple (and/or forehead) and behind the user's ear (e.g., mastoid region) and/or behind the user's cheek in front of the user's ear and/or in front and slightly below the user's ear (e.g., FIGS. 5E and 5F). To induce calm, the electrodes may be attached to the user's temple (and/or forehead) and the back of the user's neck. In general, the neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 3 mA and 22 mA, etc.), and a frequency of >700 Hz (e.g., between 700 Hz and 25 kHz, between 700 Hz and 20 kHz, between 700 Hz and 15 kHz, etc.), the current is typically biphasic and is charge imbalanced, and has a duty cycle of between 10-99% (e.g., between 20-95%, between 30-80%, between 30-60%, etc.). The waveform blocks may include bursting, defined by a bursting frequency and a bursting duty cycle. One or more of these characteristics may be changed during stimulation over timescales of every few seconds to minutes as the ensemble waveform shifts between subsequent component waveforms.

When worn, the system may resemble the system shown in FIG. 3Q, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g., enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind' of electrode it is (i.e., for the calm or the energy mode; or indicating the batch and/or source of manufacture, etc.). FIGS. 3A and 3B-3G illustrate two variations of a neurostimulator.

For example, FIG. 3A illustrates a first example of a neurostimulator as described herein. In FIG. 3A, the neurostimulator is shown with a pair of electrodes attached (though the particular electrodes shown may not be configured to target the locations for electrodes according to the variations of the invention as described herein, they serve as a helpful example of an electrode assembly for use with the system). A first electrode 601 is coupled directly to the body 603 of the TES applicator 602, and a second electrode 606 is connected by a cable or wire 604 to the body 603 of the applicator 602. These electrodes are separate from each other, and may be replaceable/disposable. Different shaped electrodes 607 may be used with the same reusable neurostimulator. The neurostimulator in this example includes a rigid outer body, to which the pair of electrodes is attachable, making electrical contact via one or more plug-type connectors.

FIGS. 3B-3G illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 3B-3G illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 3B-3G the various edges of the neurostimulator are labeled, based on where the apparatus will be worn by the subject, as is illustrated in FIG. 3Q. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges; i.e. trianguloid). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g., at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head (e.g. temple/forehead or mastoid region). A second electrode region (anodic or cathodic) on a separate part of the electrode assembly may be electrically connected to the other connector. For example, the second electrode region may be adapted to fit either on the region over the (other) mastoid bone, behind the subject's ear or a region on the user's neck (e.g., at the base of the hairline, e.g., near the midline of the neck.

The electrode apparatus may be printed (e.g., by flexographic printing, laser printing with conductive ink, silk-screening, etc.) on a flexible (e.g., plastic) substrate (flex substrate) and may also include a pair of connectors (snaps) on the side opposite the skin-facing electrodes. The electrode active regions on the back of the assembly may include a layer of conductor (e.g., silver), a layer of a higher resistance conductor than silver (e.g. a conductive carbon), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 3H-3K illustrate one variation of a cantilever electrode apparatus ("electrode apparatus") that may be used with a neurostimulator and may be worn on a subject's head. Again, this example may be instructive of electrode assembly design in general for a wearable TES neurostimulator it but may not be necessary to target the specific electrode locations as described herein. This variation may be referred to as a "calm" configuration, as it is adapted to connect to a user's temple or forehead and the back of a user's neck. In this example, the cantilever electrode apparatus 400 includes a plurality of electrode portions (two are shown) 403, 405. In FIG. 3H, a front perspective view is shown. The front side is the side that will face away from the subject when worn. The cantilever electrode apparatus is thin, so that the electrode portions include a front side (visible in FIGS. 3H and 3I) and a back side (visible in FIG. 3K). As shown in the side view of FIG. 3J, the device has a thin body that includes the electrode portions 403, 405 as well as an elongate body region 407 extending between the two electrode portions.

The elongate body is also thin (having a much larger diameter and height than thickness). The thickness is shown in FIG. 3J.

In this example, two connectors 415, 417 (electrical and mechanical connectors, shown in this example as snaps) extend from the front of the cantilever electrode apparatus. The front of the first electrical portion 403 may also include an optional foam and/or adhesive material 421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 3H-3K as about 0.72 inches). The second electrode portion may also include a foam or backing portion 423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 3K shows a back view of this first example of a cantilever electrode apparatus. In this example, the first 403 and second 405 electrode portions are also shown and include active regions 433, 435. The active regions are bordered by adhesive 440. The first 403 electrode portion includes, on the back (patient-contacting) side, a first active region 433, which is bounded, e.g., around its entire circumference, or at least on, by an adhesive 440. The active region may include a conductive material (e.g., electrically conductive gel). Similarly, the back of the second electrode portion 405 includes the second active region 435 surrounded on two sides by an adhesive material 440 that extends to the edge of the electrode region. The adhesive may be any biocompatible adhesive that can releasably hold the material to the skin.

FIGS. 3L-3o illustrate another example of a cantilever electrode apparatus. This example is very similar to the variation shown in FIGS. 3H-3K, but may be referred to as an "energy" configuration as it is configured to contact both the user's temple or forehead and a region behind the user's ear, over the mastoid region. This example is just one example of an electrode assembly design for a wearable TES neurostimulator, and is not limited to the specific electrode locations as described herein.

The connectors (snaps 417, 415) are in the same position as shown in FIGS. 3H-3K, as are the shape of the first electrode portion 403 and foam/backing material 421 (which may also or alternatively be an adhesive material). An advantage of having multiple electrode apparatuses with the same shape is that they can be used interchangeably with a single neurostimulator device. However, the example shown in FIGS. 3L-3o includes a different overall shape, and may be used to connect, for example, to different regions of the patient's head. In particular, the portion of the substrate forming the elongate body region 407 extending between the two electrode portions 403, 405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple or forehead and using the adhesive material 440 surrounding the electrically active region 433 to hold the electrically active region (and the attached neurostimulator) securely in position on the subject's skin, the second electrically active region may also be adhesively 441 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 3H-3K and 3L-3o. The bend or curve, in which the elongate body may even double back on itself, may allow the material to flex or bend to allow it to be adjustably positioned over and/or around the subject's head, as shown in FIGS. 3P and 3Q, for example.

Figure 3P:
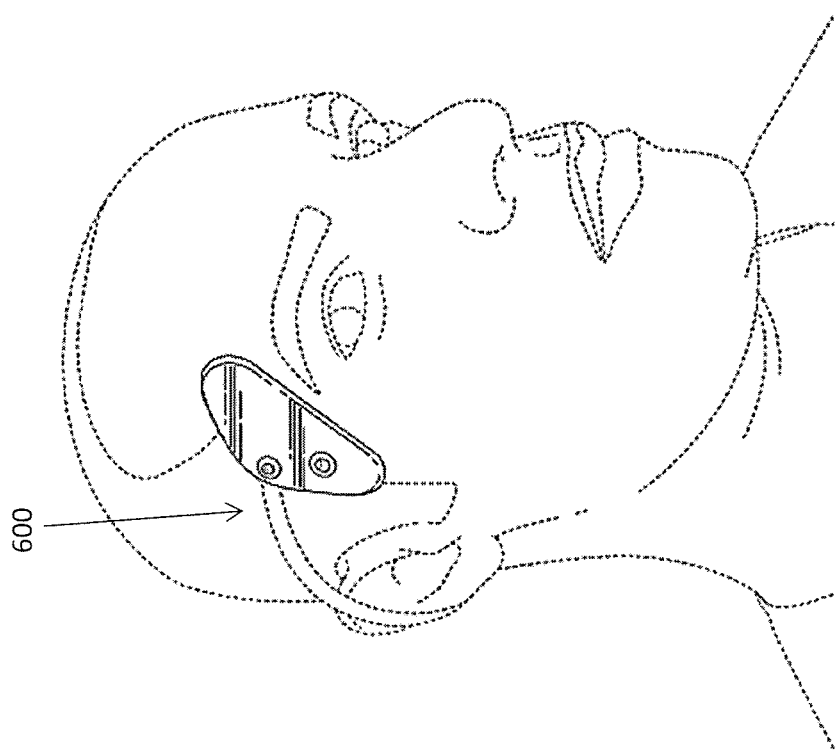
FIG. 3P illustrates the application of an electrode assembly that may be worn on the subject's head, and/or head and neck to induce a cognitive effect.

FIG. 3P illustrates a cantilever electrode apparatus (similar to those shown in FIGS. 1A and 4A) worn on a subject's head. As illustrated, the apparatus is positioned with the first electrode portion adhesively attached at the temple or forehead and a second electrode portion attached to a region behind the head (e.g., behind the ear or neck region, not shown). A neurostimulator (not shown in FIG. 3P) may be attached to the cantilever electrode apparatus either before or after it is applied to the subject. As shown in FIG. 3Q, the neurostimulator may be attached to the front side of the cantilever electrode apparatus by snapping onto the proud connectors, while the elongate body region 407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, filed on Jun. 30, 2014 and titled "TRANSDERMAL ELECTRICAL STIMULATION METHODS FOR MODIFYING OR INDUCING COGNITIVE STATE", now U.S. Pat. No. 9,014,811 and U.S. patent application Ser. No. 14/715,476, filed on May 18, 2015 and titled "METHODS AND APPARATUSES FOR AMPLITUDE-MODULATED ENSEMBLE WAVEFORMS FOR NEUROSTIMULATION", each of which are herein incorporated by reference in their entirety.

In use, a user may interact with a controller (e.g., a smartphone controlled by application software/firmware) that pairs with the neurostimulator (e.g., i.e., by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e., current amplitude, frequency, duty cycle, charge imbalance, shorting/capacitive discharge, bursting parameters, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e., tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol, and in some variations may be used to control the application of waveforms concurrently with music, video, a performance, or another temporally structured sensory experience. A system may include the wearable neuromodulation device, and the user computing device for control of the transdermal electrical stimulation (TES) waveforms.

A time-varying pattern of electrical stimulation delivered transdermally (and, optionally, to some extent, transcranially) to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g., amplitude modulation at one or more frequencies), pulsed current (e.g., amplitude modulation where part of the modulated cycle is at zero intensity), and more complex time-varying patterns of electrical stimulation (including repeated, random, pseudo-random, and chaotic patterns). In operation, the device may provide current flow at target areas (e.g., in the brain, facial nerves (cranial nerves and/or cervical spinal nerves), vagal nerve, or other neuronal targets) to induce neuromodulation when appropriate electrode configurations and stimulation protocols are delivered.

TES waveform parameters that may be used to invoke, enhance, or modify a variety of cognitive states may be considered compound waveforms including a number of different sub-portions that are temporally connected together and delivered to a user in sequence. In general, the ensemble waveform and the component portions can be defined by four waveform parameters that may be used by the neurostimulator to define the component waveforms and, in combination with the duration of each waveform component and in some variations a ramping parameter, may define an ensemble waveform. In some variations, more complex waveforms are used for TES, and additional components may be included, such as transient capacitive discharges, multiple pulses per cycle, phase relationships of two or more pulses per cycle, complex pulse shapes, non-sinusoidal alternating current, etc. In some variations, an ensemble waveform (or portion of an ensemble waveform) may be modulated by an envelope of slower-frequency amplitude modulation (e.g., modulation of the current amplitude parameter). For example different types of amplitude modulation may be applied (e.g., amplitude modulation at frequencies between 0.5 Hz and 1000 Hz may be applied on top of the ensemble waveform. In some variations the amplitude modulation is applied as a sinusoidal (e.g., pure sinusoid, sawtooth, square pulses, etc.); in some variations the amplitude modulation is bursting, and results in an amplitude modulation duty cycle, in which stimulation intensity is decreased or turned off for a pre-determined period and switched on for a pre-determined period (where the amplitude modulation duty cycle can be calculated as the on period duration divided by the sum of the on period duration and off period duration).

The TES waveform components described herein may generally be formed of a basic unit comprising a plurality of biphasic pulses that may be asymmetric with respect to positive and negative going phases and may be charge imbalanced (although one or more capacitive discharging pulses may also be included within each repeating pulse to offset a charge imbalance as described herein). The component waveforms described herein may be defined by a duration and a set of waveform parameters including: a peak current amplitude (in mA), a frequency (in Hz or kHz), a percent charge imbalance, and a duty cycle. FIG. 1A schematically illustrates a basic waveform unit. This example shows the basic unit as a combination of square-waves (steps), however, rounded (including sinusoid), sawtoothed, triangular, and other shapes may be used. The waveform parameters for this basic unit waveform are defined by a duty cycle (or percent duty cycle), percent charge imbalance (also referred to as percent direct current, or percent DC), ramping or other amplitude modulation, one or more multiple frequency components, phase relationship of biphasic current, flat or structured noise, wave shapes (i.e., sawtooth, triangular, sine wave, square wave, exponential, or other wave shape), capacitance compensation features, or other parameters as discussed in U.S. patent application Ser. No. 14/091,121, filed on Nov. 26, 2013 and titled "WEARABLE TRANSDERMAL ELECTRICAL STIMULATION DEVICES AND METHODS OF USING THEM", now U.S. Pat. No. 8,903,494, which is herein incorporated by reference in its entirety.

In FIG. 1A, the biphasic waveform includes a positive-going pulse having an amplitude $I_{peak}$, and a duration $t_p$ (time spent in the positive direction, relative to baseline), a negative-going pulse having an amplitude (in this example, Ipeak but in the negative direction) and a duration tn (time spent in the negative direction, relative to baseline). The total time of the base unit is tc (time for one period of a cycle).

As used herein, 'percent duty cycle' may refer to the proportion of a cycle of a waveform that causes non-zero (or nominally non-zero) current to be delivered transdermally (though for waveforms incorporating capacitive discharge, the nominally non-zero portion of the duty cycle may not include the non-zero portions of the cycle caused by capacitive discharge). For example, the duty cycle in FIG. 1A is the sum of tp and tn divided by tc. Further, the percent charge imbalance (or 'percent direct current') refers to the non-zero portion of a waveform cycle that is positive-going or negative-going (again, excluding capacitive discharges, if present). In FIG. 1A, the percent charge imbalance is the ratio of the difference of tp and tn and the sum of tp plus tn.

Inducing significant, robust, and/or reliable cognitive effects typically requires an appropriate ensemble waveform defined by a set of parameters for each component waveform. A stimulation protocol typically includes a composite waveform that defines the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex patterns (including repeated, random, pseudo-random, and chaotic patterns). In operation, the device may provide current flow at target areas (e.g., in facial nerves, cranial nerves, vagal nerve, in the brain, etc.) to induce neuromodulation when appropriate electrode configurations and stimulation protocols are delivered.

Although the apparatuses and methods described herein may be used to provide TES to induce and/or modify a variety of cognitive states, two particular examples are described in detail herein: (1) enhancing attention, alertness, or mental focus and (2) inducing a calm or relaxed mental state. Configurations of apparatuses and methods for causing neuromodulation that specifically achieve enhanced attention, alertness, or mental focus as opposed to an increased calm or relaxed mental state are described in particular detail.

Thus, a generic neurostimulator for modifying a cognitive state may include a pair of electrodes (or two sets of electrodes), referred to herein for convenience as an anode and a cathode (where the anode and cathode may loosely refer to their function as primarily anode and primarily cathode for biphasic waveform components), that can be applied to specific regions of the subject's body and used to provide TES stimulation within the relatively high-intensity, high-frequency ranges described as effective herein. Current is typically applied between the anode and cathode electrodes (or groups of anode and cathode electrodes). Without being bound by a particular theory of operation, the current may be passed through the body between the anode and cathode electrodes (or groups of anode and cathode electrodes), potentially applying energy in an appropriate treatment regime to underlying neural tissue (nerves, e.g., cranial, cervical spinal, vagal, etc., brain, etc.) in a particular neural pathway to result in the desired target effect (e.g., attention, alertness, or mental focus; inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus may include a first electrode applied to the subject near the temple and/or forehead area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity stimulation (as described in greater detail below) of this region may result in enhanced attention, alertness, or mental focus.

Another configuration of electrode positions may include an electrode positioned on the subject's skin near the subject's temple and/or forehead area (e.g., above and to the right of the right eye) and a second electrode on the subject's neck (e.g., on a superior portion of the neck centered at or near the midline and at least partially overlapping the midline). Appropriate TES stimulation of this region may result in enhancing a calm or relaxed mental state. Either of these configurations may also be used with an appropriate TES stimulation regime (waveform) to induce phosphenes by noninvasive transdermal electrical stimulation using the apparatuses described herein.

Generally speaking, peak stimulation intensities above at least 3 mA (e.g., greater than 5 mA, e.g., between 5 mA and 25 mA, etc.) may be advantageous for transdermal electrical stimulation that causes neuromodulation by targeting the brain, nerves (e.g., cranial nerves, vagal nerve, peripheral nerves, spinal nerves), and/or spinal cord. To achieve these peak intensities without causing significant pain, irritation, or discomfort in a subject may require appropriate electrodes and appropriate ensemble waveforms as described herein. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g., transdermally). Although there may be variations (optimizations) of these waveforms and electrical protocols for each configuration (electrode placement) and each target cognitive state, in general, the patterns may be within the same range of values to provide biphasic, high-intensity, high-frequency and asymmetric with regard to the positive-going and negative-going phases of the waveform (in some cases not charge balanced) signals that are applied to robustly evoke a response in most individuals while causing at most a low level (e.g., minimal or none) of discomfort and/or pain.

Figure 4A:
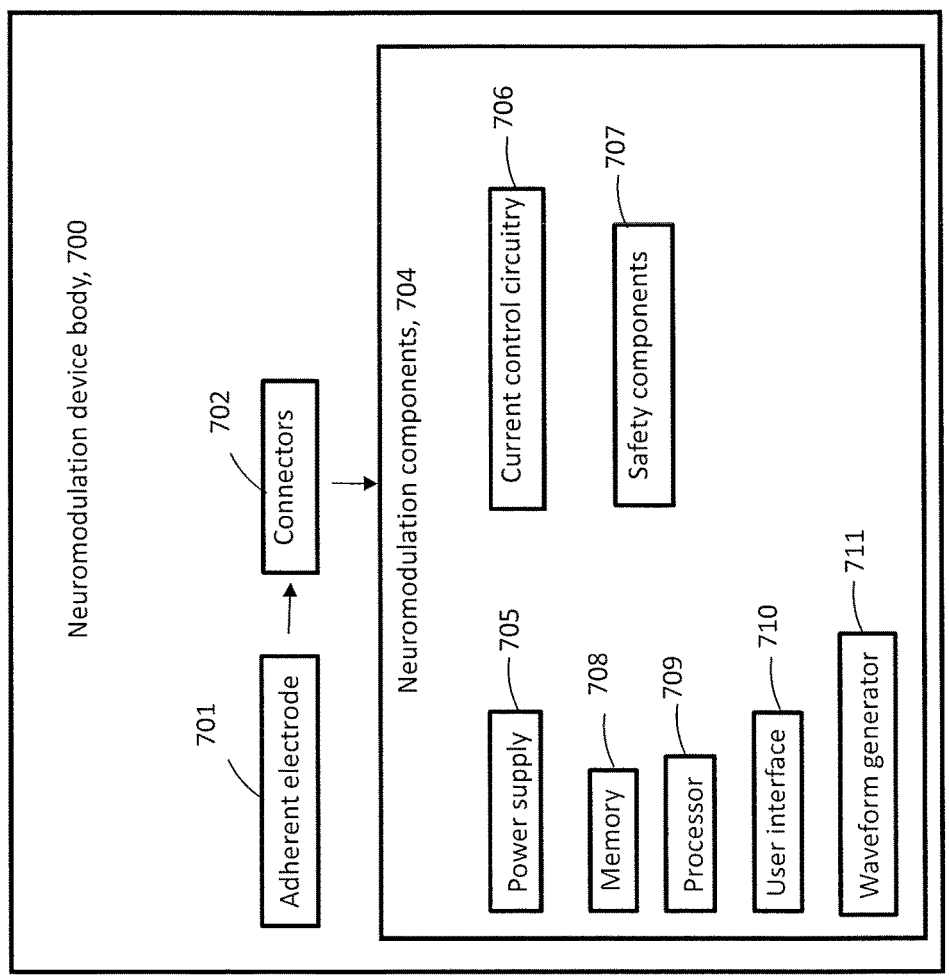
FIG. 4A is a diagram showing the overall configuration of the integrated neuromodulation device.

These waveforms may be ensemble waveforms including a plurality (e.g., 3 or more) of component waveforms having a predetermined value for each of: current amplitude ("intensity"), frequency, percent charge imbalance, duty cycle, and in some variations capacitive discharge. These component waveforms may each have a duration (time), and may be connected together in a sequence to evoke the desired cognitive effect. Some of these component waveforms forming the ensemble waveform are ramps, in which one or more waveform parameter (current amplitude, frequency, duty cycle, percent charge imbalance) of the waveform is ramped up to the target/peak value of the waveform components from the previous value of the waveform components after transitioning to the new component waveform when delivering the ensemble waveform. Generally, tDCS studies have used between about 1 mA and about 2 mA peak currents for longer stimulation periods (e.g., more than a few minutes or seconds), and tACS typically uses relatively low frequencies (e.g., <650 Hz). However, these current levels and frequencies are sub-threshold for at least some forms of neuromodulation. In particular, the inventors have found that higher currents may be necessary for inducing significant and beneficial cognitive effects. Unfortunately, such higher currents may lead to pain, irritation, and damage to skin under high current stimulation conditions. Higher currents than have traditionally been used for TES are required for inducing a change in a cognitive state in at least some instances. Described herein are systems configured to deliver higher currents (optimally 3 mA or higher), at relatively high frequency (>750 Hz, e.g., between 750 Hz and 30 kHz, between 1 kHz and 30 kHz, etc.) to achieve a desired cognitive effect. The ensemble waveforms described herein may reduce irritation, pain, and burning sensations in the dermis, muscles, and other tissues of users receiving TES. These embodiments permit higher current intensities to be transmitted comfortably so that desirable changes in a subject's cognitive function, cognitive state, mood, and/or energy levels can be attained. In addition to the high current amplitudes, high frequency (e.g., repeating the base waveform of FIG. 1A between about 650 Hz and about 50 kHz (e.g., between about 750 Hz and about 40 kHz, between about 1 kHz and about 35 kHz, etc.) may provide biphasic pulsed and/or alternating current stimulation that minimally activates sensory pathways and minimizes pH changes in tissue due to stimulation. As can be seen in FIG. 4A, the neuromodulation device body contains an electrode assembly 701, and neuromodulation components 704. The neuromodulation components 704 further contain power supply 705, memory 708, processor 709, user interface 710, current control circuitry 706, and safety components 707. A skilled artisan will appreciate that FIG. 4A is one representation of how the neuromodulation device components can be laid out and there are numerous other ways for both the electrodes 701 and neuromodulation components 704 to be integrated.

Figure 4B:
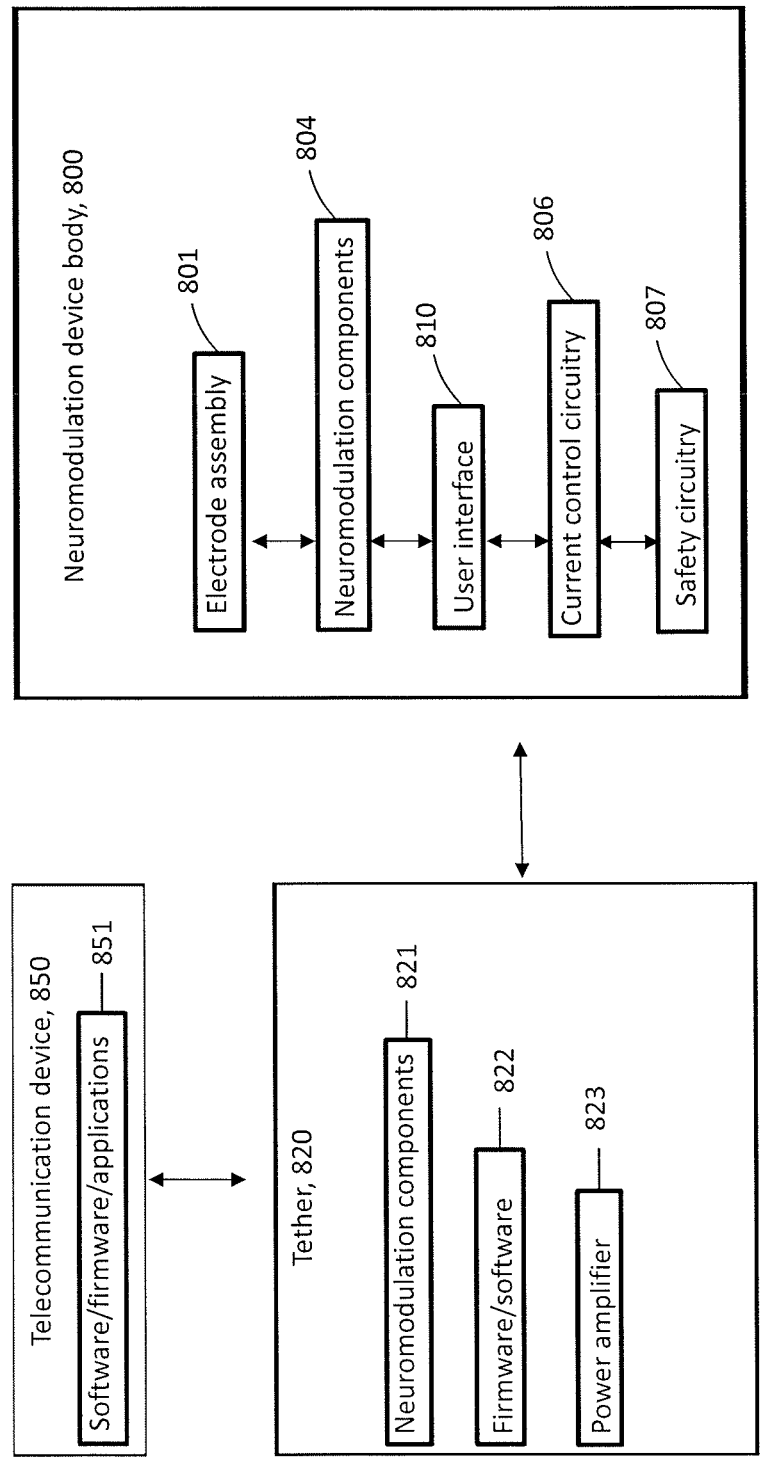
FIG. 4B is a diagram showing the configuration of integrated neuromodulation device connected to a tether and a telecommunication device.

In a second embodiment of the present neuromodulation device as shown in FIG. 4B, a physical tether, such as a wire or cord, can be established between the neuromodulation device and a communication device (such as a smartphone or a tablet). The tether 820 can contain some of the neuromodulation components 821 as well as firmware/software 822 for controlling the neuromodulation device body 800, and a power amplifier 823 for boosting the power available to the neuromodulation device. In this embodiment, the neuromodulation device can also draw power from the communication device for outputting any particular waveform session. This can prove useful, because the primary power drain on the neuromodulation device will be the delivery of the stimuli from the first and second electrode to the subject's skin. Having a secondary source of power to draw from can decrease the size of the power supply used within the actual neuromodulation device. In one example of this second embodiment, the cord or wire used to connect the neuromodulation device to the control device can be a standard wire or cord. In a second example of the second embodiment, some components related to the neuromodulation aspect of the device (such as creating the waveforms, outputting the waveforms) can be placed external to the main neuromodulation device and retained within or hard-wired to the cord or wire in a housing.

In various embodiments, the controller of the TES neurostimulator may include a capacitive discharge circuit configured to discharge a capacitance on the electrodes during the delivery of the biphasic electrical stimulation signal. TES neurostimulators that incorporate discharging the capacitance on the electrodes may be useful for pulsed stimulation regimes, and may help reduce or prevent pain and discomfort. In some variations the apparatus includes capacitance discharging circuitry in connection with the electrodes. For example, capacitance discharging circuitry may include electronic components and firmware features that short the anode-cathode path to permit discharge of capacitance that builds up during a pulse (e.g., in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). In general, controlling the maximum current of a capacitance discharging pulse may be beneficial for tuning the comfort of a TES waveform (e.g. to vary the maximum current of discharge based on the estimated amount of capacitance built up, which is expected to correlate with increasing imbalance (i.e. duration and/or peak current) between positive-going and negative-going pulses, as well as by frequency, where lower frequency stimulation at a fixed duty cycle will cause relatively more capacitance build-up per cycle).

In some embodiments, the wearable transdermal electrical stimulator may comprise a control module having the capacitive discharging features (which may be referred to as a 'short circuiting' applicator) described. For example, the wearable transdermal electrical stimulator may include: a housing configured to be connected to a first electrode and a second electrode, a control module at least partially within the housing including: a processor, a waveform generator configured to deliver a biphasic electrical stimulation signal between the first electrode and the second electrode, and a capacitive discharge circuit configured to discharge a capacitance on the first electrode and the second electrode during the delivery of the biphasic electrical stimulation signal. The TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation.

Figure 2B:
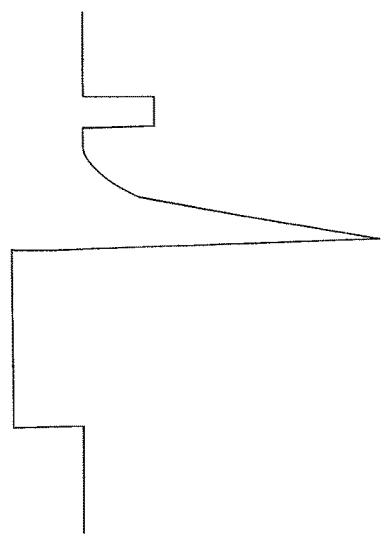
FIG. 2B schematically illustrates a capacitive discharge pulse triggered immediately after the positive pulse.
Figure 2D:
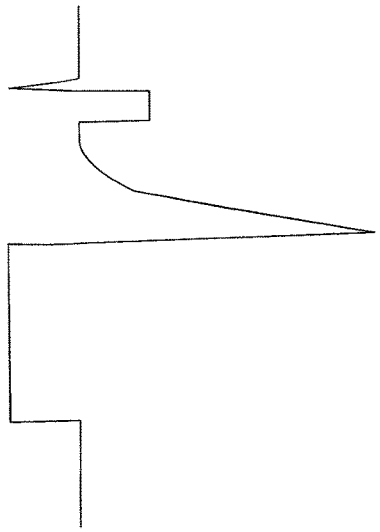
FIG. 2D schematically illustrates capacitive discharge pulses triggered immediately after the positive pulse and the negative pulse.
Figure 2A:
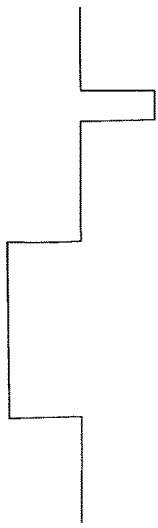
FIG. 2A schematically illustrates a biphasic electrical stimulation waveform with a positive pulse and a negative pulse in one cycle.

FIG. 2A schematically illustrates a biphasic electrical stimulation waveform with a positive pulse and a negative pulse in one cycle. In some embodiments, the firmware may create segments in a waveform cycle. The smallest segment may be limited by the clock of the processor. For example, in some embodiments, the shortest segment per cycle can be 2, 5, or 10 microseconds or any values therebetween. For example, in some embodiments, the firmware may create 10, 12, 15, or 20 segments per cycle. For each segment of the cycle, the controller may instruct the waveform generator to generate a positive intensity value, a negative intensity value, a value of "zero" which indicates an open circuit mode, or a capacitive discharge.

Figure 2C:
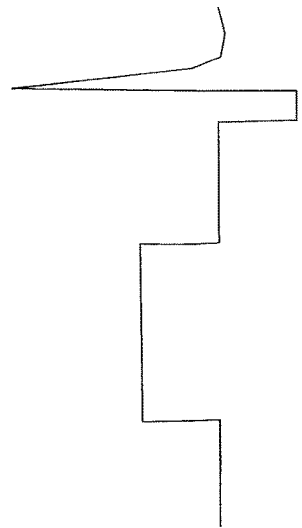
FIG. 2C schematically illustrates a capacitive discharge pulse triggered immediately after the negative pulse.

In some embodiments, the capacitive discharge (which may be referred to as "short-circuiting" although it is not the result of shorting) can be triggered immediately after the positive pulse or negative pulses as shown in FIGS. 2B-2D. For example, as shown in FIG. 2B, at the time when the positive pulse ends, the controller triggers the capacitive discharge circuit to short the anode-cathode path, resulting in a capacitive discharging pulse to permit discharge of capacitance. The minimum duration of the capacitive discharging pulse may be limited by the shortest segment of the cycle as discussed above. Thus the duration of the pulse can be larger than 2, 5, or 10 microseconds. However, the duration of the pulse may not be too short. It might be advantageous to have a more gradual pulse to prevent pain in the subject. It might be advantageous to have a limited peak value of the pulse to further prevent pain and discomfort. The peak value and the time constant of the capacitive discharging pulse may be controlled by the capacitive discharge circuit. In some other embodiments, the capacitive discharge can be triggered immediately after the negative pulse as shown in FIG. 2C. In some embodiments, the capacitive discharge can be triggered both after the positive pulse and after the negative pulse as shown in FIG. 2D.

Figure 2E:
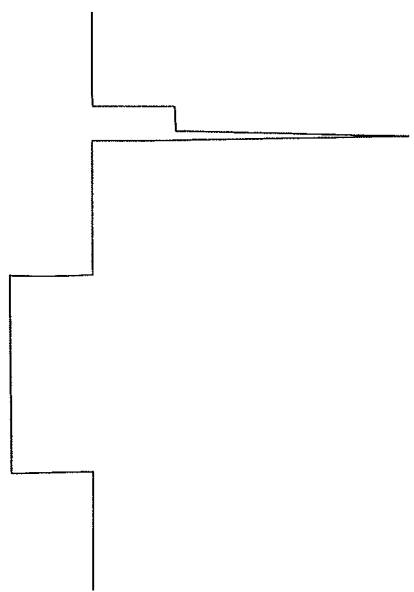
FIG. 2E schematically illustrates a capacitive discharge pulse in the negative going direction that occurs at the onset of a negative going pulse.

In some alternative embodiments, the capacitive discharging pulse can be triggered at the onset of each negative-going pulse in the negative-going direction as shown in FIG. 2E. For example, in the "energy" mode, the capacitive discharging pulse can be triggered at the onset of each negative-going pulse in the negative-going direction to induce an enhanced cognitive state. In some other embodiments, the capacitive discharging pulse may be triggered at the onset of each positive-going pulse in the positive-going direction. In some other embodiments, the capacitive discharging pulse can be triggered both at the onset of each negative-going pulse in the negative-going direction and at the onset of each positive-going pulse in the positive-going direction.

An advantage of the ear-based TES systems and methods described herein may include co-delivery with an audible signal. Novel cognitive effects may be induced by aligning in time (in some cases, with a temporal offset) an auricular TES waveform with an audible signal through coordinated activation of auditory pathways with cranial and/or cervical spinal nerve downstream pathways. For example, any of these methods may include delivering an audible signal to the subject from the TES applicator. Any audible signal may be used, including one or more of: a song (e.g., music), a tone or tones, a chant, spoken language, instrumental music, white noise, structured noise (e.g. pink noise, brown noise, frequency-modulated noise), binaural beats, recorded or synthesized sounds (e.g. ocean noise, wind noise, running water, etc.), or the like. In variations, the audible signals may take the form of instructions or advisements about the TES applicator (e.g. 'recharge device' or 'one minute remaining'); may take the form of music, chants, recorded sounds, and/or synthesized sounds timed and temporally sequenced to match, enhance, or otherwise modulate the cognitive effects induced from auricular TES alone; or may take the form of binaural beats in bilateral variations of the system (i.e. higher frequency audible signals (generally frequencies above 200 Hz) with phase offsets at frequencies of brain rhythms (generally less than 200 Hz).

For example, any of these methods may include delivering an audible signal to the subject from the TES applicator wherein the audible signal is delivered from an earbud TES applicator.

Temple and Mastoid Electrode Pairs

The exemplary apparatuses descried above and shown in FIGS. 3B-3Q and 5A-5D illustrate examples configured to apply stimulation to a subject's head and/or neck. In general, the location in which neurostimulation is applied, in conjunction with the applied TES waveform(s), may profoundly affect the efficacy and effect of the resulting neurostimulation. For example, stimulation in regions other than those described herein may not be effective at all, or may result in discomfort, and undesirable effects (e.g., may evoke anxiety, rather than calm, etc.).

Also described herein are methods and systems for inducing cognitive effects by delivering transcranial/transdermal electrical stimulation (hereinafter 'TES') with electrodes on the temple and mastoid. This configuration, illustrate in FIGS. 5E and 5F may provide an alternative placement option and may be beneficial compared to other electrode placement options. For example, in some variations one electrode of the TES system is placed on the temple or forehead region and a second electrode is placed on the upper cheek area on the same side of the head. The upper cheek region includes areas anterior to the ear, as well as anterior and below the auditory canal. The advantage of placing both electrodes on the same side of the head in this configuration is that the overall footprint of the system may be made small. That is, because there is relatively little distance between the electrode (generally less than 3 inches and more frequently less than 2 inches, e.g., between 1 inch and 3 inches, between 1.5 inches and 3 inches, between 2 inches and 3 inches, etc.) the overall footprint of the electrode assembly (and neurostimulator assembly attached thereto which delivers current through the electrode assembly into the skin) is small, improving the portability and wearability of the system (e.g. permitting weaker adhesive or smaller adhesive areas to hold the system in place on the user's skin). With these electrode locations, a cognitive effect of enhanced energy may be induced using stimulation waveforms as described below. Exemplar locations for TES dermal electrodes on the temple/forehead and cheek according to these variations of the invention are shown in FIGS. 5A-5F.

Figure 6:
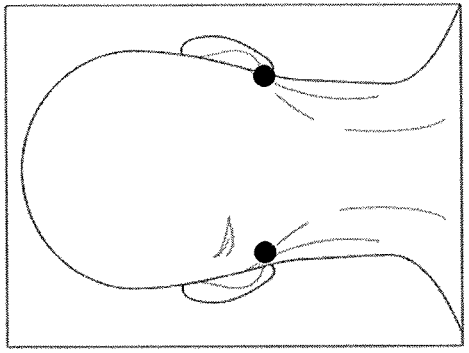
FIG. 6 illustrates electrode positions on the mastoid bilaterally for inducing various muscle contractions and inducing changes in cognitive state (e.g. through proprioceptive pathways) by stimulating the facial nerve.

In other variations of the system, two electrodes are placed bilaterally over the mastoids (i.e. bilaterally) and apply waveforms as described below to induce various contractions of facial musculature via stimulation of branches of the facial nerve. Stimulating via electrodes in this configuration may be effective for inducing changes in mood and cognitive state via proprioceptive pathways. For example, by placing electrodes in these locations near the stylomastoid foramen (bilaterally), the facial nerve may be activated (or otherwise modulated), causing various patterns of facial muscle contraction by projections of the facial nerve. Exemplar locations for TES dermal electrodes bilaterally on the mastoid according to these variations of the invention are shown in FIG. 6.

User Interface

Any of the TES neurostimulation apparatuses and methods described herein may be configured for use by a consumer (e.g., user) for personal use. Also described herein are user interfaces and methods and system for operating and servicing these TES apparatuses, as well as methods and systems for improving user experiences and compliance. As will be described in greater detail below, FIGS. 7A-13E illustrate one variation of a user interface (UI) for controlling operation and servicing of a TES apparatus that modulates a user's cognitive state. FIGS. 14A-19F illustrate methods of operation, reordering, and user guidance; these principles may be provided to a user with a TES apparatus. In general, the UI may be, for example, an application software ("app") running on the user electronics device.

Any of the TES apparatuses described herein may include client or user software, firmware and/or hardware that may include or be adapted for operation on a user electronics device such as a handheld or wearable electronics device (e.g., smartphone, pad, computer, smartwatch, etc.). The user electronics device may communicate and/or control operation of the TES apparatus. In particular, the user electronics may include a user interface for controlling operation of the TES apparatus.

Figure 7A:
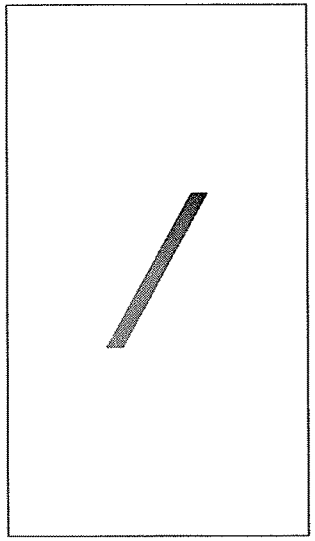
FIGS. 7A-7F show screens of an app for controlling a neurostimulator for TES that allow a user to log in, pair a neurostimulator wirelessly via Bluetooth, and view Warnings and Terms.
Figure 7B:
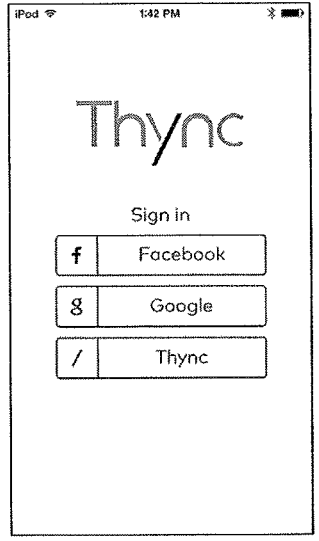
Figure 7C:
Figure 7D:
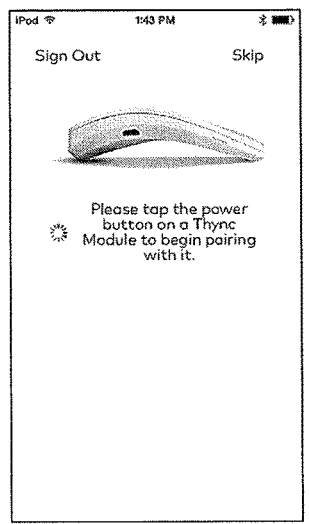
Figure 7E:
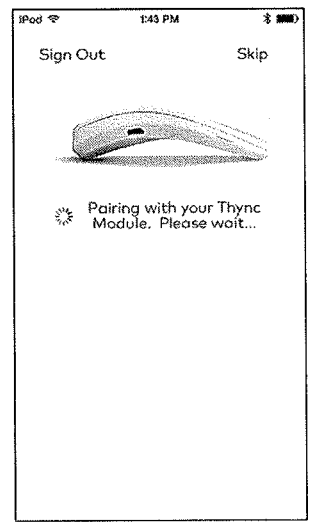
Figure 7F:
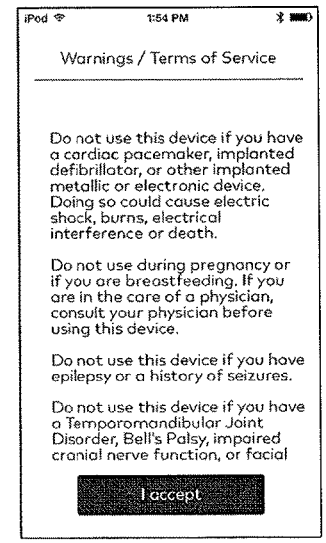

For example, FIGS. 7A-7F illustrate introductory information from a UI that may be used to communicate between a user wearing the TES applicator and the control for the device. In FIG. 7A the user may be presented with an introductory screen, and in FIGS. 7B and 7C may be presented with sign-in and/or registration prompts that allow the UI and therefore the TES apparatus to identify the user. The TES applicator may be locked or otherwise prevented from operating until login and/or registration has occurred. The apparatus may also coordinate with remote servers and/or processes (FIG. 7B). The UI may also prompt or walk the user through the pairing or otherwise communicating with the wearable TES apparatus, as shown in FIGS. 7D-7E, and may present information such as warnings, terms of use, and the like (FIG. 7F).

Figure 8:
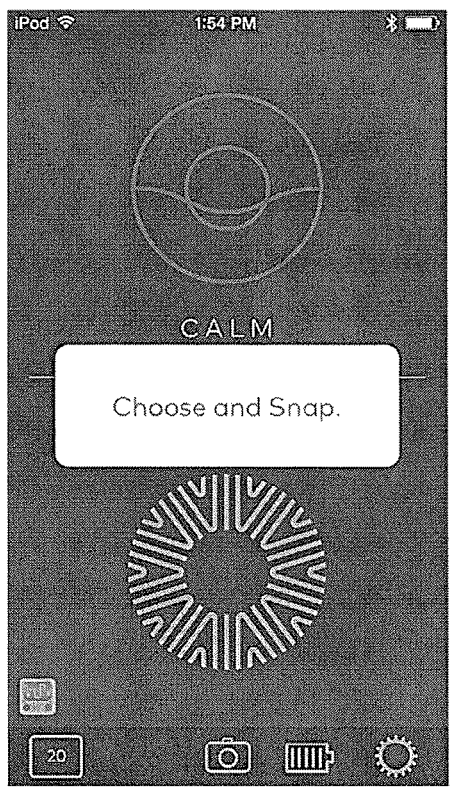
FIG. 8 shows a screen of an app for controlling a neurostimulator for TES that instructs a user to choose a subtype of an electrode assembly and snap it (connect mechanically and electrically) to a neuromodulator.

In general, the US may allow the user electronics device to control the TES apparatus, including the attachment and confirmation of an electrode. For example, as shown in FIG. 8, the UI may coordinate attachment of a particular electrode (and may include instructions stepping the user through attachment, including presenting video, text and/or audio instructions). The UI may also include automatic detection of the 'type' of electrode (e.g., a 'calm' configured electrode for attachment at the temple and back of the neck, an 'energy' configured electrode for attachment to the temple and region behind the ear, etc.).

Figure 9:
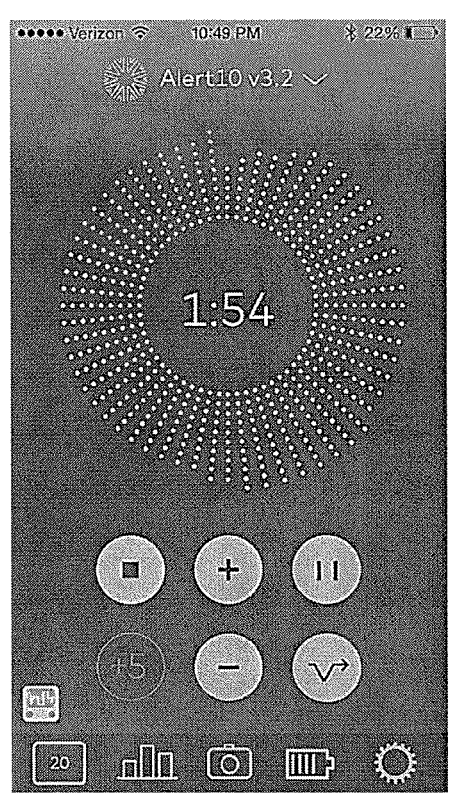
FIG. 9 shows a screen of an app for controlling a neurostimulator for TES that provides various user controls for electrical stimulation and information (i.e. time remaining, intensity) for the TES session.
Figure 10A:
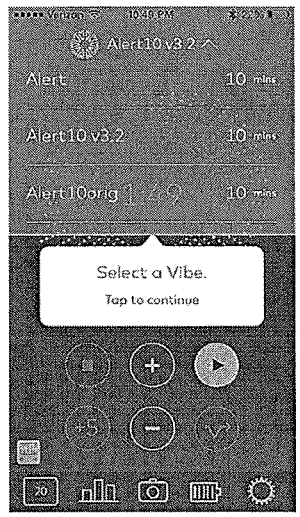
FIGS. 10A-10L show screens of an app for controlling a neurostimulator for TES that display a series of messages to instruct a user on the function of various user interface elements.
Figure 10B:
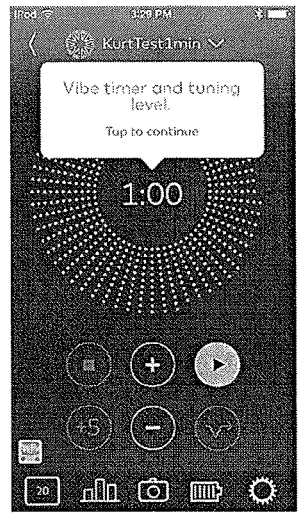
Figure 10C:
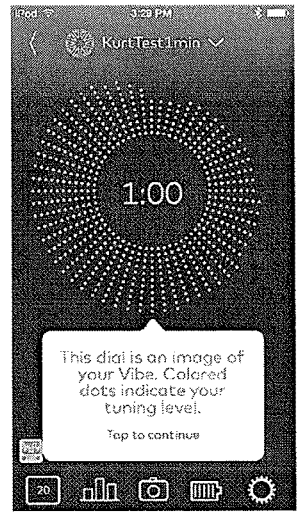
Figure 10D:
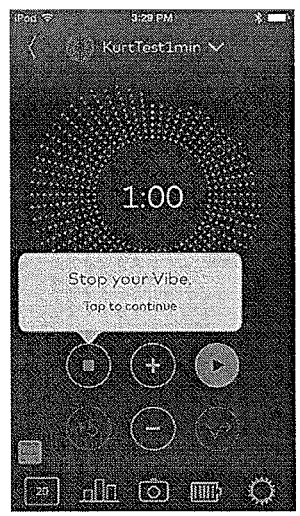
Figure 10E:
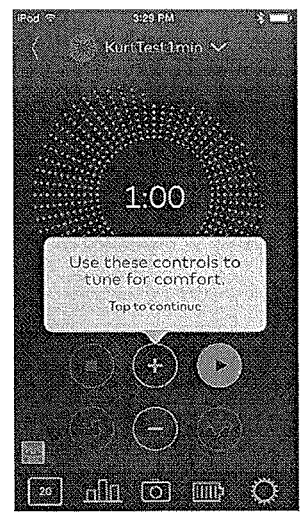
Figure 10F:
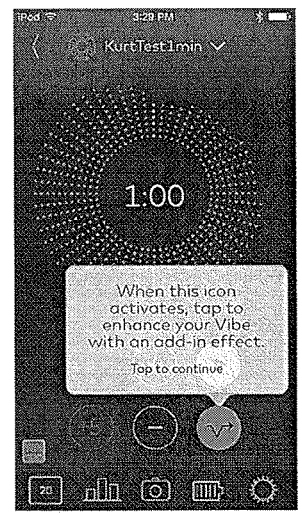
Figure 10G:
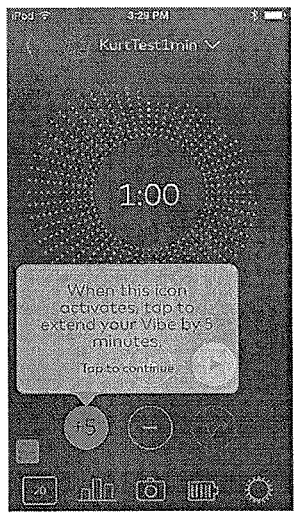
Figure 10H:
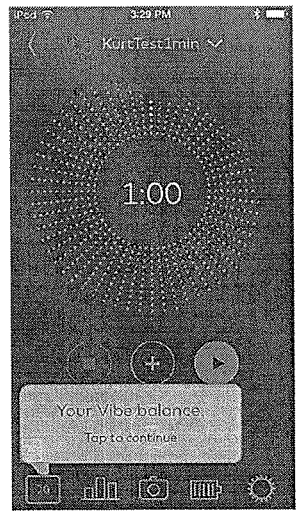
Figure 10I:
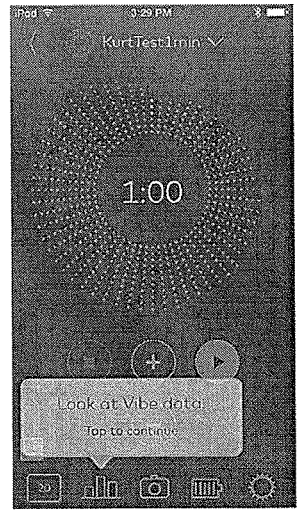
Figure 10J:
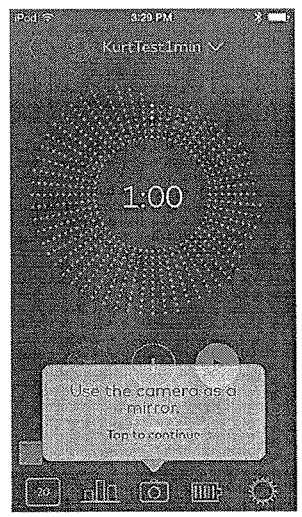
Figure 10K:
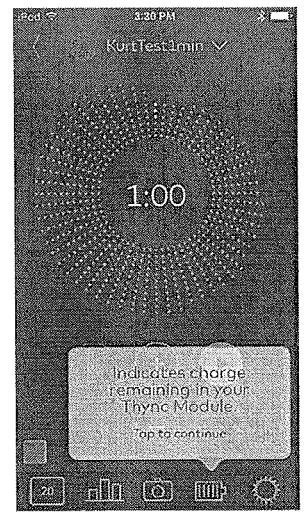
Figure 10L:
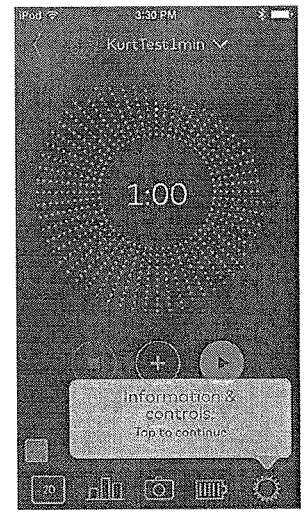
Figure 11:
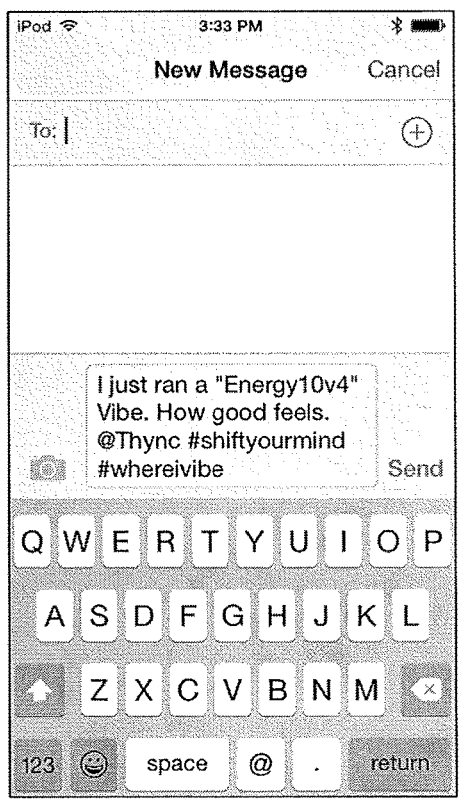
FIG. 11 shows a messaging screen on a smartphone with auto-populated content for sharing by a user of a TES system.

In general, the apparatus may allow a user to select a particular ensemble waveform (vibe) and modify the properties of that vibe during use, as shown in FIG. 10A, and to modify the selected ensemble waveform as it is being applied. For example, as shown in FIG. 9, the UI may allow the user to adjust the intensity (e.g., current, frequency, DC offset, etc. or some combination thereof) using one or more controls (buttons, sliders, knobs, etc.), to pause operation, to add additional duration (time) and/or to trigger a transient increase in intensity or other signal change. The UI may also show the current location within an ensemble waveform and may show what to expect (duration, intensity) in the future. FIGS. 10B-10L illustrate one example of a UI, describing the features. These figures may also be presented by the UI to a user to explain operation of the UI.

Figure 12:
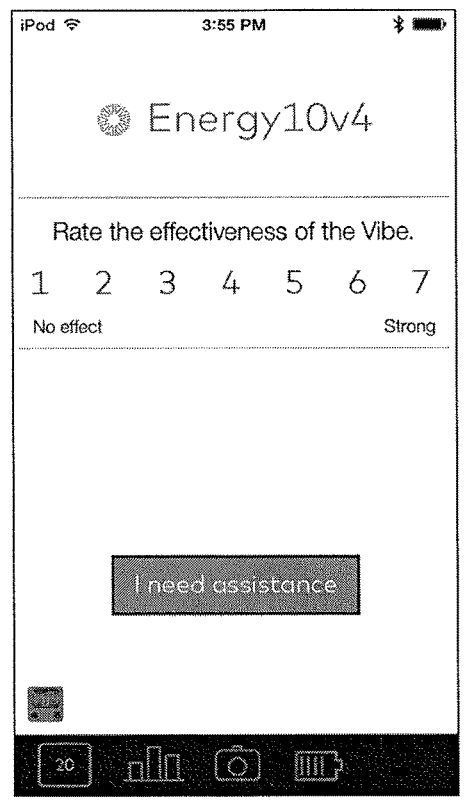
FIG. 12 shows a screen of an app for controlling a neurostimulator for TES that enables a user to provide feedback on efficacy and request customer support assistance.

Any of the UIs described herein may also be configured to communicate with social media, including existing general-purpose social media platforms (e.g., Facebook, Twitter, etc.) or dedicated (e.g., TES-specific social medial) platforms. As already mentioned, any of these apparatuses may present user rankings associated with each ensemble waveform, and/or may also prompt a user for user-reported information about any of the TES ensemble waveforms, as shown in FIG. 12; in addition, the apparatuses described herein may also collect and/or present unprompted user or ranking information, including number of downloads, number of completed runs ("popularity"), intensity modifications, number of aborted runs, etc.

A UI may also be used to determine and/or present analytics about the operation of the TES apparatus. For example, FIGS. 13A-13E illustrate analytics user interfaces for a sample user. As shown in FIG. 13A, the UI may be used to select information about the user's usage history (vibe history, etc.), the devices used by the user (device), and account information, and may also be used to purchase additional electrode strips, purchase or modify ensemble waveforms, or to view information about the individual's operation of the apparatus. The UI may also be configured to allow a user to login/logout, as mentioned, or to log in as a guest. The UI may also be configured to associate with one or more specific devices, and may be configured to control operation of the TES apparatus (see, e.g., FIG. 13B). The UI may also provide information specific to the UI and/or the TES apparatus (see, e.g., FIG. 13C). The UI may provide user analytics (e.g., number, duration, frequency of one or more, or all, ensemble waveforms, etc.), including historical information (FIG. 13E) such as a history of operation of the apparatus.

Rental/Purchase and Tracking of "Vibes"

As mentioned above, the TES waveforms referred to herein may be called waveforms, ensemble waveforms or "vibes". Any of these ensemble waveforms may be preconfigured and offered, sold, set, rented, or otherwise made available to a user having a TES neurostimulator as described and shown herein (and incorporated by reference above). For example, a vibe may be tracked (usage and/or possession), and may provide accounting for eCommerce (i.e., buying a credit to play a particular TES waveform/waveform ensemble, which is distinct from purchasing an electrode, a neurostimulator module, an app, etc.). For example, users may purchase packages (e.g., a combo pack) of electrode assemblies (also referred to as electrode strips, i.e. calm strips and energy strips for different electrode locations and cognitive effects induced) and/or TES sessions (also referred to as ensemble waveforms or vibes). The system may maintain a count of a user's available vibes (e.g. on the neurostimulator, on a user computing device that controls or otherwise communicates with the neurostimulator, on a remote server connected to the neurostimulator (or to the user computing device connected to the neurostimulator) via the Internet. A user may have login credentials or other security that indicates they are the user (their account is to be debited for) a TES session (e.g., a vibe), and their 'vibe balance' may be decremented. A vibe credit may be associated with a single TES session (of any length), by a length of time during TES session(s), by a duration from the onset of a first TES session, etc.

The system may make the electrodes reusable many more times and will sell or lease (rent) Vibes rather than (or in addition to) electrode assemblies.

For example, described herein are systems for operating a marketplace of ensemble TES waveforms. Each of a plurality of TES waveforms may be associated with an outcome or evoked cognitive effect, such as calm, relaxation, energy, etc. The system may include a database of such ensemble waveforms, and may also include additional associated information, such as: a summary/description of the vibe (intended effect, duration, recommended electrode configuration, recommended audio and/or visual accompaniment, etc.), rankings/ratings, creator, recommended or required electrode configurations, date of creation, music or other audiovisual accompaniment, and the like. Ensemble waveforms (vibes) from the database may be accessed by the one or more users, who may purchase, rent and/or contribute vibes to/from the database. The system may present a description of each vibe and a rental and/or purchase price for each vibe. The system may track purchases/rentals, and may regulate distribution of purchased/rented vibes.

Fitting

In general, the methods and apparatuses (including the UIs) described herein may be configured to optimize the application of TES ensemble waveforms, including optimization (by the apparatus and/or by the user, including automatically guiding the user) of the fit of the electrodes with the apparatus. For example, for fitting an electrode strip and/or TES apparatus, the apparatus may be configured (e.g., using the UI) to instruct a user to try 'dry fit' first the electrode first, by figuring out placement with just the neurostimulator module before attaching it to the adhesive electrode assembly. This may permit ease of sliding, rotating, shifting unit on the head to find correct positioning with regard to placement and contour of module vs. head. Once the user has determined the correct position for themselves, they may attach the adhesive electrode assembly and position it again at the same location (e.g. by using a front facing camera, including one that automatically compares the real-time position to the one selected earlier during the dry fit phase) and/or a mirror. See, e.g., FIGS. 14L-14N.

Customization

As mentioned above, any of these apparatuses may be used to customize the delivery of TES via the device, including selecting one or more specific ensemble waveforms. For example, an ensemble waveform may be purchased having specific properties and/or for use with a specific electrode strip. Custom ensemble waveforms (vibes) may control the wearable apparatus to deliver a particular type of TES (controlling frequency, current, timing, duration, DC offset, etc. as described above). A database and UI as described herein may "push" (electronically distribute) a particular TES waveform to a particular user based on their login, and/or based on the user's selection, rental or purchase of a particular TES waveform. This may allow creation and distribution of vibes customized for particular users or classes of users. See, e.g., FIG. 14o.

Methods of Operation

Figure 14A:
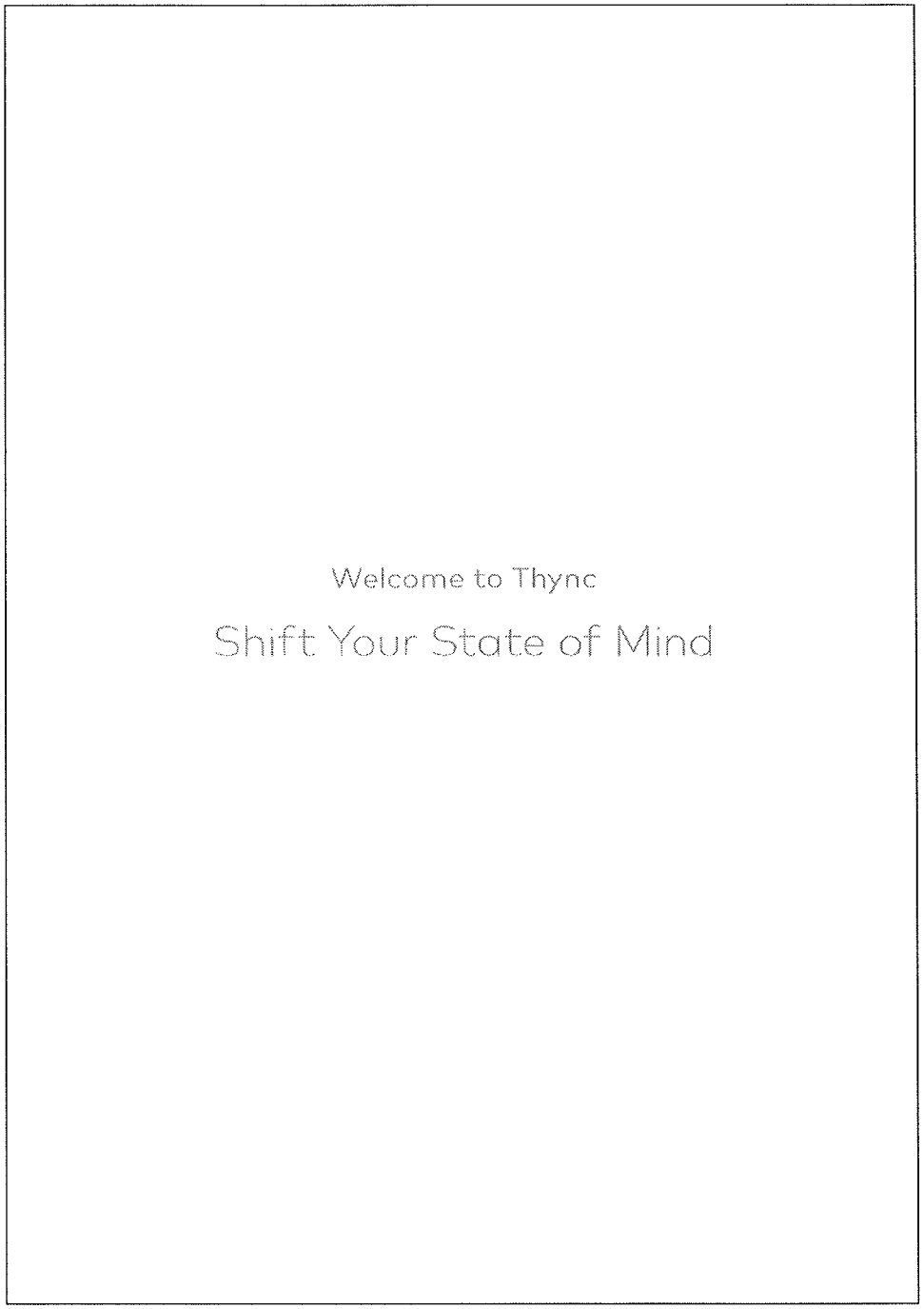
FIG. 14A shows a title page of a user guide for a TES system.
Figure 14B:
FIG. 14B shows a table of contents page of a user guide for a TES system.
Figure 14D:
FIG. 14D shows a first TES experience (i.e. 'Vibe') description page of a user guide for a TES system.
Figure 14E:
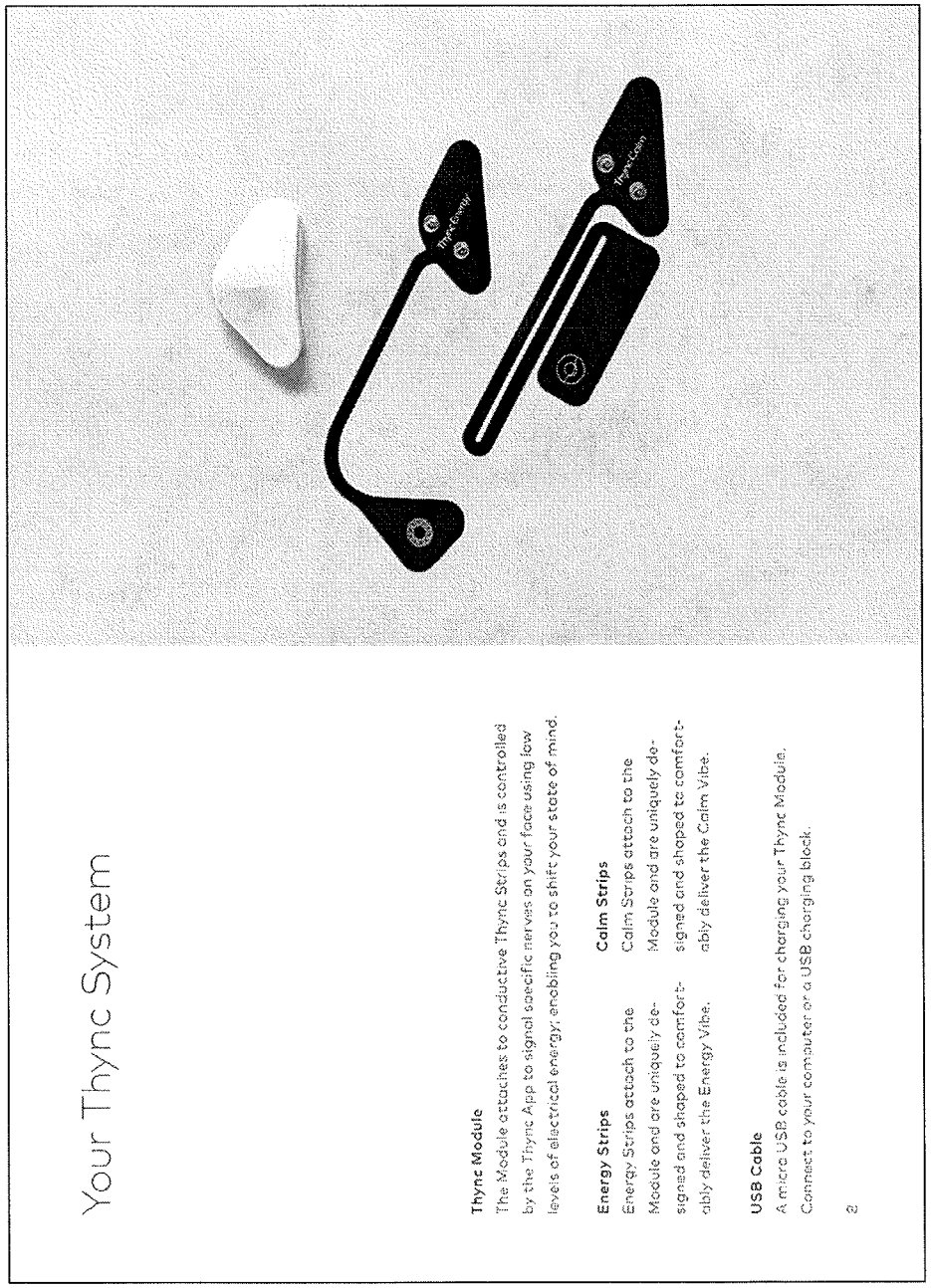
FIG. 14E shows a system description page of a user guide for a TES system.
Figure 14F:
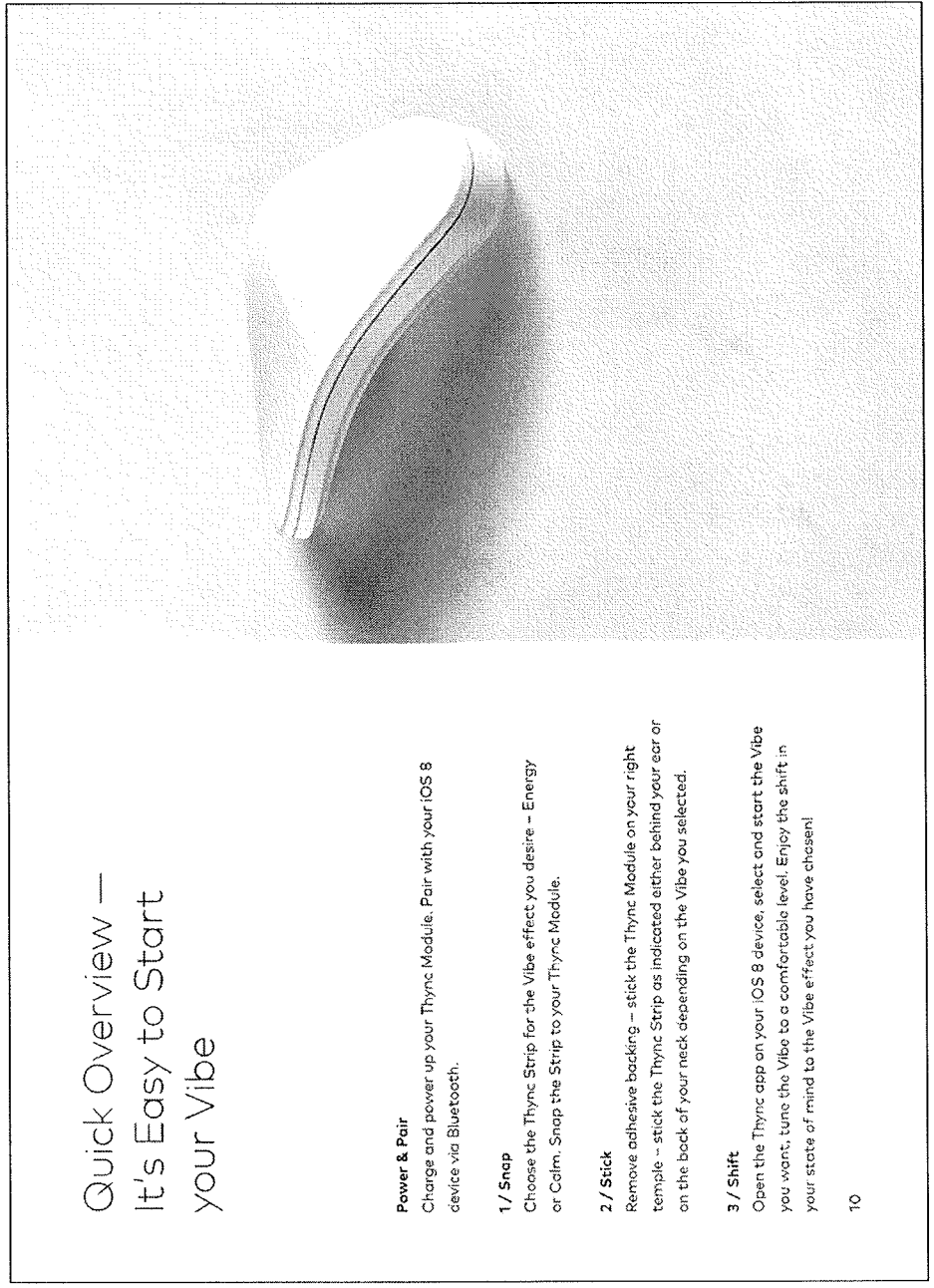
FIG. 14F shows an overview page of a user guide for a TES system.
Figure 14G:
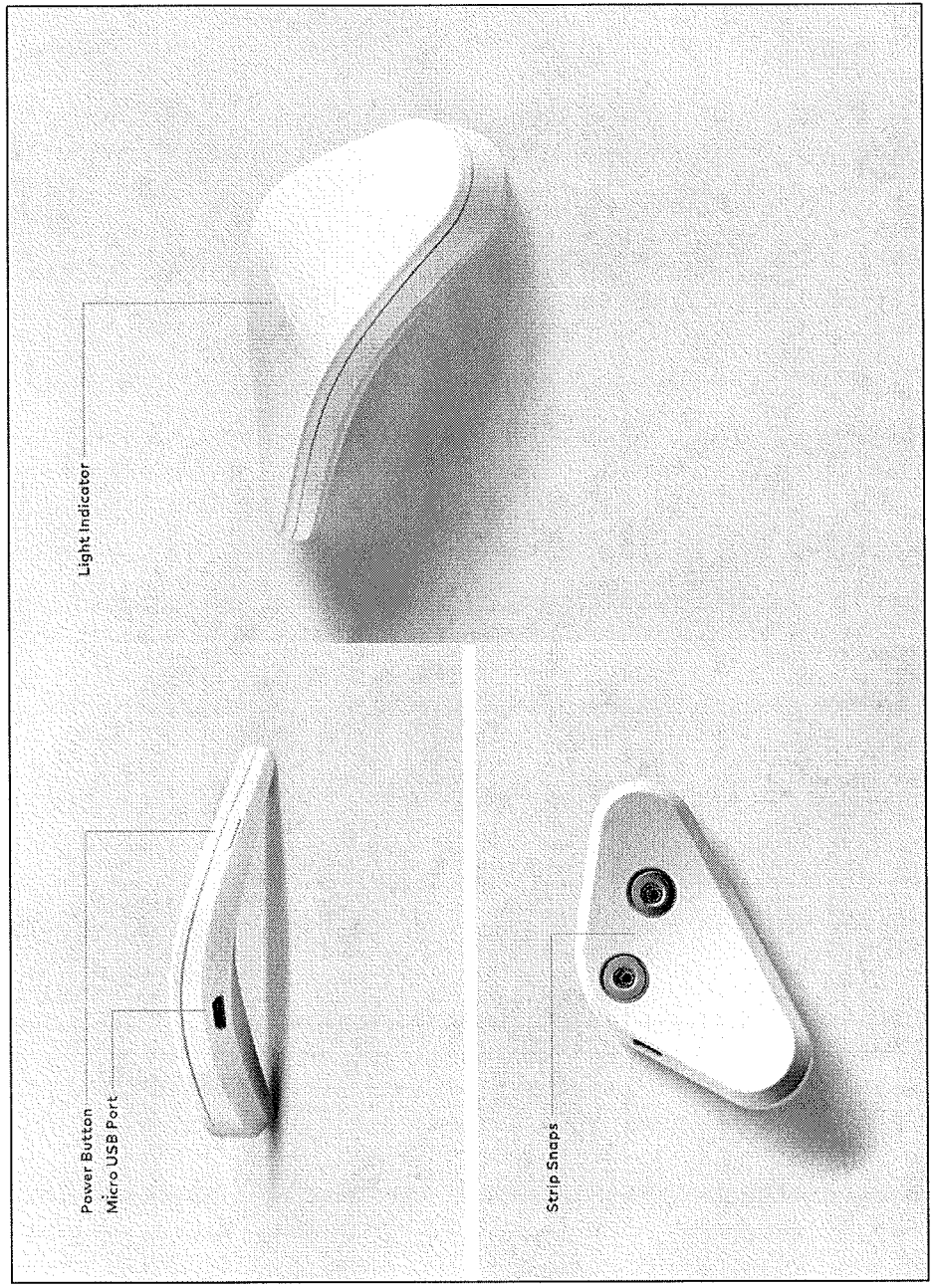
FIG. 14G shows a page of a user guide for a TES system indicating components of a wearable TES neurostimulator.
Figure 14H:
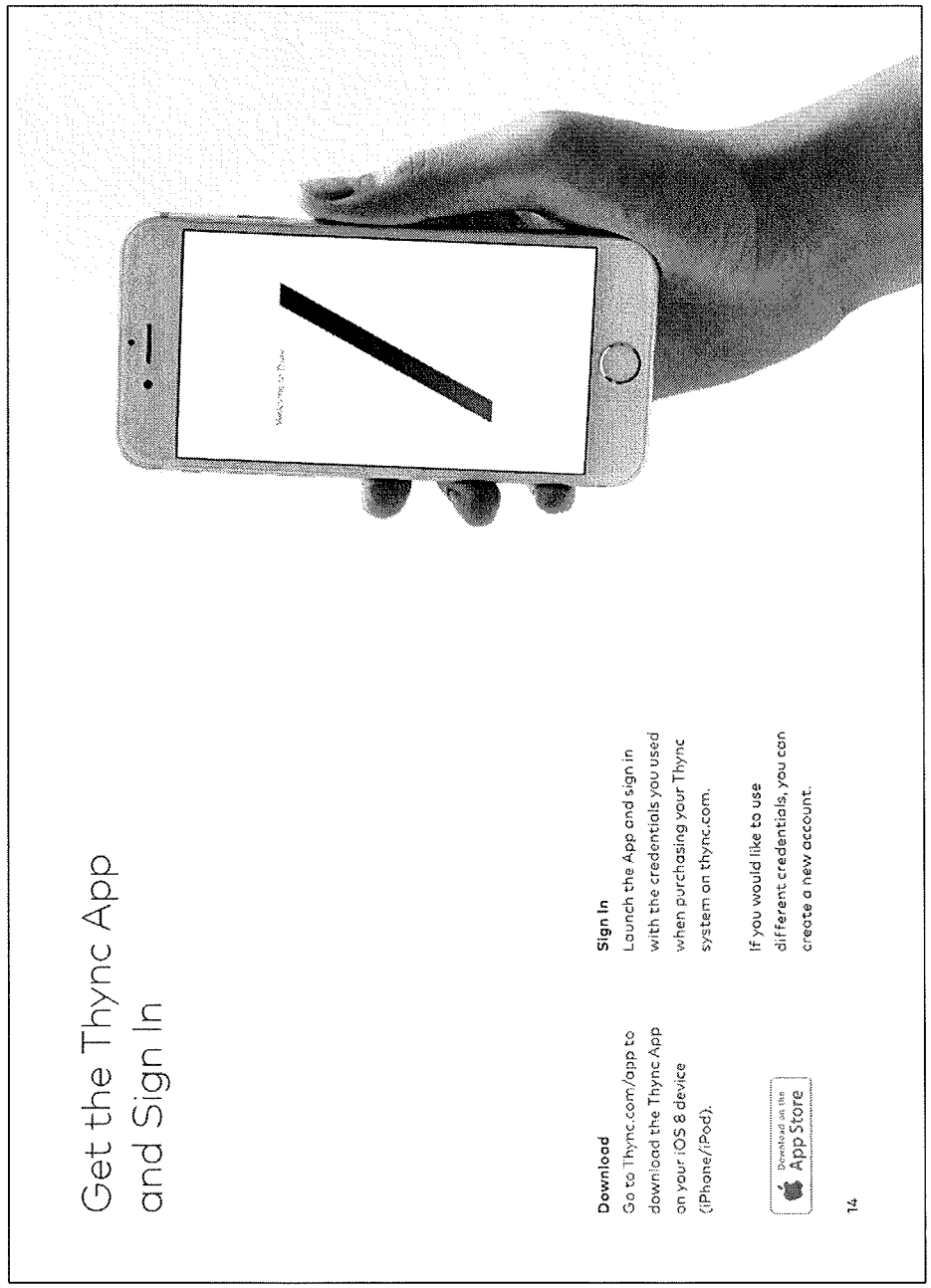
FIG. 14H shows a page of a user guide for a TES system that guides a user to download an app for controlling the TES neurostimulator from a smartphone.
Figure 14I:
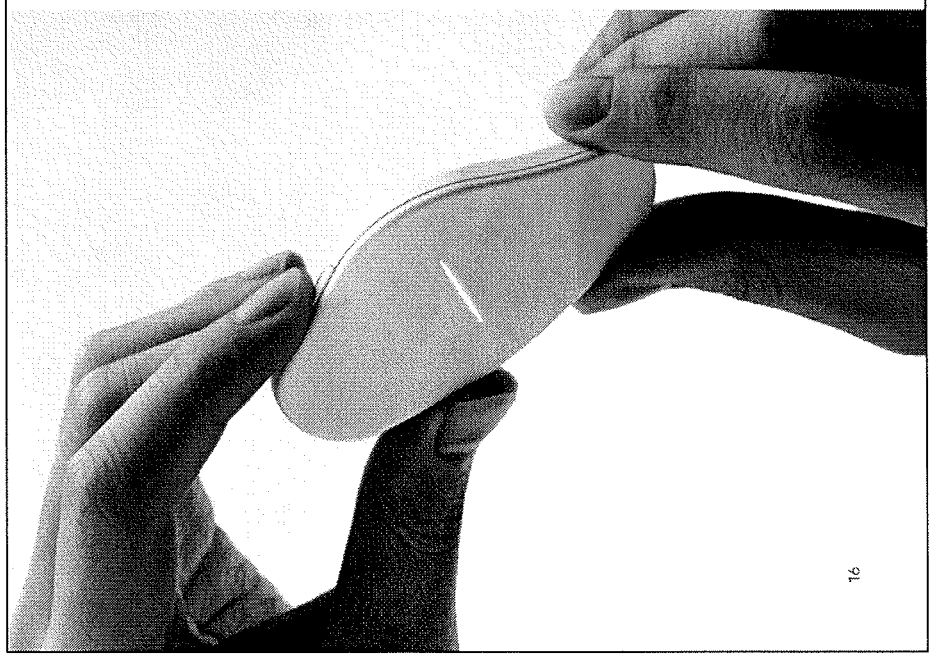
FIG. 14i shows a page of a user guide for a TES system with instructions for wirelessly pairing to a smartphone and power/charging of a wearable TES neurostimulator.
Figure 14J:
FIGS. 14J-14K show pages of a user guide for a TES system with instructions for attaching an electrode assembly (i.e. 'strip') to a wearable TES neurostimulator (i.e. 'Module').
Figure 14K:
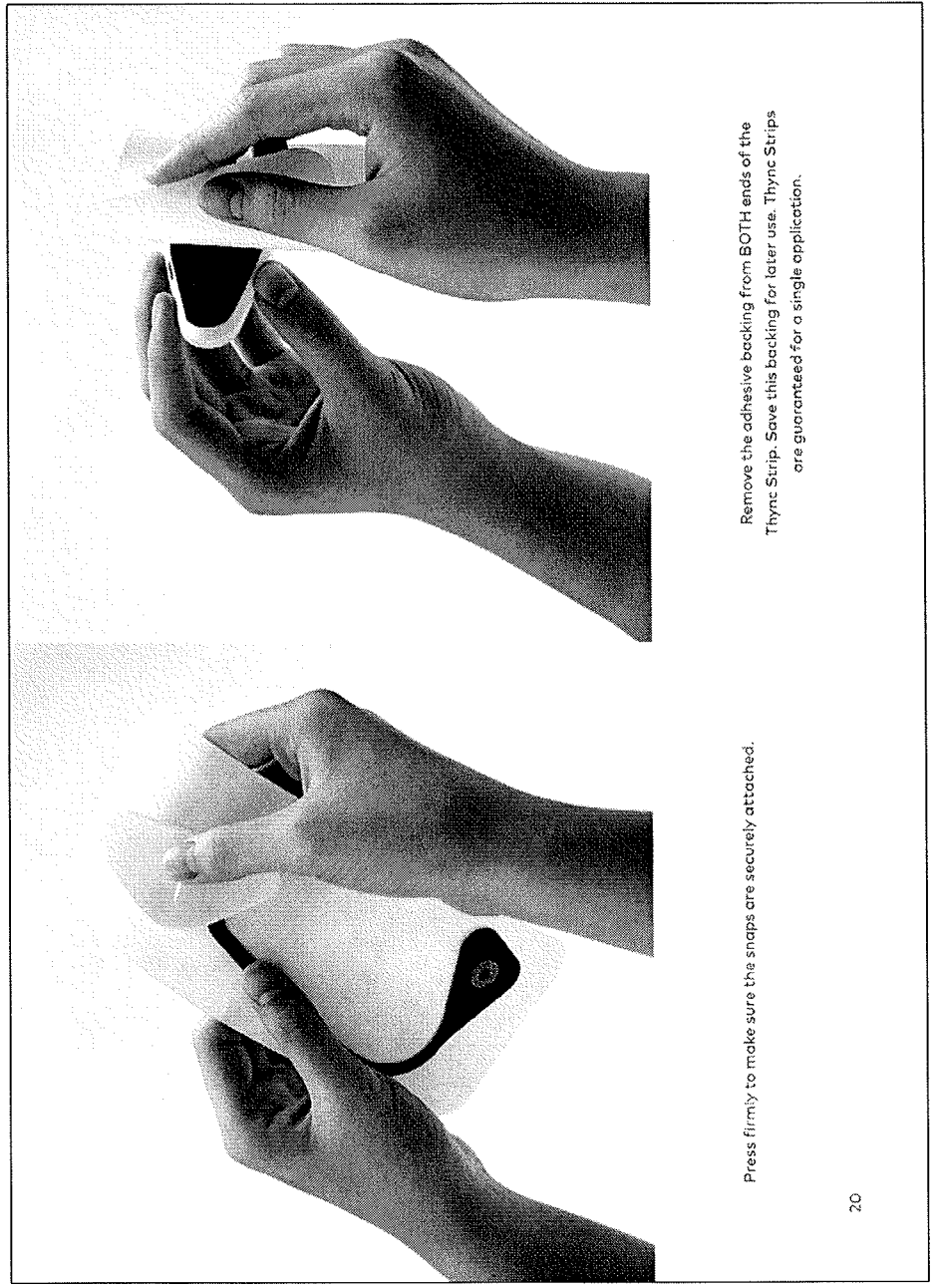
Figure 14L:
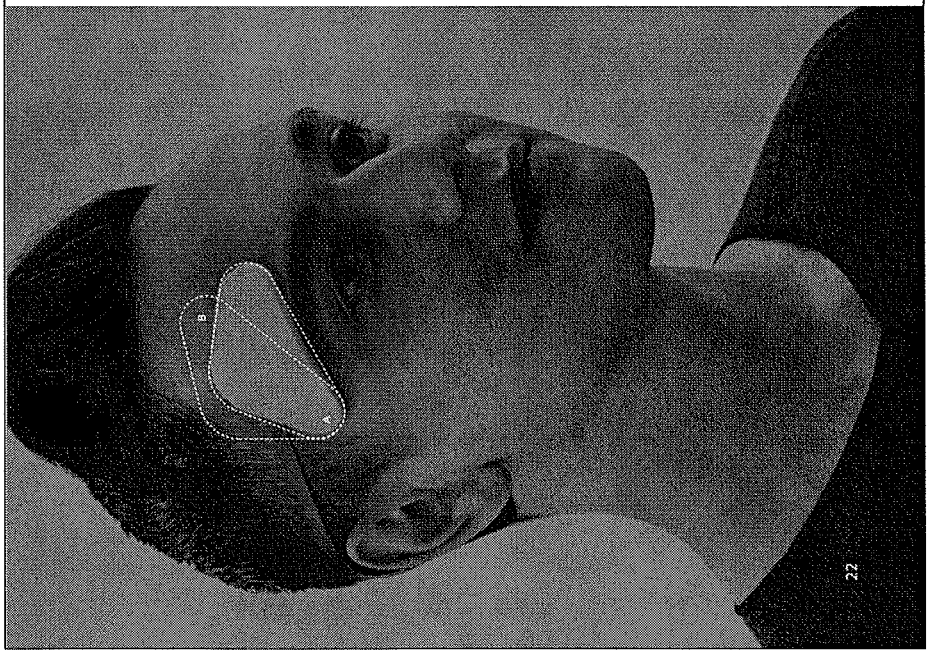
Figure 14M:
Figure 14O:
Figure 14P:
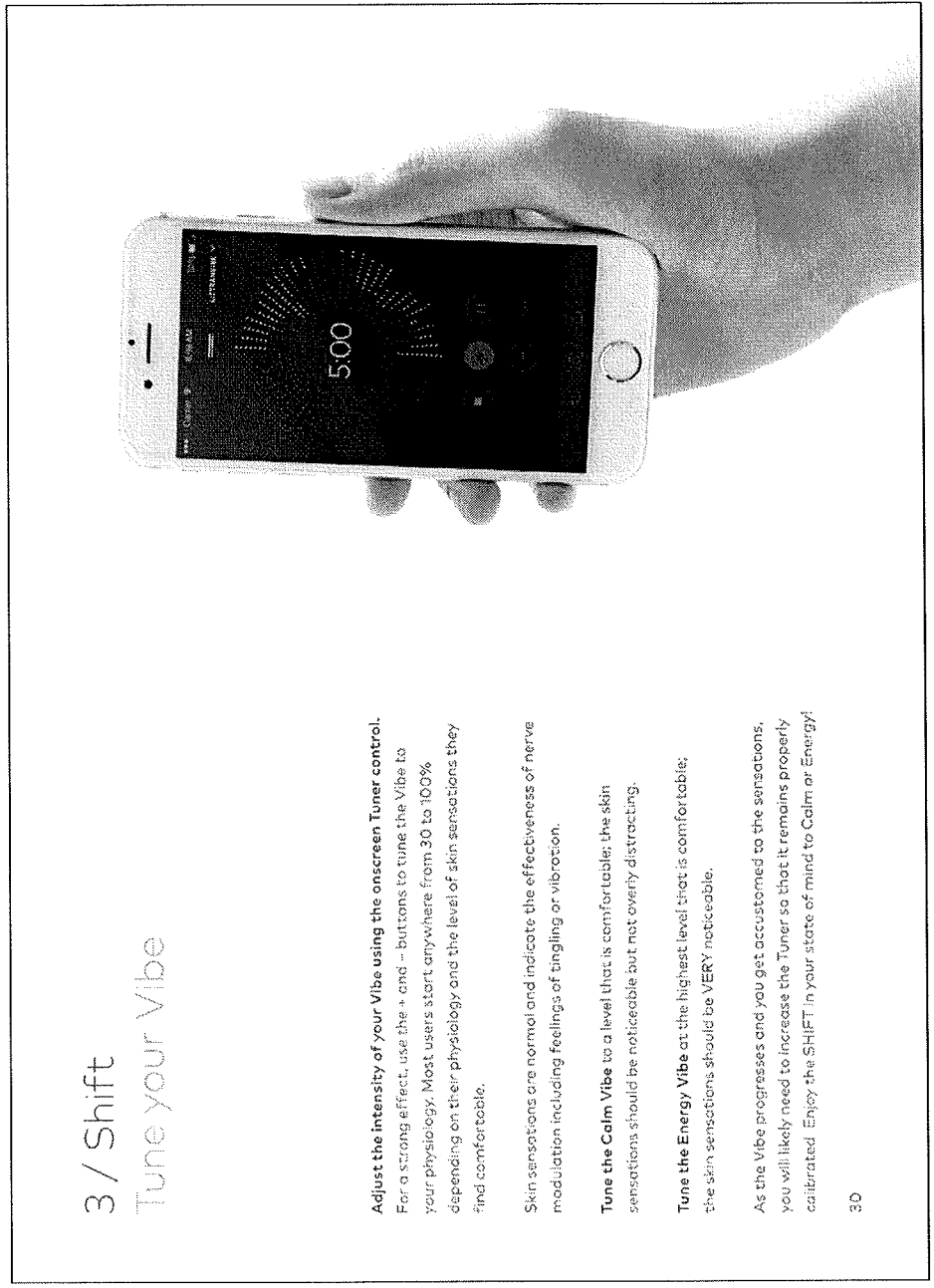
Figure 15:
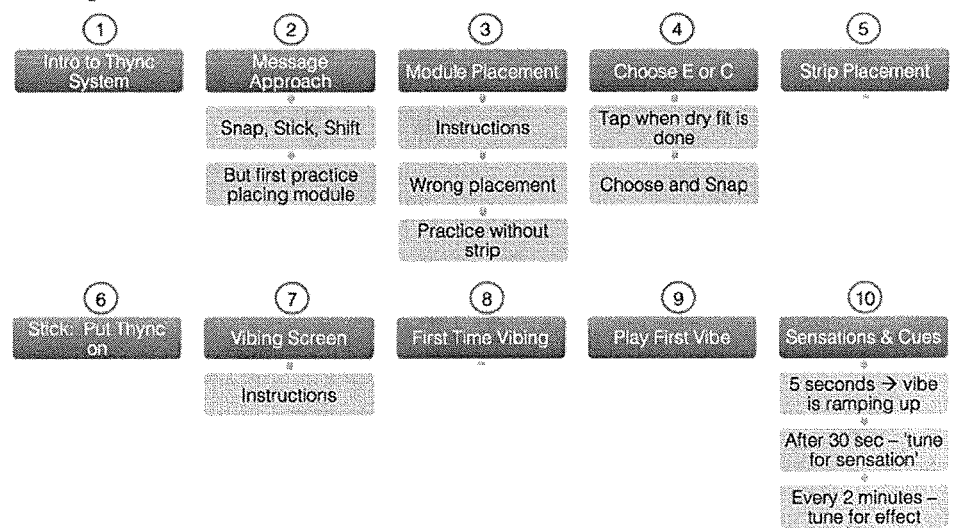
FIG. 15 shows a workflow for instructions, including text, video, and user interaction for teaching a naïve user how to use a wearable neurostimulator system for TES.
Figure 16A:
FIG. 16A shows a resource (e.g. website) describing a wearable TES neurostimulator, electrode assemblies, and app (referred to as the 'Thync System') for user-actuated TES to induce a cognitive effect.
Figure 16B:
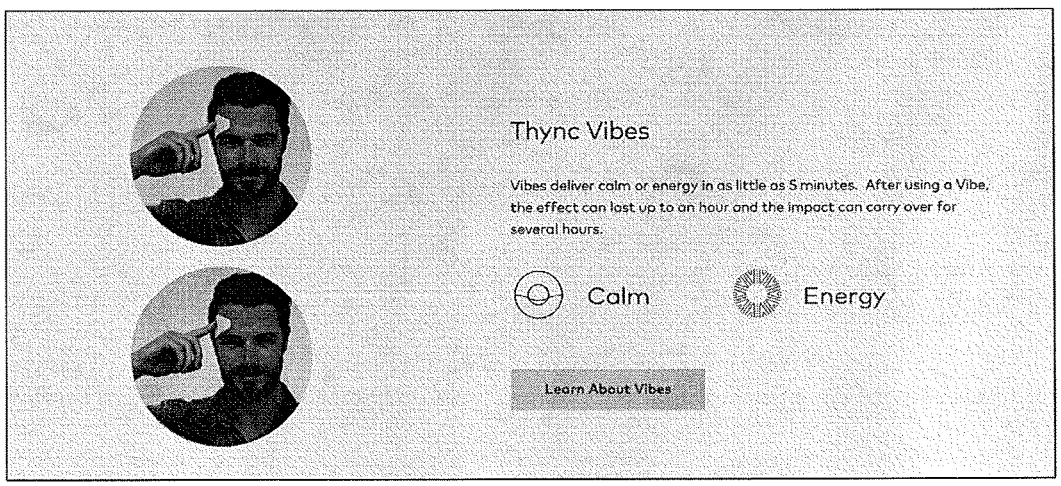
FIG. 16B shows a resource (e.g. website) describing two categories of TES (i.e. Calm Vibes and Energy Vibes) that can be delivered to a user by a wearable TES neurostimulator to induce a cognitive effect.
Figure 16C:
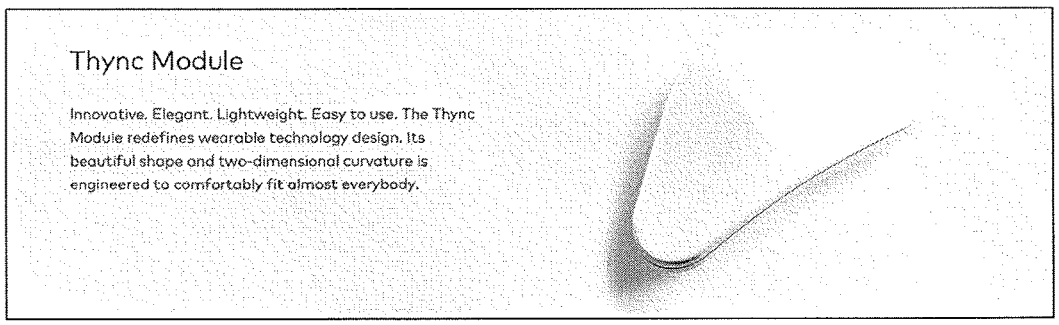
FIG. 16C shows a resource (e.g. website) describing a wearable neurostimulator (also referred to as a 'Thync Module').
Figure 16D:
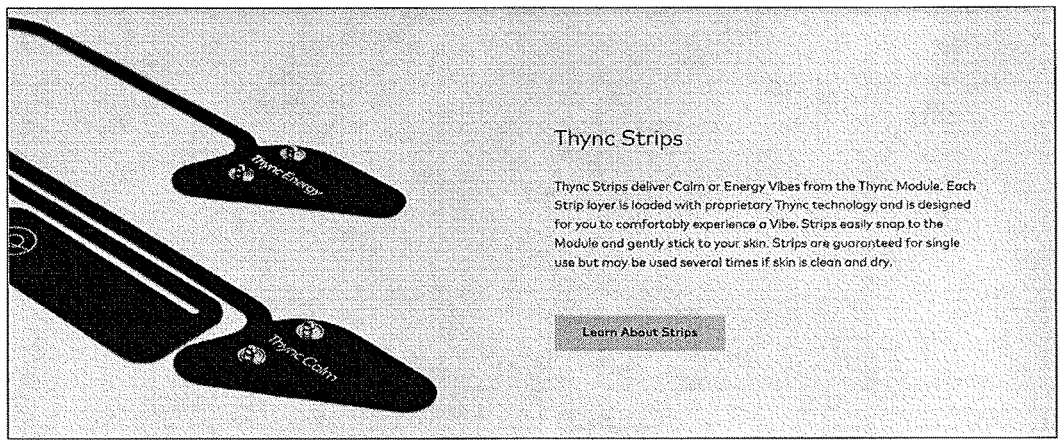
FIGS. 16D-16E show resources (e.g. websites) describing electrode assemblies for inducing a cognitive effect via a wearable neurostimulator (also referred to as a 'Thync Strips').
Figure 16E:
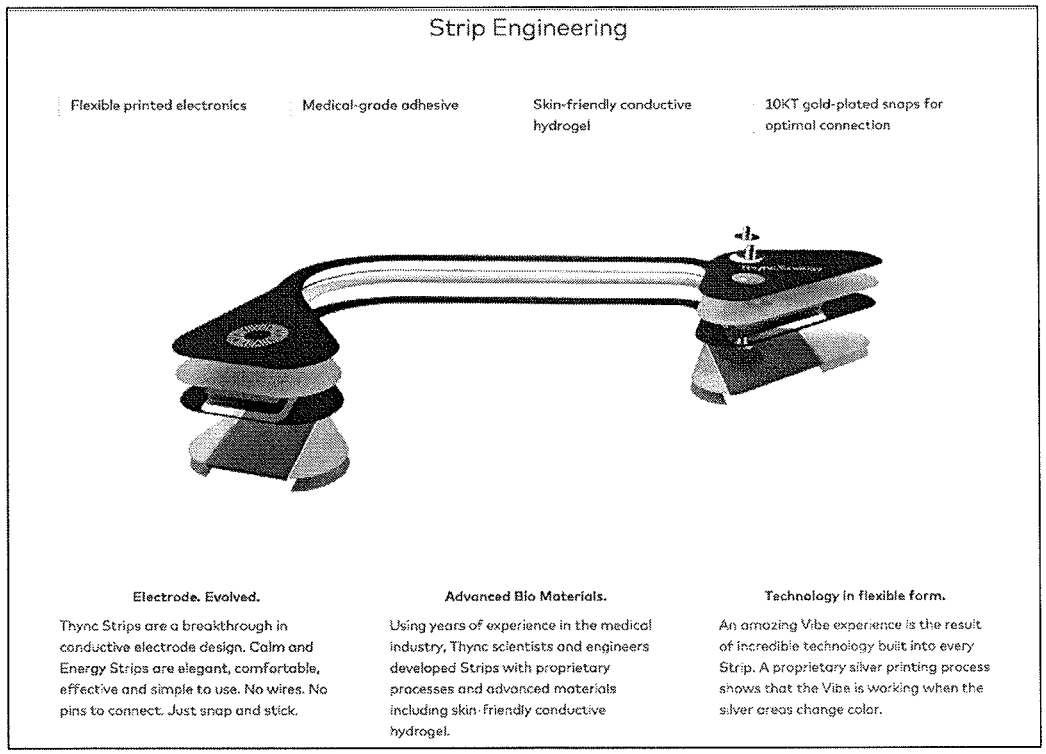
Figure 16F:
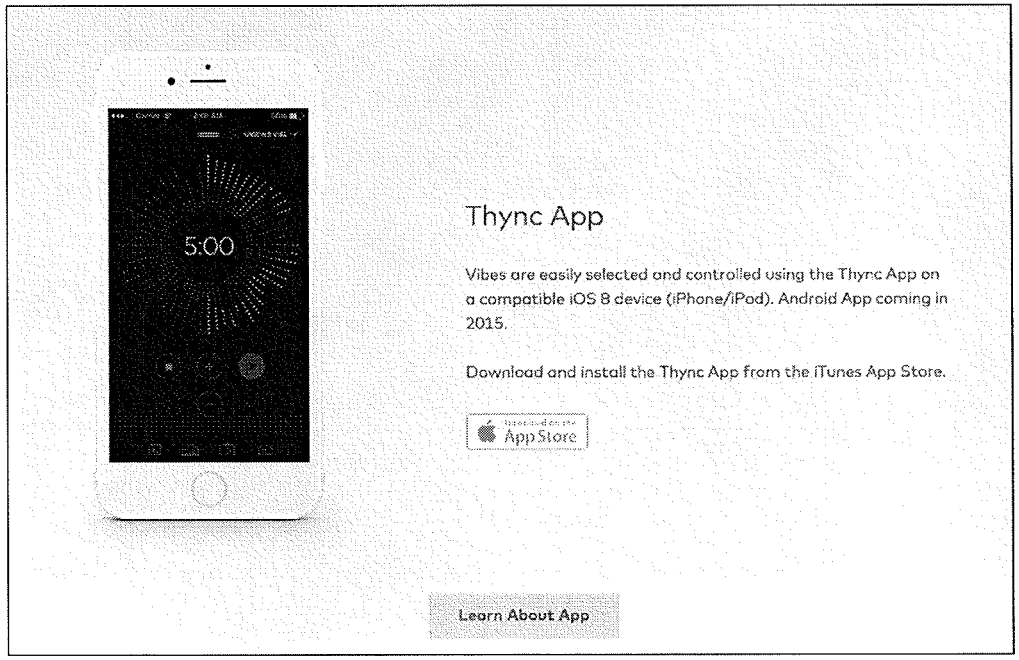
FIG. 16F shows a resource (e.g. website) describing a dedicated software (also referred to as a 'Thync App') on a user computing device for controlling a wearable neurostimulator.
Figure 16G:
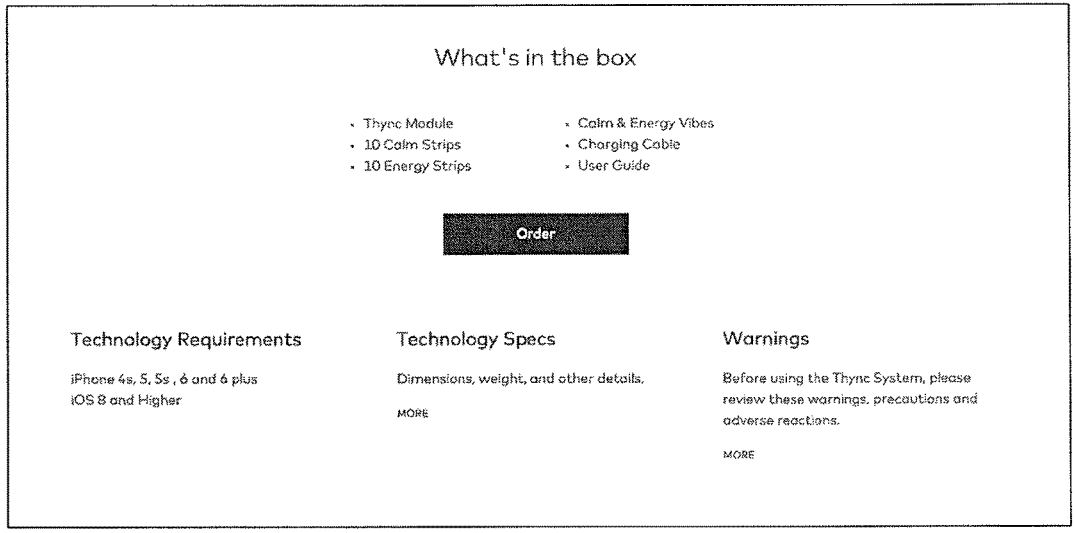
FIGS. 16G-16H show resources (e.g. websites) describing the components of a wearable TES system and its intended use.
Figure 16H:
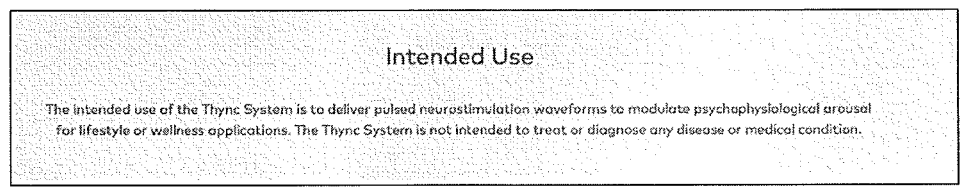
Figure 17A:
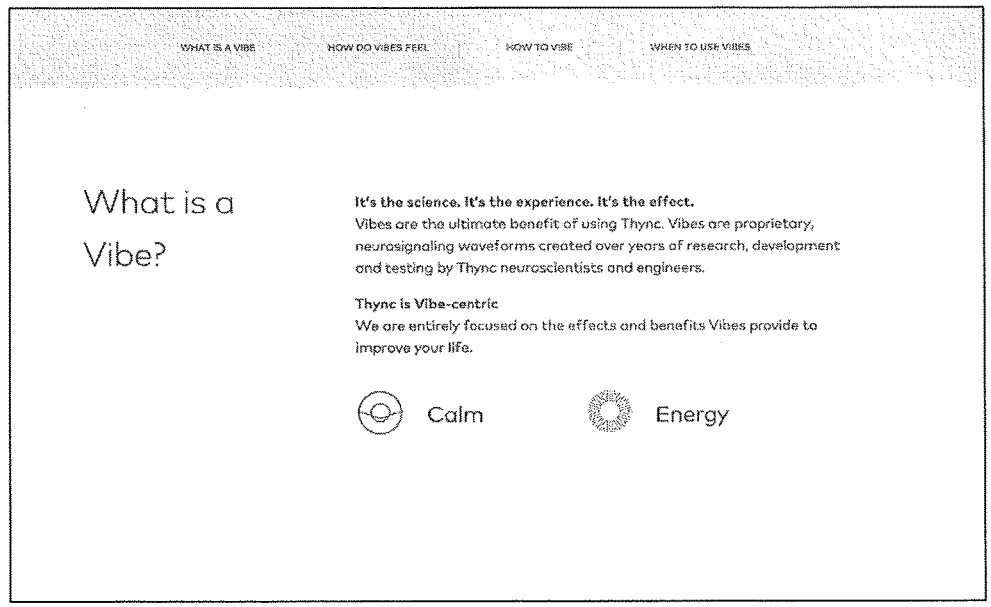
Figure 17B:
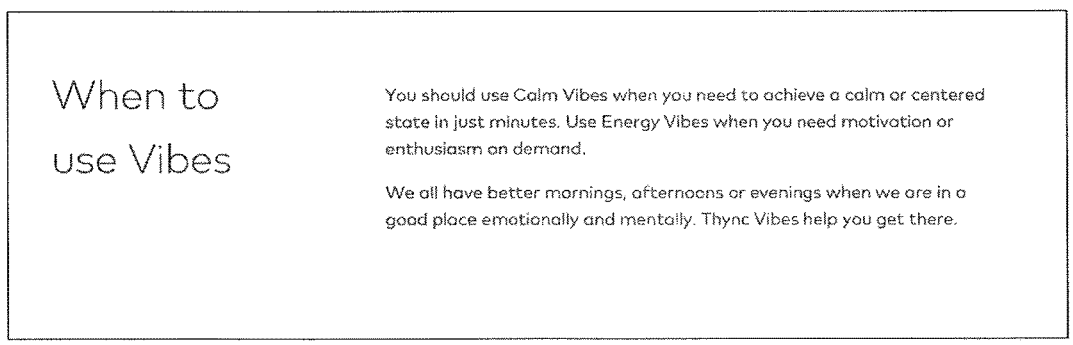
Figure 17E:
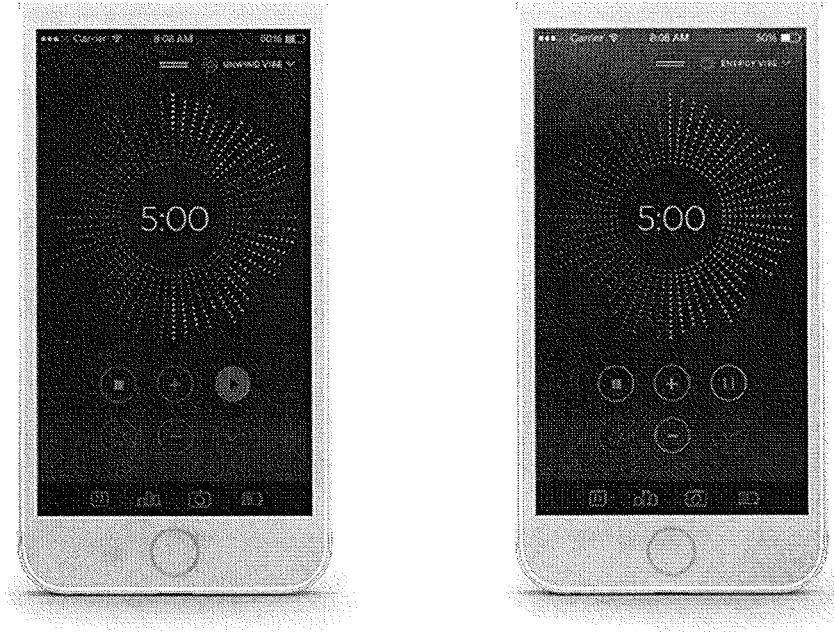
Figures 19A, 19B:
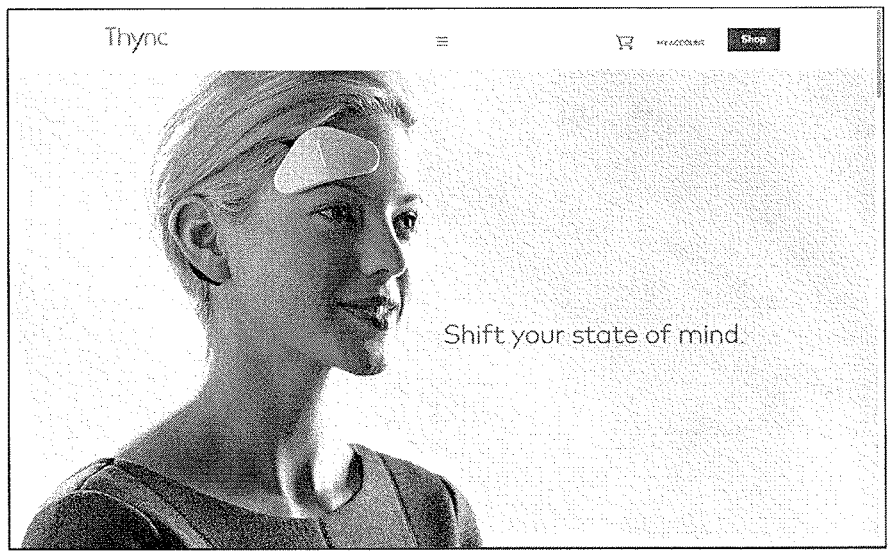
FIGS. 19A-19F show resources (e.g. websites) that describe a high level summary of a wearable neurostimulator system that uses TES to induce cognitive effects of increased energy or enhanced calmness in users.
Figure 19C:
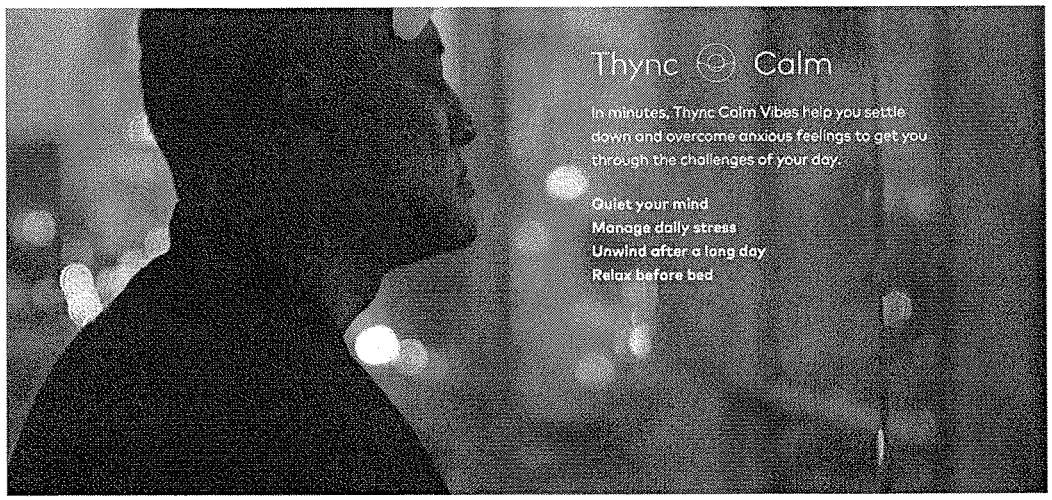
Figure 19D:
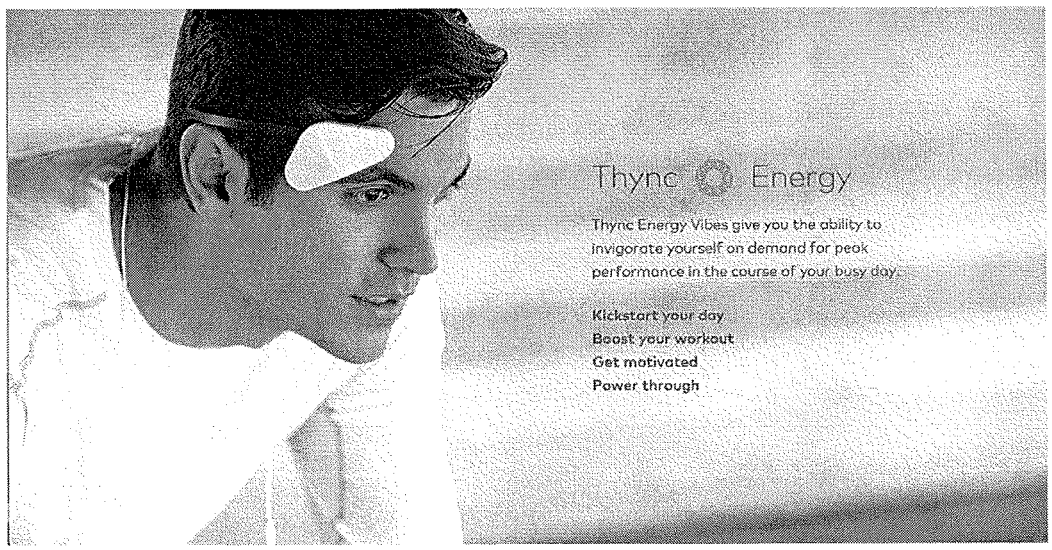
Figure 19E:
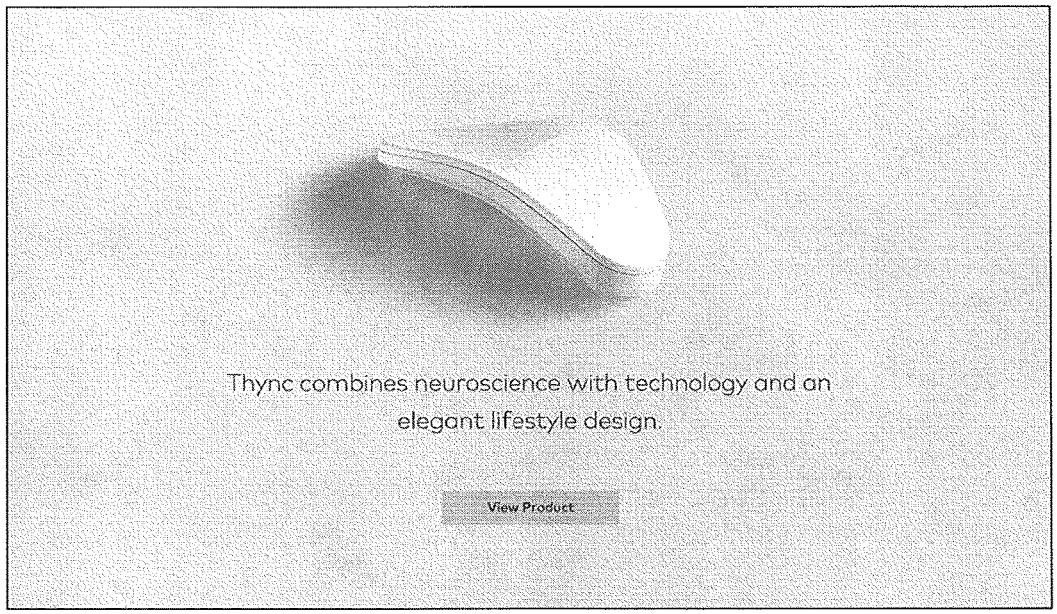
Figure 19F:
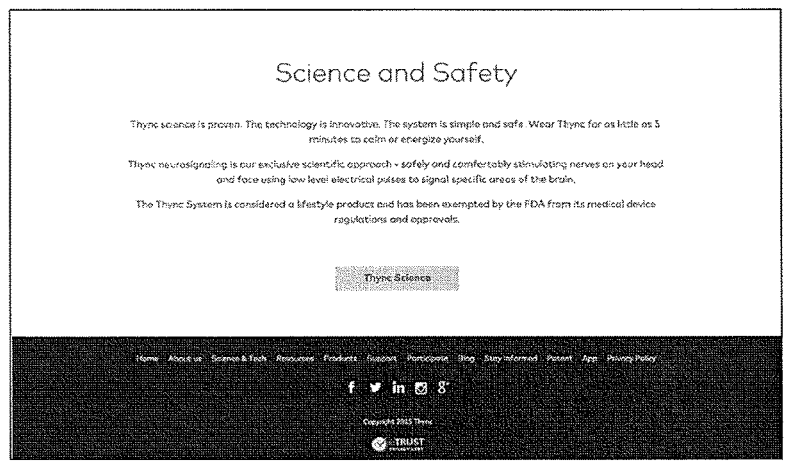

As illustrated in FIGS. 14P-15, the user may control delivery of the TES ensemble waveform, including modulating the intensity as the waveform is being delivered. Messages during a TES session may be displayed, e.g., by an app on a user interface of a user electronics device, and may instruct a user (especially beneficially for less experienced or naïve users) to find the correct intensity to achieve a cognitive effect with minimal discomfort by changing the intensity the right amount at the right time.

These messages occur at specific times relative to TES waveform onset with messaging appropriate for that epoch of the waveform. For example, within 5 seconds the UI may inform a user that: "vibe is ramping up"—No need to adjust Vibe tuner unless you find it comfortable to reduce the intensity; within 1 minute, the app may instruct the user that: "time to calibrate tuner", "tune the Energy Vibe to the highest level that is comfortable, "tune the Calm Vibe to the level where you start to feel pressure and then back off", etc. The app may also inform the user (e.g., at five minutes: "find your sweet spot" Adjust +/−6 and see how that feels after 15-20 seconds), or for "energy" vibes "look for heightened alertness, feeling of wanting to move around", or for calm vibes, "look for pleasurable tingles running up your neck, feeling detached and lighter", etc.

The apparatus may instruct new users in how to use a self-actuated wearable TES neurostimulator system is critical to ensure they use the system safely and correctly to achieve a cognitive effect. An animated video with a descriptive voice-over is an effective means for training naïve users. For example, any of the methods of operating or instructing a user to operate a TES apparatus such as those described herein may include the information (which may be presented by, e.g., an animated video that may use visuals and/or a voice over text) as follows: "The apparatus is wearable technology that uses neurosignaling to deliver on demand calm or energy in minutes. Using the apparatus to shift your state of mind is as easy as Snap—Stick—Shift." "This system has three components—the Applicator module, Vibe strips, and Vibes delivered through the app on your iOS device." "Turn ON by pressing the POWER button until the white light blinks. Make sure your module is fully charged. Then, turn on BLUETOOTH on your iOS device." "To PAIR the module, open the app on your device and follow the screen prompts. The white light will pulse to indicate pairing is underway and will become SOLID WHITE when successfully paired." "Energy strips have a different shape than Calm Vibe strips." "Select your Vibe strip and SNAP it directly onto the Applicator Module." "The module is designed and contoured to precisely fit this area on most people. Find the place where it rests FLUSH against your skin." "PLACE the module so that it lies on both your temple and forehead area, above your right eyebrow. You may need to move it around until it feels just right. Make sure no hair, oils or lotions are on the skin." "Remove the adhesive backing from the strip and press firmly for several seconds to STICK the module in place." "The Energy strip should be placed on the bone directly behind your right ear. The lower half of this bone, directly between your ear and your hairline, is the ideal location. The edge of the strip should just touch the back of your ear." "You may have trouble positioning this strip correctly on your first use. If you notice strong skin sensations at this location during a vibe, try pressing the strip down firmly—if this significantly reduces the skin sensations, this indicates that the strip is not making good contact with your skin and you will want to pause and adjust it." "The Calm strip should be placed horizontally and centered on the back of your neck, just below your hairline." "Remove the adhesive backing. Again, make sure no hair, oils or lotions are on the skin in this area. Press firmly for several seconds to STICK the end of the strip in place." "Once the Applicator module and Vibe strip are in place, running the vibe is easy to SHIFT your state of mind. Open the app on your iOS device, and select the type of Vibe that corresponds to the strip you have selected, 'Energy' or 'Calm.'" "For each vibe, there are 10 and 20 minute sessions available. A 10 minute vibe will give you the option to add two 5 minute extensions. Choose your desired session and the vibe TUNING screen will appear." "Press PLAY to start and wait at least 30 seconds before tuning the intensity of your Vibe. Press PAUSE or STOP before removing the unit." "After 30 seconds, use the + and − buttons to tune the intensity and comfort of your vibe to your unique physiology. Now . . . enjoy your Vibe!" Any method of operating the systems described herein (including incorporated by reference above) may include one or more of these statements, or an equivalent statement.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of applying transdermal electrical stimulation to a user using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, the method comprising:

adhesively securing the first active region of the electrode apparatus to the user's temple;

bending the connecting region out of the plane;

adhesively securing the second active region of the electrode apparatus to the user's cheek in front of the user's ear; and coupling a wearable electrical stimulator to a first and second connector extending proud from the first electrode portion so that the wearable electrical stimulator is worn on the user in a first location.

2. The method of claim 1, wherein coupling the wearable electrical stimulator to the first and second connector extending proud from the first electrode portion comprises snapping the wearable electrical stimulator onto the first and second connector wherein the first connector and the second connector are separated from each other by between about 0.7 and 0.8 inches.

3. The method of claim 1, wherein coupling the wearable electrical stimulator to the first and second connector comprises snapping the wearable electrical stimulator onto the first and second connector.

4. The method of claim 1, wherein adhesively securing the first active region comprises attaching a hydrogel on the first active region against the user's head.

5. The method of claim 1, wherein coupling the wearable electrical stimulator comprises connecting an underside of the wearable electrical stimulator to the first and second connector to make an electrical contact with the wearable electrical stimulator and the first and second active regions.

6. The method of claim 1, further comprising applying TES waveforms to evoke a state of energy in the user.

7. The method of claim 1, wherein the wearable electrical stimulator is coupled to the first and second connector before adhesively securing the first active region of the electrode apparatus to the user's temple.

8. The method of claim 1, wherein the wearable electrical stimulator is coupled to the first and second connector after adhesively securing the first active region of the electrode apparatus to the user's temple.

9. A method of applying transdermal electrical stimulation to a user using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, the method comprising:

adhesively securing the first active region of the electrode apparatus to the user's cheek in front of the user's first ear;

bending the connecting region out of the plane;

adhesively securing the second active region of the electrode apparatus to the user's cheek in front of the user's second ear; and coupling a wearable electrical stimulator to a first and second connector extending proud from the first electrode portion so that the wearable electrical stimulator is worn on the user in a first location.

10. The method of claim 9, wherein the wearable electrical stimulator is coupled to the first and second connector after adhesively securing the first active region of the electrode apparatus to the user's cheek.

11. The method of claim 1, wherein the wearable electrical stimulator weighs less than 30 grams.

12. The method of claim 1, wherein a first side of the wearable electrical stimulator has a first thickness that is less than a second thickness of a second side of the wearable electrical stimulator.

13. The method of claim 9, wherein the wearable electrical stimulator is coupled to the first and second connector before adhesively securing the first active region of the electrode apparatus to the user's cheek.

14. The method of claim 9, wherein coupling the wearable electrical stimulator to the first and second connector extending proud from the first electrode portion comprises snapping the wearable electrical stimulator onto the first and second connector wherein the first connector and the second connector are separated from each other by between about 0.7 and 0.8 inches.

15. The method of claim 9, wherein coupling the wearable electrical stimulator to the first and second connector comprises snapping the wearable electrical stimulator onto the first and second connector.

16. The method of claim 9, wherein adhesively securing the first active region comprises attaching a hydrogel on the first active region against the user's head in the first location.

17. The method of claim 9, wherein coupling the wearable electrical stimulator comprises connecting an underside of the wearable electrical stimulator to the first and second connector to make an electrical contact with the wearable electrical stimulator and the first and second active regions.

18. The method of claim 9, further comprising applying TES waveforms to evoke a state of energy in the user.

19. The method of claim 9, wherein a subject-facing surface of the wearable electrical stimulator has a contoured shape.

* * * * *